United States Patent
Anderson et al.

(10) Patent No.: US 11,053,066 B2
(45) Date of Patent: Jul. 6, 2021

(54) PROPELLANT POWERED SYRINGE WITH TRIGGER

(71) Applicant: CONSORT MEDICAL LIMITED, Norfolk (GB)

(72) Inventors: Ian Anderson, Burwell (GB); Rachel Suzanne Koppelman, Cambridge (GB); Alastair Mckean Willoughby, Cambridge (GB); Douglas Jennings, Royston (GB)

(73) Assignee: CONSORT MEDICAL LIMITED, Norfolk (GB)

( * ) Notice: Subject to any disclaimer, the term of this patent is extended or adjusted under 35 U.S.C. 154(b) by 0 days.

(21) Appl. No.: 14/406,167

(22) PCT Filed: Jun. 7, 2013

(86) PCT No.: PCT/GB2013/051509
§ 371 (c)(1),
(2) Date: Dec. 5, 2014

(87) PCT Pub. No.: WO2013/182858
PCT Pub. Date: Dec. 12, 2013

(65) Prior Publication Data
US 2015/0151047 A1 Jun. 4, 2015

(30) Foreign Application Priority Data
Jun. 7, 2012 (GB) ...................... 1210082

(51) Int. Cl.
*A61M 5/00* (2006.01)
*B65D 83/24* (2006.01)
(Continued)

(52) U.S. Cl.
CPC ............. *B65D 83/24* (2013.01); *A61M 5/142* (2013.01); *A61M 5/14526* (2013.01);
(Continued)

(58) Field of Classification Search
CPC ............ A61M 5/2053; A61M 5/14526; A61M 5/155; A61M 2005/14513; A61M 2205/8225; A61M 5/2046
See application file for complete search history.

(56) References Cited

U.S. PATENT DOCUMENTS 2,160,367 A  5/1939 Maxfield
2,802,430 A  8/1957 Filler
(Continued)

FOREIGN PATENT DOCUMENTS

AU   2012100112 A4  3/2012
DE      3827525 A1  2/1990
(Continued)

OTHER PUBLICATIONS

Examination Report, European patent application No. 13728807.2, dated Jul. 25, 2016.
(Continued)

*Primary Examiner* — William R Carpenter
(74) *Attorney, Agent, or Firm* — Marshall, Gerstein & Borun LLP

(57) ABSTRACT

A syringe propellable by propellant that boils at a predetermined temperature, the syringe including a barrel having an outlet at a front end, and a stopper axially moveable in the barrel. The stopper separates a first chamber and a second chamber, the first chamber being axially forwards of the stopper and being configured for containing a medicament, and the second chamber being axially rearwards of the stopper and being configured to receive propellant for acting on the stopper to move the stopper axially forwardly in the barrel to expel medicament through the outlet upon actuation of the syringe. The syringe further includes a third chamber for containing propellant. Upon actuation of the syringe, liquid propellant is released from the third chamber and boils outside of the third chamber at or above the (Continued)

predetermined temperature to provide an increasing vapor pressure in the second chamber that causes the stopper to move axially forwardly and begin to expel medicament through the outlet. At least one trigger for triggering an action is provided, the trigger activated in response to the pressure in the second chamber satisfying a predetermined condition.

17 Claims, 31 Drawing Sheets

(51) Int. Cl.
*B65B 51/26* (2006.01)
*B65B 51/30* (2006.01)
*B65B 31/04* (2006.01)
*A61M 5/20* (2006.01)
*A61M 39/22* (2006.01)
*A61M 5/168* (2006.01)
*B65D 83/48* (2006.01)
*A61M 5/155* (2006.01)
*A61M 5/44* (2006.01)
*A61M 5/145* (2006.01)
*A61M 5/142* (2006.01)
*A61M 39/24* (2006.01)

(52) U.S. Cl.
CPC ........ *A61M 5/155* (2013.01); *A61M 5/16804* (2013.01); *A61M 5/16881* (2013.01); *A61M 5/2053* (2013.01); *A61M 5/44* (2013.01); *A61M 39/22* (2013.01); *B65B 31/045* (2013.01); *B65B 51/26* (2013.01); *B65B 51/30* (2013.01); *B65D 83/48* (2013.01); *A61M 2005/14513* (2013.01); *A61M 2039/2486* (2013.01); *A61M 2207/00* (2013.01); *A61M 2207/10* (2013.01); *F04C 2270/0421* (2013.01); *Y10T 29/49* (2015.01); *Y10T 29/49808* (2015.01)

(56) References Cited

U.S. PATENT DOCUMENTS

| | | | | |
|---|---|---|---|---|
| 3,688,765 | A * | 9/1972 | Gasaway | A61M 5/30 124/71 |
| 3,977,401 | A | 8/1976 | Pike | |
| 4,031,889 | A * | 6/1977 | Pike | A61M 5/2053 604/144 |
| 4,680,027 | A * | 7/1987 | Parsons | A61M 5/34 604/68 |
| 4,769,974 | A | 9/1988 | Davis | |
| 4,894,054 | A * | 1/1990 | Miskinyar | A61M 5/14248 604/136 |
| 5,383,851 | A * | 1/1995 | McKinnon, Jr. | A61M 5/30 604/143 |
| 5,860,957 | A * | 1/1999 | Jacobsen | A61N 1/30 604/140 |
| 6,096,002 | A * | 8/2000 | Landau | A61M 5/30 604/143 |
| 6,210,359 | B1 * | 4/2001 | Patel | A61M 5/30 604/68 |
| 7,976,514 | B2 | 7/2011 | Abry et al. | |
| 2003/0233070 | A1 * | 12/2003 | De La Serna | F16K 17/30 604/141 |
| 2004/0073169 | A1 * | 4/2004 | Amisar | A61M 5/155 604/141 |
| 2005/0070848 | A1 * | 3/2005 | Kim | A61M 5/2053 604/140 |
| 2006/0052753 | A1 | 3/2006 | Mansouri | |
| 2010/0049125 | A1 * | 2/2010 | James | A61M 5/2033 604/110 |
| 2012/0217184 | A1 * | 8/2012 | Edwards | A61M 5/2033 206/571 |
| 2013/0317478 | A1 * | 11/2013 | Auld | A61M 5/2046 604/506 |

FOREIGN PATENT DOCUMENTS

| | | |
|---|---|---|
| EP | 2438945 A1 | 4/2012 |
| GB | 2390355 A | 1/2004 |
| JP | S4740308 Y1 | 12/1972 |
| JP | 2010502340 A | 1/2010 |
| WO | WO-2004/067067 A1 | 8/2004 |
| WO | WO-2005/075009 A1 | 8/2005 |
| WO | WO-2005/115529 A2 | 12/2005 |
| WO | WO-2006/021839 A1 | 3/2006 |
| WO | WO-2009/086250 A1 | 7/2009 |
| WO | WO-2011/050354 A1 | 4/2011 |
| WO | WO-2011/092536 A1 | 8/2011 |

OTHER PUBLICATIONS

Office Action, Chinese patent application No. 201380041558.8, dated Sep. 15, 2015.

International Search Report for International Application No. PCT/GB2013/051509, dated Aug. 29, 2013.

International Preliminary Report on Patentability and Written Opinion of International Searching Authority for International Application PCT/GB2013/051509, dated Dec. 9, 2014.

Japanese Office Action with Translation for Application No. 2015-515584, dated Mar. 17, 2017.

* cited by examiner

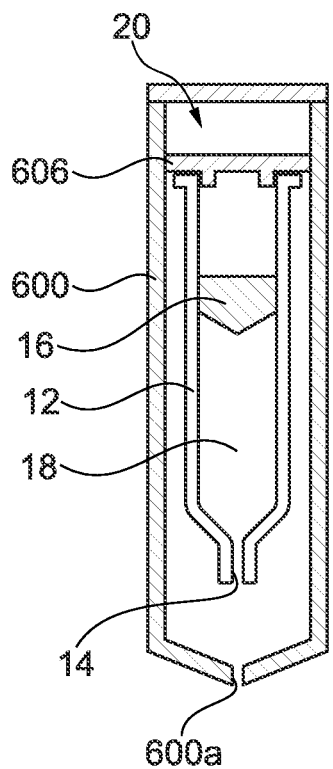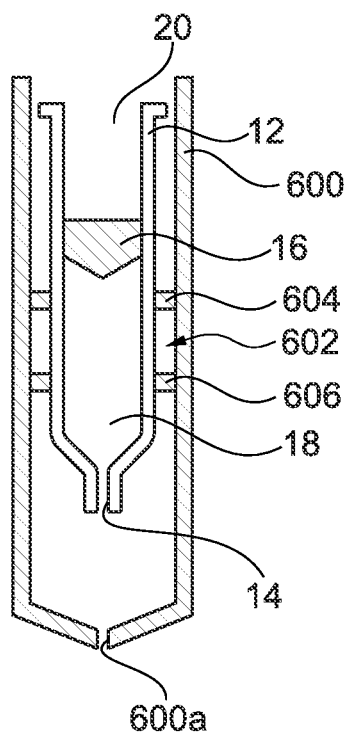
Fig. 14A    Fig. 14B
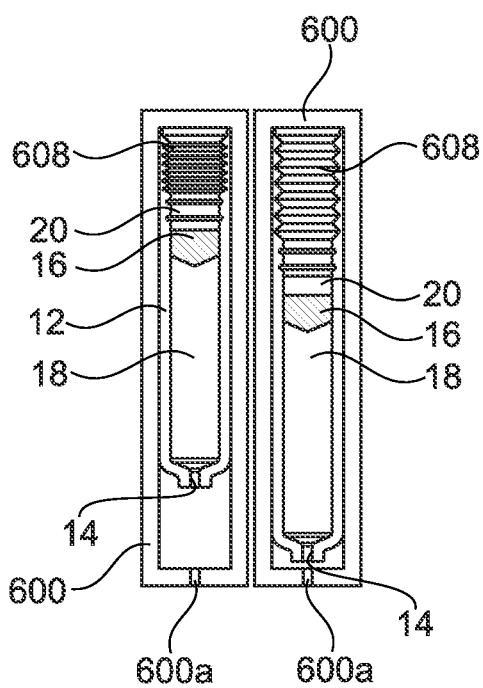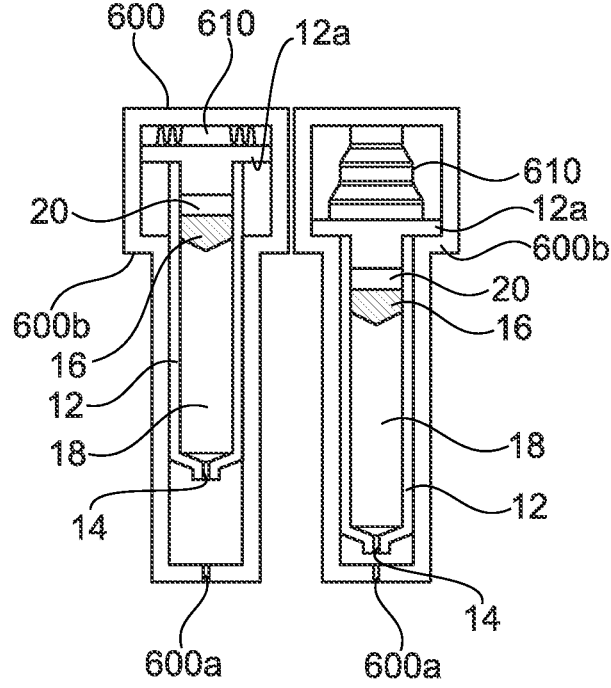
Fig. 15A  Fig. 15B    Fig. 16A  Fig. 16B

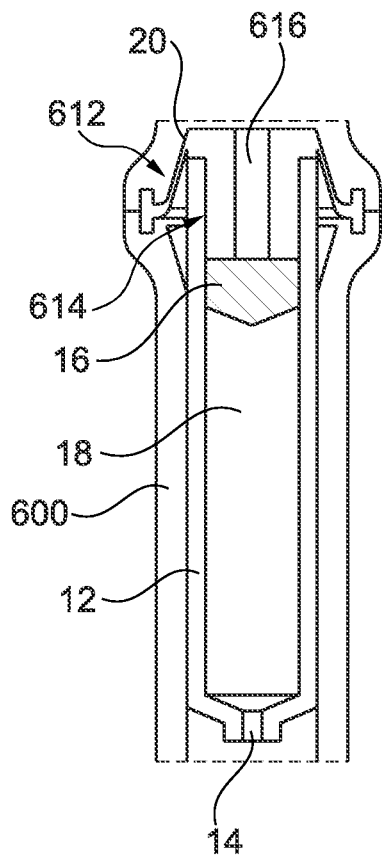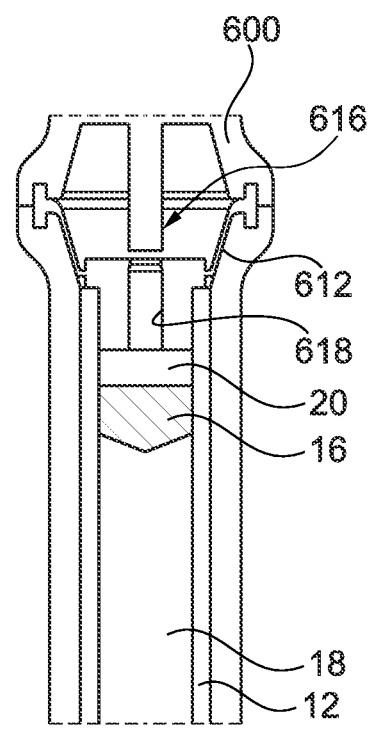
Fig. 17A  Fig. 17B
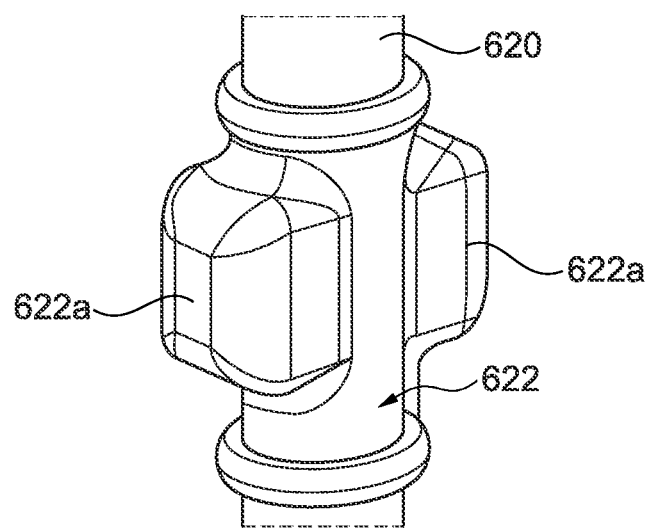
Fig. 18

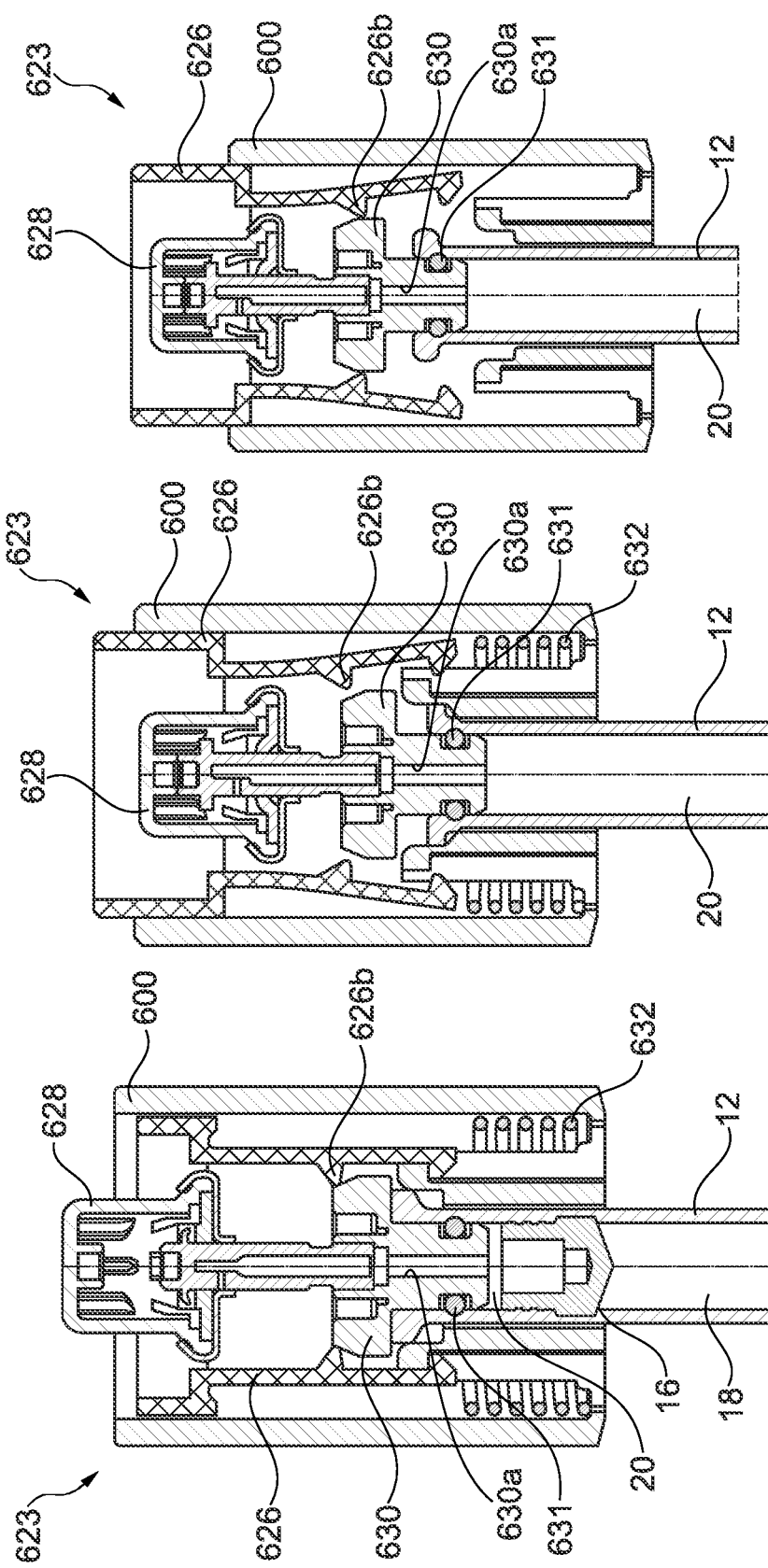

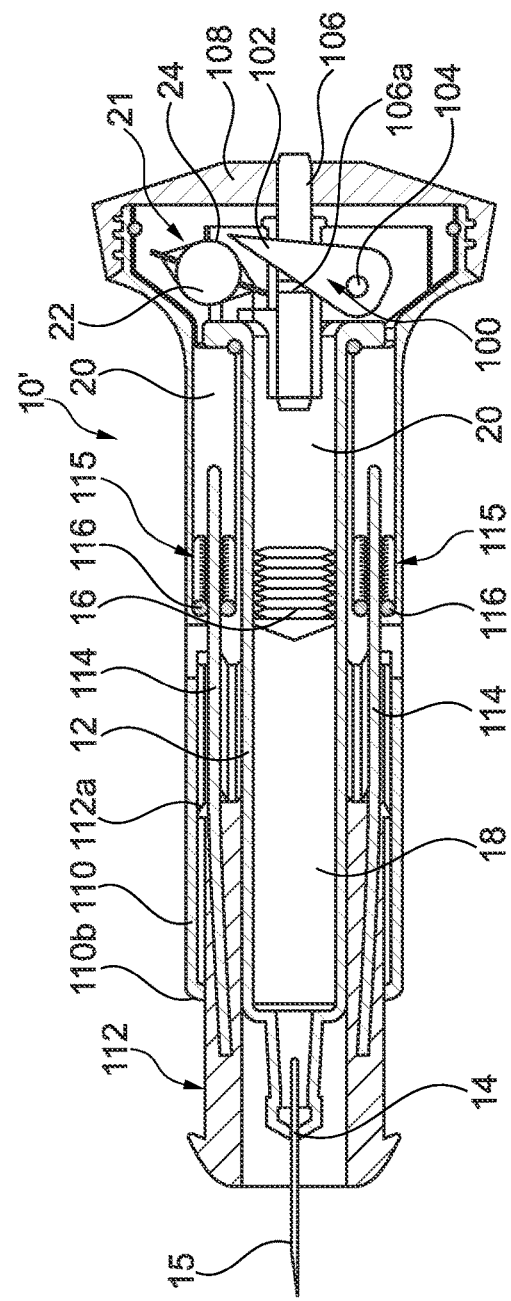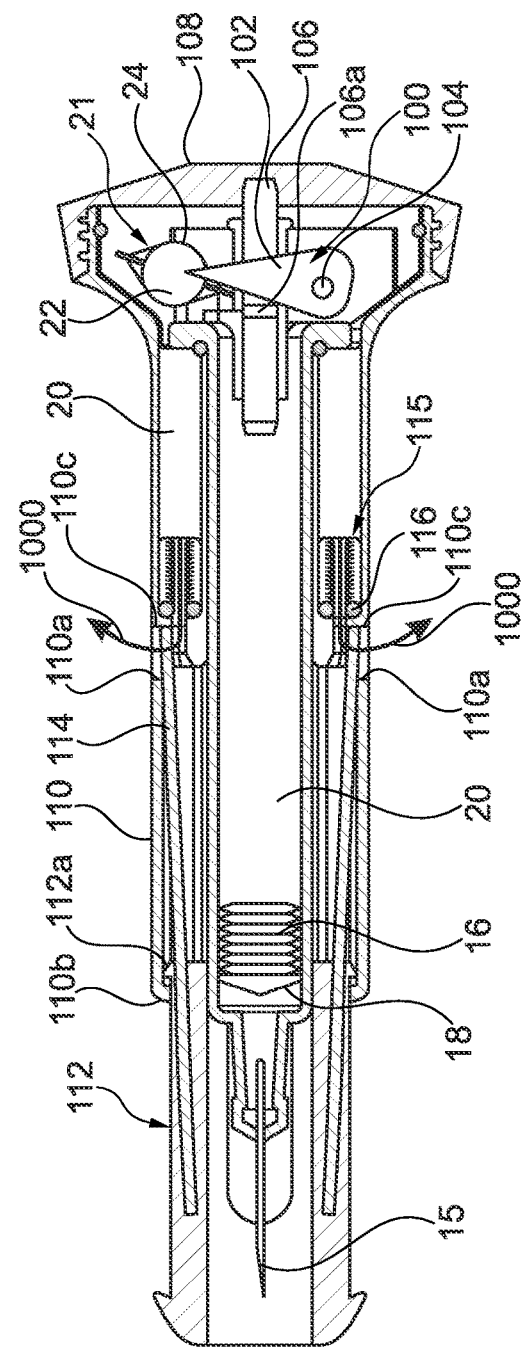

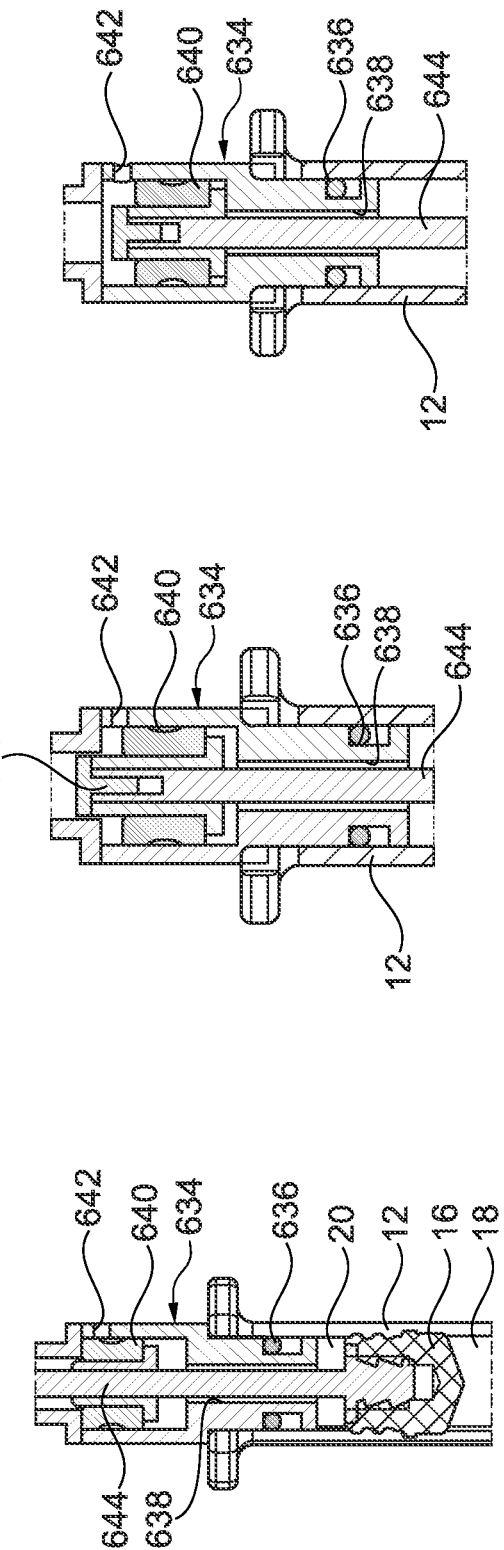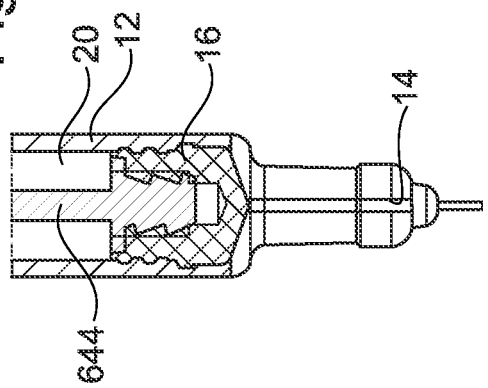

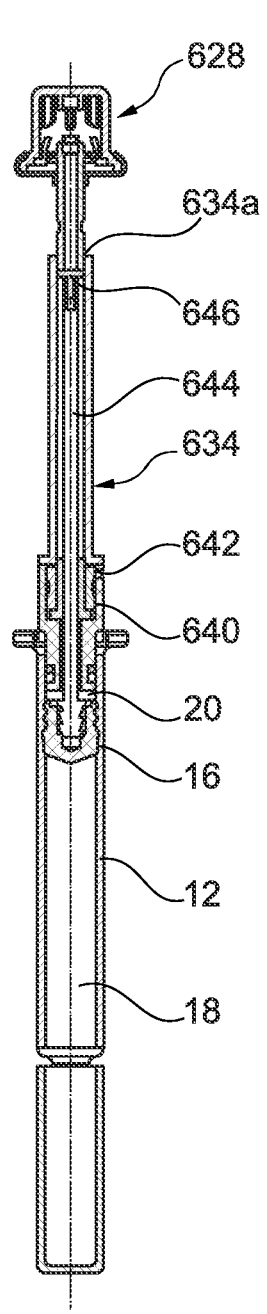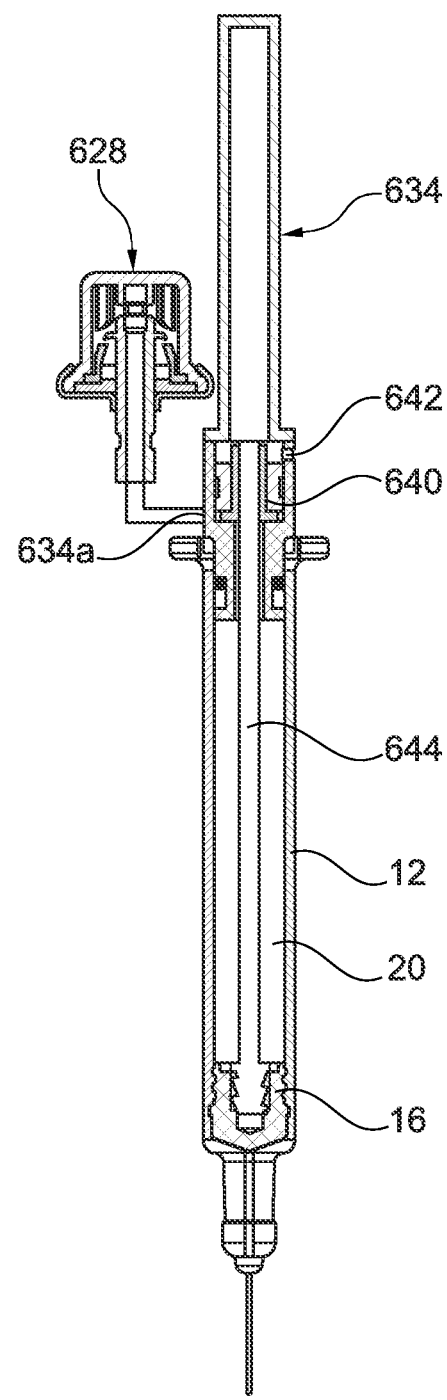
Fig. 24A
Fig. 24B

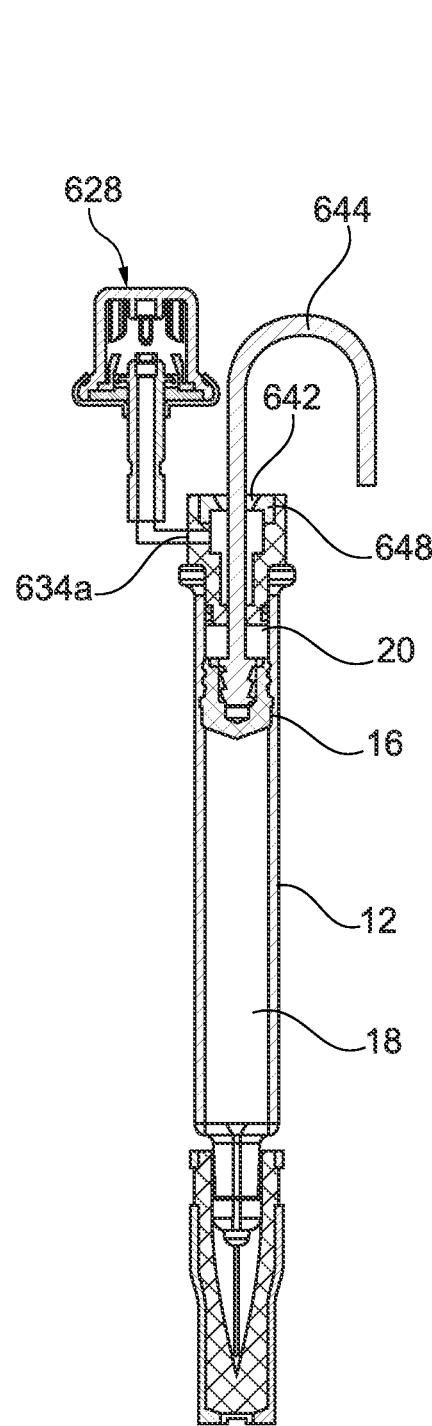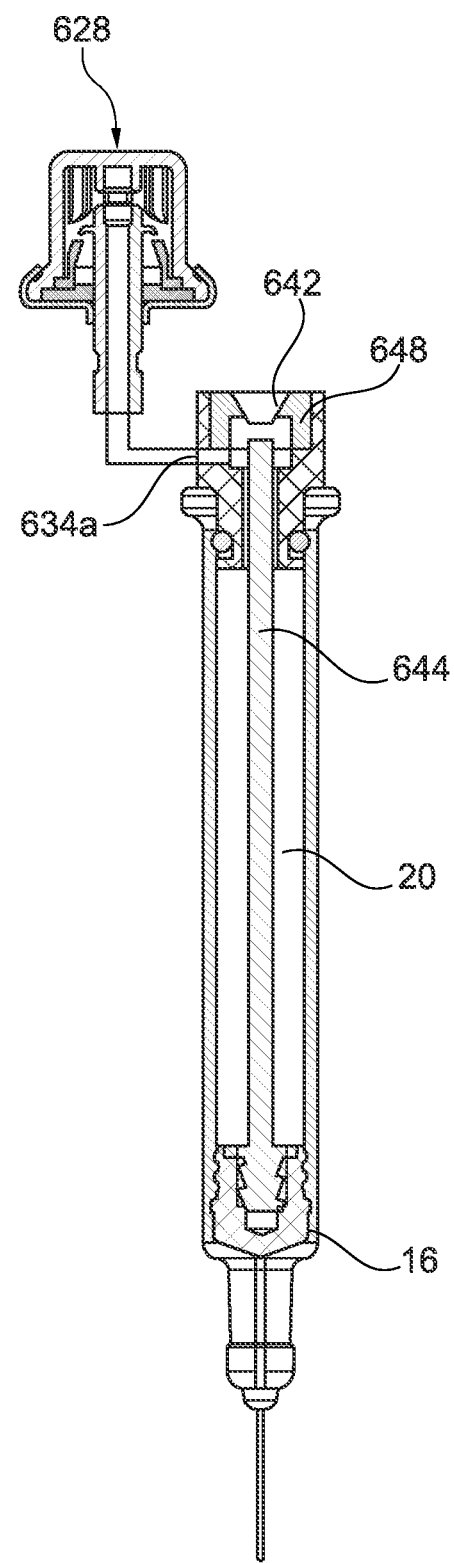
Fig. 35A
Fig. 35B

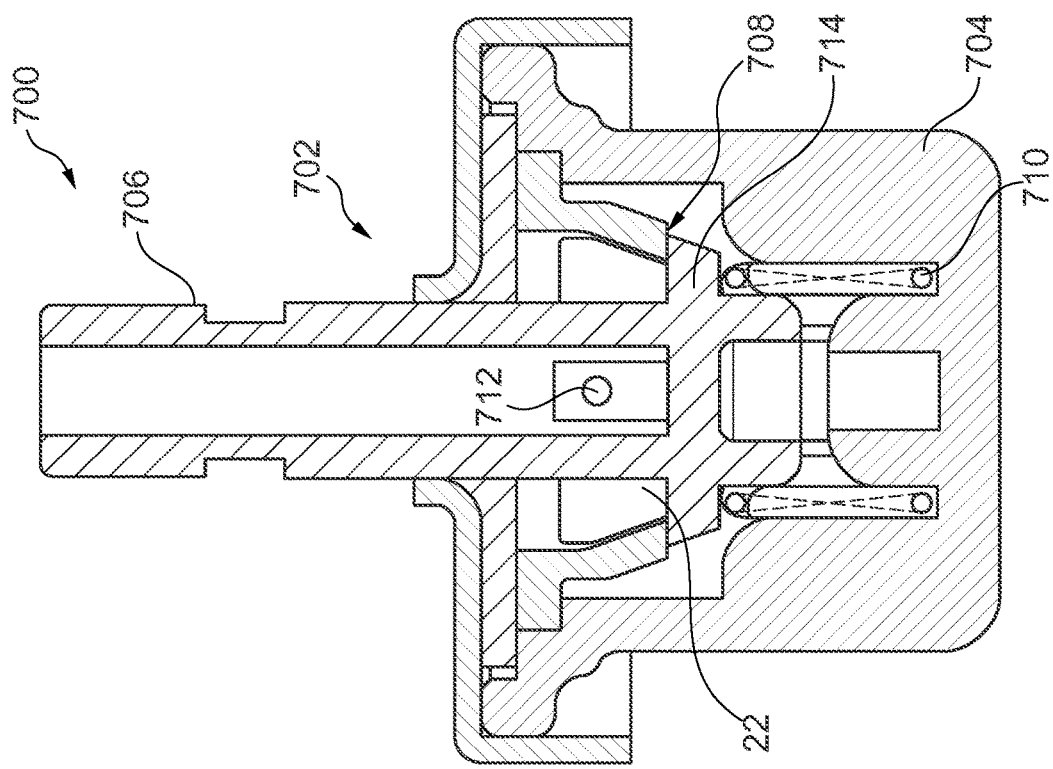
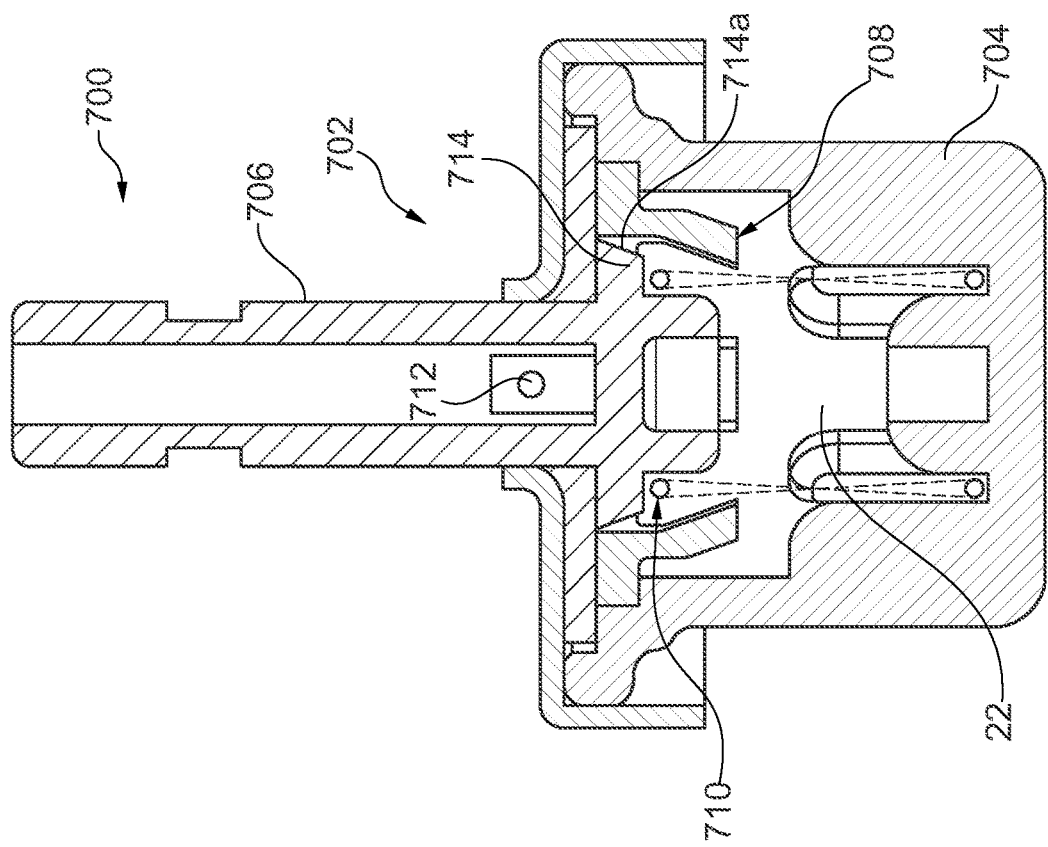

PROPELLANT POWERED SYRINGE WITH TRIGGER

CROSS REFERENCE TO RELATE APPLICATIONS

This application is a US national phase under 35 USC § 371 of International Application No. PCT/GB2013/051509, filed Jun. 7, 2013, which claims priority to United Kingdom patent application GB 1210082.2, filed Jun. 7, 2012. Priority application GB 1210082.2 is hereby incorporated by reference.

FIELD OF THE DISCLOSURE

This invention relates to a medical device, and in particular to a syringe for delivering a dose of medicament.

BACKGROUND

Automatically actuatable syringes are known and include a power source, such as a spring or a compressed gas to deliver a dose of medicament to a patient. Typically, a syringe has a barrel defining a chamber for containing a dose of medicament and a moveable stopper connected to a plunger rod for compressing the medicament to force it out of an opening in the barrel. In more complex devices, additional features are provided that are actuated in a sequence determined by the axial position of the plunger rod or the drive spring, for example. In such devices, the axial position of the plunger rod or the like is indicative of the stage of medicament delivery. Examples of such features include movement of the needle out of or into the device, and movement of a needle shroud between a needle-protecting and a needle-exposing position.

A self-contained pressurized injection device used for administering very viscous dermal filler material is described in WO-A-2009/086250 (Aesthetic Sciences Corporation). The described device includes an actuator assembly having a pressurized fluid container, a regulator and a bias member. The pressurized fluid container is configured to move between a first closed position and a second open position to selectively activate the device. The bias member biases the pressurized fluid container towards the first closed position.

US-A-2004/0073169 (Amisar et al.) describes a device for administering fluids intraveneously where liquefied gas contained in a container is allowed to evaporate in the container and exit the container as a vapour so as to provide a vapour pressure to a piston in the device and cause medicament to exit therefrom and be administered. In certain described embodiments, the container is provided with a heating element for maintaining the liquefied gas container at a constant temperature.

It is an object of certain embodiments of the present invention to provide a syringe device that is propellable by propellant that boils at a predetermined temperature that provides improved reliability and control in comparison to the prior art.

It is another object of certain embodiments of the present invention to provide a syringe device that is propellable by propellant that boils at a predetermined temperature that may be used in a sequenced autoinjector device.

BRIEF SUMMARY OF THE DISCLOSURE

The present invention is defined by the appended claims.

In accordance with a first aspect of the present invention there is provided a syringe propellable by propellant that boils at a predetermined temperature, the syringe comprising:
  a barrel having an outlet at a front end;
  a stopper axially moveable in the barrel;
  wherein the stopper defines and separates a first chamber and a second chamber, the first chamber being axially forwards of the stopper and being configured for containing a medicament, and the second chamber being axially rearwards of the stopper and being configured to receive propellant for acting on the stopper to move the stopper axially forwardly in the barrel to expel medicament through the outlet upon actuation of the syringe; and
  a third chamber for containing propellant;
  wherein the syringe is configured such that, in use, upon actuation of the syringe, liquid propellant is released from the third chamber and boils outside of the third chamber at or above the predetermined temperature to provide an increasing vapor pressure in the second chamber that causes the stopper to move axially forwardly and begin to expel medicament from the first chamber through the outlet;
  the syringe further comprising at least one trigger for triggering an action upon activation of the trigger, wherein the trigger is activated in response to the pressure in the second chamber satisfying a predetermined condition.

By releasing liquid propellant from the third chamber, the liquid propellant is able to vaporize utilizing heat from its surroundings. The propellant is a liquefied gas that, in the third chamber prior to rupturing, is in equilibrium between a liquid and a saturated vapor. Such an arrangement permits a more constant pressure to be maintained facilitating a reliable and controllable delivery and improves the reliability and predictability of further actions dependent on the pressure in the second chamber. Additionally, dispensing liquid from the third chamber provides greater flexibility to manipulate the rate of energy delivery to the second chamber.

In contrast, if the liquid propellant remained in the third chamber, it would rapidly cool as heat energy present is used to evaporate the liquid propellant. This cooling will result in a lower vapor pressure and may lead to such a reduction in temperature that further boiling of liquid propellant ceases. Clearly, such a situation is highly undesirable in a syringe since the failure to deliver a dose of medicament to a patient may have serious, if not fatal, consequences. In certain embodiments, the present invention seeks to minimize this risk without necessarily needing additional heating means thereby simplifying the overall complexity of the device and reducing the risk of component failure. Despite this, additional heating mean may be provided in alternative embodiments.

In the present invention, turbulence within the propellant can be promoted by permitting rapid boiling of the propellant through quick exposure of the propellant to atmospheric pressure (or another suitably different relative pressure). This turbulence facilitates the escape of liquid propellant from the third chamber. Additionally or alternatively, the centre of mass of the liquid propellant in the third chamber is preferably close to the opening to promote the escape of liquid propellant from the third chamber. One way of achieving this is to have the third chamber as full as possible with propellant.

The trigger may be a resistive moveable component and the predetermined condition is satisfied when the second chamber is in fluid communication with the resistive moveable component so that the pressure in the second chamber is acting on the resistive moveable component, and when the pressure in the second chamber is sufficiently high so as to be capable of moving the resistive moveable component.

The resistive moveable component may comprise a moveable piston that moves in response to an increase in pressure above a threshold pressure.

The resistive moveable component may comprise an expandable component that expands in response to an increase in pressure above a threshold pressure. The expandable component may comprise expandable bellows or may comprise an inflatable component.

The resistive moveable component may comprise a bi-stable diaphragm that is moveable between a first configuration and a second configuration in response to a pressure above a threshold pressure.

The resistive moveable component may be put in fluid communication with the second chamber when a fluid passageway is opened. The syringe may further comprise a sealing component that is moveable from a sealing position in which the fluid passageway is closed and an open position in which the fluid passageway is open. The sealing component may be moveable from the sealing position to the open position due to pressure in the second chamber. The sealing component may comprise a valve that opens at a valve threshold pressure. The sealing component may be moveable from the sealing position to the open position in response to a user action.

In one embodiment, the predetermined condition may be satisfied when the pressure in the second chamber drops below a predetermined threshold. The trigger may be a biasing member acting against the pressure of the second chamber, and when the pressure in the second chamber drops below the predetermined threshold the biasing member exerts a force greater than the force exerted by the pressure in the second chamber. The pressure in the second chamber may drop to satisfy the predetermined condition in response to venting of gaseous propellant from the second chamber. The stopper may be axially moveable in the barrel between:
 a first position in which the vent hole is not in fluid communication with the first chamber or the second chamber; and
 a second position axially forward of the first position in which the vent hole is in fluid communication with the second chamber thereby permitting venting of propellant from the second chamber.

In one embodiment, in the first position the stopper blocks fluid communication between the vent hole and the first chamber and between the vent hole and the second chamber, and in the second position the stopper is axially forward of at least part of the vent hole such that the vent hole is in fluid communication with the second chamber. The stopper may comprise a bung and a piston extending axially rearwardly from the bung, wherein each of the bung and the piston seals to the barrel, the piston being configured to be acted upon by vapor pressure in the second chamber so as to cause the stopper to move axially in the barrel. The stopper may include a rearwardly axially extending rod that, in the first position, extends through the vent hole and seals to the vent hole so as to block fluid communication between the vent hole and the first chamber and between the vent hole and the second chamber, and, in the second position, the rod does not extend through the vent hole so that the vent hole is in fluid communication with the second chamber. The vent hole may comprise a seal for sealing against the rod.

In one embodiment, the syringe may further comprise a blocking member that is moveable between a blocking position in which fluid communication between the vent hole and the second chamber is blocked by the blocking member, and a non-blocking position in which the vent hole is in fluid communication with the second chamber;
 wherein the blocking member is moveable between the blocking position and the non-blocking position by the stopper such that in the first position the blocking member is in the blocking position and in the second position the blocking member is in the non-blocking position.

The stopper may be selectively engageable with the blocking member such that when the stopper is not engaged with the blocking member, the stopper is forwardly axially moveable relative to the blocking member, and when the stopper is engaged with the blocking member forward axial movement of the stopper causes forward axial movement of the blocking member towards the non-blocking position.

The stopper may include a rearwardly axially extending rod extending through blocking member where the rod includes a radial projection at a rear end thereof, wherein the stopper is able to move relative to the blocking member until the projection contacts the blocking member to engage the stopper to the blocking member.

The stopper may include a bung and an extendible member that is connected to the blocking member and the bung, wherein the extendible member is able to extend in axial length and permit forward axial movement of the bung relative to the blocking member until the extendible member reaches a maximum axial extension due to the relative axial distance between the bung and the blocking member causing the stopper to engage with the blocking member.

The extendible member may be a coil or a flexible tether which may be string.

In one embodiment, upon actuation of the syringe the vent hole is in fluid communication with the second chamber such that propellant may vent from the second chamber, where the rate of venting through the vent hole is insufficient to prevent the vapor pressure in the second chamber rising sufficiently to cause the stopper to move axially forwardly in the barrel. The stopper may include an occlusion member that, in at least one axial position of the stopper in the barrel, occludes the vent hole so as to limit the rate of venting therethrough without preventing venting entirely. The occlusion member may not occlude the vent hole when the stopper is in its forwardmost possible position in the syringe barrel in which the first chamber has substantially zero volume and substantially all medicament has been expelled from the first chamber.

The vent hole may be elongate such that the occlusion member may occlude the vent hole along the elongate length of the vent hole.

The third chamber may initially contain a sufficient volume of propellant to move the stopper to its forwardmost possible position in the barrel in which the first chamber has substantially zero volume and substantially all medicament has been expelled from the first chamber.

The vent hole may be formed in the barrel.

The syringe may further comprise a propellant housing sealed to the barrel, and the vent hole may be formed in the propellant housing.

The propellant may vent away from the second chamber to the outside environment through the vent hole.

The propellant may vent away to a further chamber from the second chamber through the vent hole, where the further chamber has a lower pressure than the second chamber.

The trigger may be a moveable component that moves when the predetermined condition is satisfied, and the predetermined condition is satisfied when the pressure in the second chamber relative to the pressure in a reference chamber substantially equals a predetermined ratio. The predetermined ration may be 1:1.

In any embodiment, the moveable component may be moveable so as to permit venting of gaseous propellant from the second chamber. The moveable component may be moveable so as to open a valve. The moveable component may be moveable so as to move a further component.

The syringe may further comprise a needle shield moveable between a first position in which the needle is exposed and a second position in which the needle is substantially covered by the needle shield such that the needle is not exposed, wherein the action includes the movement of the needle shield between the first position and the second position.

The syringe may form part of an autoinjector device in which the syringe is moveable relative to a housing of the autoinjector device between a first position in which the needle is within the housing and is not exposed and a second position in which the needle extends out of the housing, and wherein the action includes movement of the syringe between the first position and the second position. The action may include movement of the syringe from the first position to the second position. The action may include movement of the syringe from the second position to the first position.

The syringe may have one or more indicators for signalling to the user that an injection sequence is at a particular stage, and wherein the action includes activating the one or more indicators to produce the signal. The one or more indicators may include a visual indicator which may be an LED. The one or more indicators include an audible indicator which may be a speaker or a whistle, for example. The one or more indicators may signal the end of delivery of medicament. The one or more indicators may signal that a predetermined time period has elapsed since the end of delivery of medicament.

The predetermined condition may be exceeding a predetermined pressure. The predetermined condition may be exceeding the predetermined pressure after a predetermined time period has elapsed or subsequent to a prior predetermined condition being satisfied. The predetermined condition may be falling below a predetermined pressure. The predetermined condition may be falling below the predetermined pressure after a predetermined time period has elapsed or subsequent to a prior predetermined condition being satisfied.

The predetermined temperature may be ambient temperature.

The predetermined temperature may be between 15° C. and 30° C., and may be between 20° C. and 25° C.

The predetermined temperature is greater than ambient temperature.

The third chamber may comprise a dispenser for providing propellant to the second chamber, wherein the dispenser is moveable from a closed position in which propellant cannot exit the dispenser to an open position in which a predetermined volume of propellant can exit the dispenser. The dispenser may have a capacity for containing propellant, and the predetermined volume is less than the capacity. The capacity may be defined by a first internal volume of the dispenser, and the predetermined volume is defined by a second internal volume of the dispenser, and wherein in the closed position, the first internal volume is fluidly connected to the second internal volume so as to allow propellant to fill the second internal volume, and in the open position, the first internal volume is not fluidly connected to the second internal volume and the second internal volume is fluidly connected to the second chamber so as to allow the predetermined volume of propellant to be provided to the second chamber.

The third chamber may be rupturable, and the syringe further comprises a rupturing portion, wherein the rupturing portion is configured to rupture the third chamber upon actuation of the syringe to fluidly connect the third chamber to the second chamber. The third chamber may comprise a flexible rupturable container for containing propellant.

Alternatively, the rupturing portion may comprise a valve having a valve body, valve stem, and a locking member, where the valve stem is slidably moveable relative to the valve body between:
  i) a non-dispensing position in which an outlet port of the valve stem is out of fluid communication with the third chamber; and
  ii) a dispensing position in which the outlet port is in fluid communication with the third chamber so as to permit transfer of propellant from the third chamber through the valve stem;
wherein the locking member is configured to prevent return of the valve stem into the non-dispensing position once the valve stem slides beyond a locking position; and wherein the third chamber is ruptured when the valve stem is in the dispensing position and beyond the locking position.

The locking member and the valve stem may comprise inter-engaging members, wherein the inter-engaging members:
  a) contact one another during movement of the valve stem towards the dispensing position and permit movement of the valve stem into the dispensing position; and
  b) contact one another during attempted movement of the valve stem from beyond the locking position back towards the dispensing position and prevent movement of the valve stem back into the non-dispensing position. The inter-engaging members may contact one another during movement of the valve stem towards the dispensing position and permit movement of the valve stem into the dispensing position by flexing or other distortion of at least one of the inter-engaging members.

The inter-engaging member of the valve stem may comprise a flange. A distal edge of the flange may be angled to promote flexing of the locking member during movement of the valve stem into the dispensing position. The inter-engaging member of the locking member may comprise at least one flexible latch. The at least one flexible latch may exhibits elastic behaviour. The locking position of the valve stem may be defined as a point where the inter-engaging member of the valve stem slides beyond, and disengages from, the inter-engaging member of the locking member. The valve may further comprise a biasing member for biasing the valve stem into the non-dispensing position. The biasing member may be a compression spring.

The third chamber may contain a volume of liquid propellant such that liquid propellant remains present in the syringe when the stopper reaches its forwardmost axial position in the syringe barrel.

All non-mutually exclusive combinations of features disclosed in the present application are within the scope of the present invention.

BRIEF DESCRIPTION OF THE DRAWINGS

Embodiments of the invention are further described hereinafter with reference to the accompanying drawings, in which:

FIG. 15A shows the dispenser in a closed position and FIG. 15B shows the dispenser in an open position.

FIG. 14A shows an embodiment of the present invention that includes a trigger in the form of a moveable piston that is activated in response to the pressure in the second chamber satisfying a predetermined condition;

FIG. 14B shows an alternative embodiment in accordance with the present invention includes a trigger in the form of a moveable piston;

FIGS. 15A and 15B show an alternative embodiment of the present invention that includes a trigger in the form of expandable bellows;

FIGS. 16A and 16B show an alternative embodiment of the present invention that includes a trigger in the form of expandable bellows;

FIGS. 17A and 17B show an alternative embodiment of the present invention that includes a trigger in the form of a bi-stable diaphragm;

FIG. 18 shows an alternative embodiment of the present invention that includes a trigger in the form of an inflatable sleeve;

FIGS. 19A to 19C show an alternative embodiment of the present invention that includes a trigger in the form of a moveable piston;

FIGS. 20 and 21 show a syringe in accordance with an embodiment of the present invention that includes a moveable needle shield and a trigger in the form of legs for moving the needle shield;

FIG. 22A shows a partial cross section of a syringe in accordance with an embodiment of the present invention that includes a vent hole, where, in FIG. 22A, the vent hole is closed;

FIG. 22B shows the syringe of FIG. 22A with the vent hole partially open;

FIG. 22C shows the axial position of the stopper that corresponds to the configuration shown in FIG. 22B;

FIG. 22D shows the syringe of FIGS. 22A and 22B with the vent hole fully open;

FIG. 22E shows the axial position of the stopper that corresponds to the configuration shown in FIG. 22D;

FIG. 24A show a syringe in accordance with an embodiment of the present invention that includes a vent hole;

FIG. 24B shows a syringe in accordance with an alternative embodiment of the present invention that includes a vent hole;

FIGS. 35A and 35B show a syringe in accordance with an alternative embodiment of the present invention that includes a vent hole, where in FIG. 35A the vent hole is closed, and in FIG. 35B the vent hole is open;

FIG. 36A is a cross-sectional view of a propellant dispenser in accordance with an embodiment of the present disclosure; and FIG. 36B is a cross-sectional view of a propellant dispenser in accordance with an embodiment of the present disclosure.

DETAILED DESCRIPTION

Figure 1A:
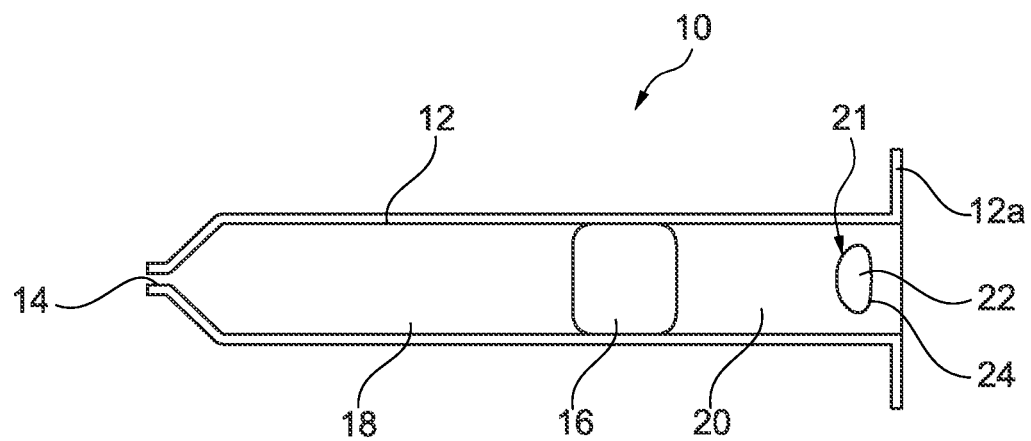
FIG. 1A is a schematic cross sectional view of a syringe according to an embodiment of the present invention comprising a self-contained rupturable container of propellant.

A syringe 10 according to an embodiment of the present invention is shown in FIG. 1A. The syringe 10 has a barrel 12 having an outlet 14 at a forward end and a stopper 16 disposed in the barrel 12. The stopper 16 is axially moveable within the barrel 12 when subjected to a sufficient axial force. The barrel 12 has a finger flange 12a at a rear end, however some syringes within the scope of the present invention may not comprises finger flanges. The stopper 16 defines and separates a first chamber 18 and a second chamber 20 where the first chamber 18 is axially forwards of the stopper 16 and is configured for containing a substance such as a medicament, and in particular, a liquid medicament. Hereinafter, the first chamber 18 will be considered to be initially containing medicament, although the skilled person will appreciate that other alternative substances may be present. The second chamber 20 is axially rearwards of the stopper 16 and is configured to receive propellant from a propellant source. In the syringe of FIG. 1A, the propellant source is a container 21 which comprises a rupturable wall 24 defining a third chamber 22 containing propellant.

The syringe 10 additionally has a rupturing portion (not shown) configured to rupture the rupturable wall 24 to irreversibly fluidly connect the third chamber 22 and the second chamber 20 so that propellant enters the second chamber 20. That is, the rupturable wall 24 is frangible or breakable such that once it has been broken or opened, it cannot be reclosed or resealed without additional means for doing such. The rupturable wall 24 is preferably flexible at least in part so that the shape of the container 21 is changeable.

Figure 4:
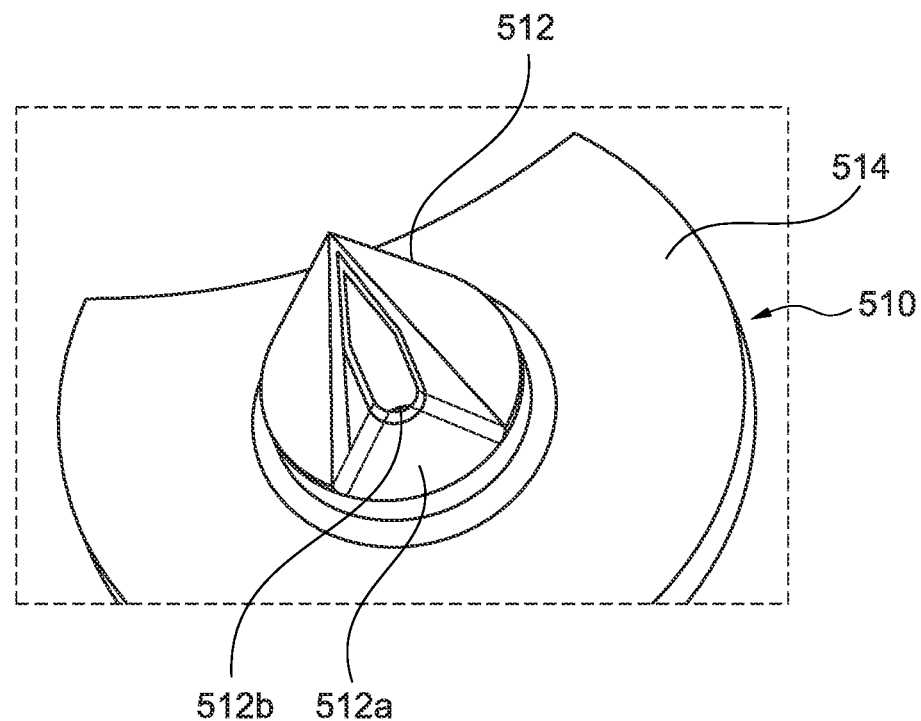
FIG. 4 shows a rupturing portion in accordance with an embodiment of the present invention.

Within the scope of the present invention, once a fluid connection is established between the third chamber 22 and the second chamber 20, the fluid connection is maintained and not closed or sealed. This is necessary for the desired thermodynamic properties of the syringe 10 in accordance with the present invention, as is described in more detail below. Depending on the nature of the third chamber 22, the rupturing portion may be a needle or other suitable element configured to slice, rupture, break, pierce or otherwise create an opening in the rupturable wall 24 (or, in other embodiments, a similar rupturable element defining at least a part of the third chamber 22) and establish a fluid connection between the third chamber 22 and the second chamber 20. In the case where the rupturing portion is a needle or similar piercing element, it is preferable that it is either hooked, or hollow in configuration or otherwise shaped so that upon rupturing, breaking, or piercing the rupturable wall 24, the rupturing portion itself does not entirely block the newly formed fluid passageway between the third chamber 22 and the second chamber 20. In the case where the rupturing portion has a hollow configuration, the propellant may flow through the hollow portion from the third chamber 22 to the second chamber 20. In other embodiments, the rupturing portion may comprise apparatus for rupturing the rupturable wall 24 by a bursting mechanism. That is, the rupturing portion acts to exert a force on the container 21 so that that the pressure in the third chamber 22 increases so that the rupturable wall 24 is caused to rupture, thereby establishing a fluid connection between the third chamber 22 and the second chamber 20. In some embodiments, the rupturing portion may be moved towards the third chamber 22 to rupture the third chamber 22. In other embodiments, the third chamber 22 may be moved towards the rupturing portion to cause rupturing of the third chamber 22. FIG. 4 shows an example of a rupturing portion 510 in accordance with an embodiment of the present invention for establishing a permanent fluid connection between the third chamber 22 and the second chamber 20. The rupturing portion 510 includes a conical element 512 that has a cut-out portion 512a and a bore 512b running therethrough. The conical element 512 projects from a base 514 through which the bore 512b passes. In use, the conical element 512 pierces a hole in a rupturable wall of the third chamber 22 requiring only a relatively low force to establish a fluid connection between the third chamber 22 and the second chamber 20 via the bore 512b. The tapered profile of the conical element 512 means that as the rupturing portion 510 is advanced further towards the rupturable wall, the conical element 512 will enlarge the hole created and ensure that the fluid path between the third chamber 22 and second chamber 20 is not obstructed. The cut-out portion 512a ensures that the hole is created effectively and minimizes the risk of the rupturing portion 510 itself sealing the hole it creates. Fluid egress from the third chamber 22 is therefore maximized. The presence of the bore 512b facilitates direct and efficient passage of both liquid and gaseous propellant between the third chamber 22 and second chamber 20.

Figure 5:
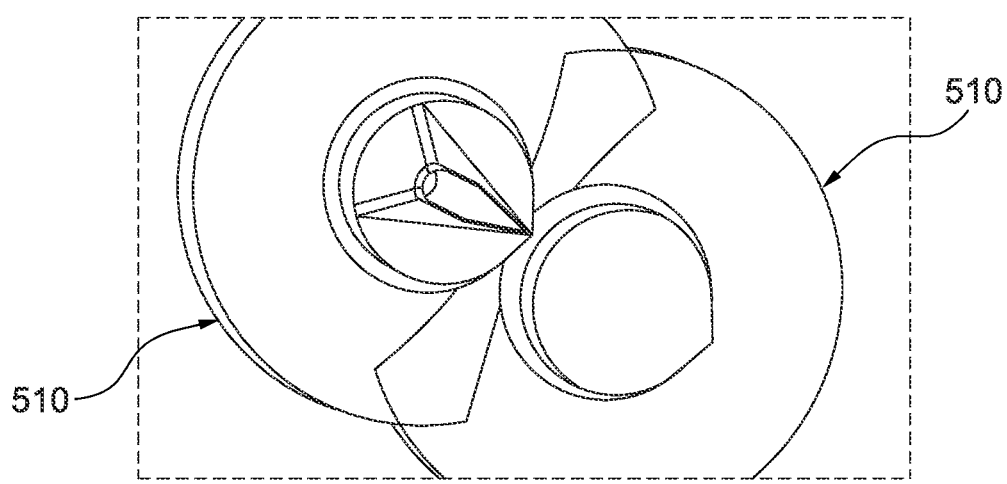
FIG. 5 shows an alternative rupturing portion in accordance with an embodiment of the present invention.

The rupturing portion 510 may be shaped (e.g. the shape of the base 514) so that multiple rupturing portions can be arranged in close proximity to act on the same rupturable wall. As an example, FIG. 5 shows two identical rupturing portions 510 in suitably close arrangement for acting on a single rupturable wall. The use of multiple rupturing portions (in general) will facilitate greater transfer of fluid from the third chamber 22 to the second chamber 20. The one or more rupturing portions may rupture the third chamber 22 from any direction and in any orientation. Depending on the specific syringe, it may be preferable to rupture the third chamber 22 at a particular point or in a particular direction to maximize or otherwise control the release of propellant from the third chamber 22.

Other non-conical but tapered elements may be used to form the rupturing portion of the present invention. In such cases, it is still preferable for the tapered element to include a cut-out portion to improve fluid flow and minimize the risk of the rupturing element sealing newly created hole in the rupturable wall. Additionally or alternatively, it is preferable for the rupturing portion to include a through-bore for channeling fluid from the third chamber 22 to the second chamber 20.

The propellant is one that boils at a predetermined temperature which in all cases must be below the local operating temperature of the system during use. A particularly preferable propellant is or includes a hydrofluoroalkane (HFA) as this provides a suitable pressure for use with aqueous solution in a fine bore needle syringe. HFA 134a boils at $-26.4°$ C. which is able to provide sufficient pressure even when the medicament that is to be delivered is chilled. In other embodiments a propellant may have a lower boiling point which provides an increased pressure is use, which is especially useful for the delivery of highly viscous drugs. For example HFA 422d has a boiling point between $-46.2°$ C. and $-41.5°$ C. Similarly, HFA 507c has a boiling point of $-46.9°$ C. In alternative embodiments, the propellant may boil at a higher temperature such that it cannot generate sufficient pressure to drive the medicament without additional energy from an external source such as the patient or another heat source. For example HFA 123 boils at $+27.9°$ C. Similarly, HFA 245fa has a boiling point of $+15.3°$ C.

When the third chamber 22 is in fluid communication with the second chamber 20, propellant is released into the second chamber 20. At the predetermined temperature, the propellant released into the second chamber 20 is initially in its liquid phase. Some of the propellant will initially be in its liquid phase due to the confines of the volume in which it resides, even if the propellant is at a temperature above the predetermined temperature.

Some of this liquid propellant will evaporate due to the heat that the propellant is exposed to (e.g. ambient heat), thereby providing gas phase propellant to the second chamber 20. Since the vaporization of propellant requires the absorption of latent heat from the liquid propellant, the process of evaporation cools the remaining liquid propellant. This cooling results in the vapor pressure immediately above the liquid propellant being lower than it is at its initial starting (i.e. ambient) temperature. Nevertheless, the pressure in the second chamber 20 begins to increase enough so that the stopper 16 moves axially forwardly in the barrel 12, thereby reducing the volume of the first chamber 18 and pressurizing the medicament held therein. The pressurized medicament exits the barrel 12 through the outlet 14, which may be fluidly connected to a needle or other applicator, for entry into an injection site such as subcutaneous tissue.

In the case where a propellant is used that boils at a temperature higher than ambient temperature, the ambient temperature will not be sufficient to boil the propellant and thus the stopper 16 will not move as a consequence. In these embodiments, an additional heat source must be provided to boil the propellant and begin movement of the stopper 16. For example, the heat source could be the user's hand which will be at "body temperature" (approximately $37°$ C., or $33°$ C. at the surface of the skin). This arrangement may reduce the risk of accidental delivery of medicament if the propellant is inadvertently in fluid communication with the second chamber 20.

As the stopper 16 moves axially forwards towards the outlet 14 to reduce the volume of the first chamber 18, the second chamber 20 is made larger. Thus, additional volume is continuously created in the second chamber 20 into which the propellant can evaporate into. This further vaporization causes further cooling of the remaining liquid propellant and thus further reduces the observed vapor pressure in the second chamber 20.

However, the system is not completely adiabatic (nor is it isothermal) so thermal energy is absorbed by the liquid propellant from its immediate environment (e.g. the barrel 12) to counter the reduction in temperature of the liquid propellant and the reduction in vapor pressure in the second chamber 20. Indeed, in the absence of this heat absorption, the propellant would freeze or at least become a stable liquid as the temperature of the liquid propellant continues to drop, and the syringe 10 would cease to operate correctly. This drop in vapor pressure in the second chamber 20 is exhibited throughout delivery of the medicament from the first chamber 18. In particular, since the stopper 16 is moving, the propellant in the second chamber 20 is continuously exposed to "new" sections of the inside of the barrel 12. Since the "new" sections of the inside of the barrel have not previously been in contact with the propellant, its thermal energy will initially be substantially at or near to ambient temperature or a higher temperature if additional heating means are present (unlike the sections of the barrel 12 axially rearward thereof which have already given up thermal energy to the liquid propellant). The "new" sections of barrel that the propellant is exposed to during delivery therefore act as a fresh heat source which is able to provide thermal energy to the propellant in the second chamber 20.

The stopper 16 continues to move axially forwardly in the barrel 12 until it reaches the forwardmost end of the barrel 12 where further forward axial movement is not possible. At this point, the full dose of medicament in the first chamber 18 has been delivered and the first chamber 18 has been reduced to its smallest volume (i.e. at or near substantially zero, depending on the formation of the front end of the barrel 12). With no further movement of the stopper 16, the temperature of the gas phase propellant, and any remaining liquid propellant, begins to increase as thermal energy is absorbed from the environment. Since, with the stopper 16 stationary in the barrel 12, the second chamber 20 has a constant volume, the increase in temperature of the propellant results in an increase in vapor pressure in the second chamber 20. This increase in vapor pressure tends towards the vapor pressure of the propellant at the temperature of its immediate environment (e.g. ambient temperature or a higher temperature if additional heating means are still present at this point). Indeed, the vapor pressure in the second chamber 20 will reach the vapor pressure of the propellant at the temperature of its immediate environment given long enough as equilibrium is reached.

The magnitude of the drop in vapor pressure in the second chamber 20 during delivery from the initial vapor pressure maximum when the propellant is released into the second chamber 20 to when the stopper 16 has reached the front end of the barrel 12 depends on any one or more of i) the thermal properties of the syringe 10, ii) the rate of delivery of propellant into the second chamber 20, and iii) the phase of the propellant entering the second chamber 20 (as will be described in more detail below). With regards to the effects of the thermal properties of the syringe 10, such properties determine the rate of heat transfer into the propellant in the second chamber 20. Similarly, the rate and phase of propellant entering the second chamber 20 affects the thermodynamic processes occurring during delivery with regards to the propellant in the second chamber 20.

As an example, a 0.5 bar drop in vapor pressure may be exhibited when delivering 1 ml of aqueous solution through a 27 gauge needle attached to the outlet 14 measured from the initial vapor pressure maximum when the propellant is released into the second chamber 20 to when the stopper 16 has reached the front end of the barrel 12.

Figure 6A:
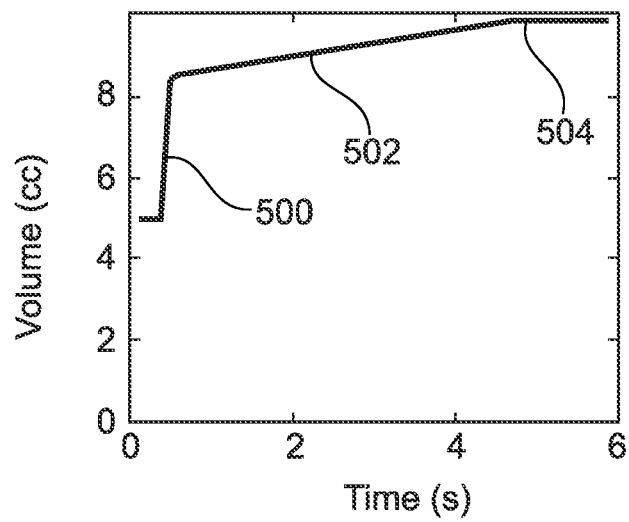
FIG. 6A shows a time-dependent gas volume profile of a compressed gas powered syringe in accordance with the prior art where the compressed gas reservoir is large relative to the internal volume of the system.

The advantages of liquefied gas powered syringes are best understood by comparison with a syringe powered by a compressed gas. In some known prior art compressed gas syringes, compressed gas is released from a reservoir into a volume behind a stopper in a syringe barrel where the expanding volume of gas can act on the stopper and cause it to move and expel medicament from the barrel. FIG. 6A shows a time-dependent volume profile of a compressed gas syringe in accordance with the prior art. 5 cc of compressed gas is initially contained in a reservoir which is in selective fluid communication with a volume of the syringe rearward of a stopper. As shown in FIG. 6A, when the reservoir is opened the compressed gas expands rapidly at 500 as the compressed gas fills the dead volume behind the stopper.

There is a constant mass of gas which follows the ideal gas law under adiabatic conditions and behaves as PV=nRT, where P is the pressure of the gas, V is the volume of the gas, n is the number of moles of gas, T is the temperature of the gas and R is the universal gas constant. Once the dead volume is filled with compressed gas, the expanding gas begins to gas the stopper to move, as indicated at 502 on FIG. 6A, and medicament is expelled from the barrel. Once the stopper reaches its forwardmost position in the barrel, the compressed gas ceases to expand further, as indicated at 504 of FIG. 6A.

Figure 6B:
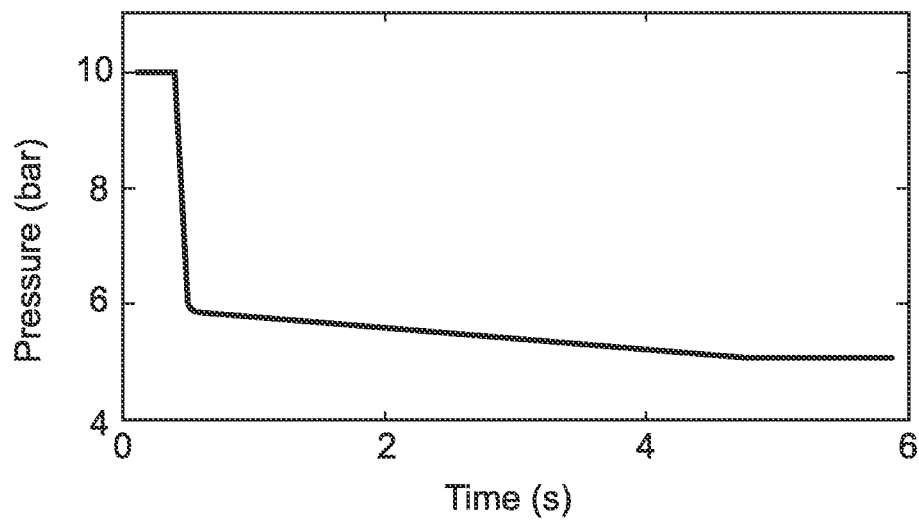
FIG. 6B shows the corresponding time-dependent pressure profile.

Since the quantity nRT is constant for adiabatic expansion, the pressure of the gas drops as the volume increases. This is shown in FIG. 6B which shows a time-dependent pressure profile corresponding to the volume profile of FIG. 6A. This drop in pressure occurs both as the compressed gas enters the dead volume (i.e. when the compressed gas reservoir is initially opened) and during the time that the stopper is moving forwards and expelling medicament. As shown in FIG. 6B, the result is an initially steep drop in pressure, followed by a more gradual drop in pressure. The final pressure of the compressed gas is determined by the volume in which it resides at the end of the delivery, when the stopper is at its forwardmost position in the barrel. FIGS. 6A and 6B relate to a syringe where the reservoir of compressed gas is large relative to the internal volume of the system. As a consequence of this, the final pressure of compressed gas is maintained at a relatively high level (~5 bar from an initial 10 bar).

Figure 7A:
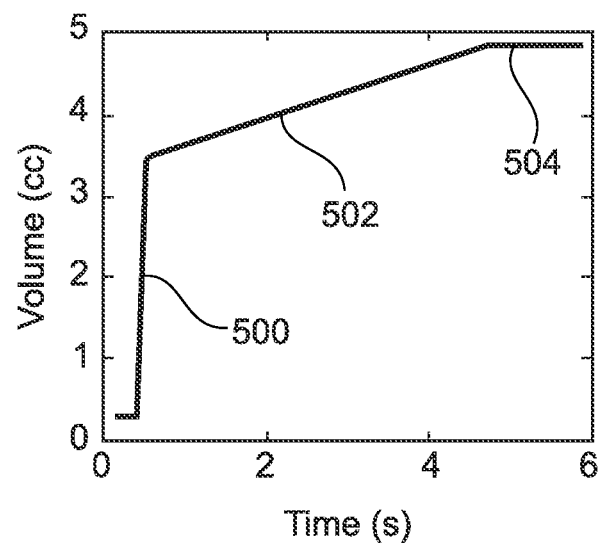
FIG. 7A shows a time-dependent gas volume profile of a compressed gas powered syringe in accordance with the prior art where the compressed gas reservoir is small relative to the internal volume of the system.
Figure 7B:
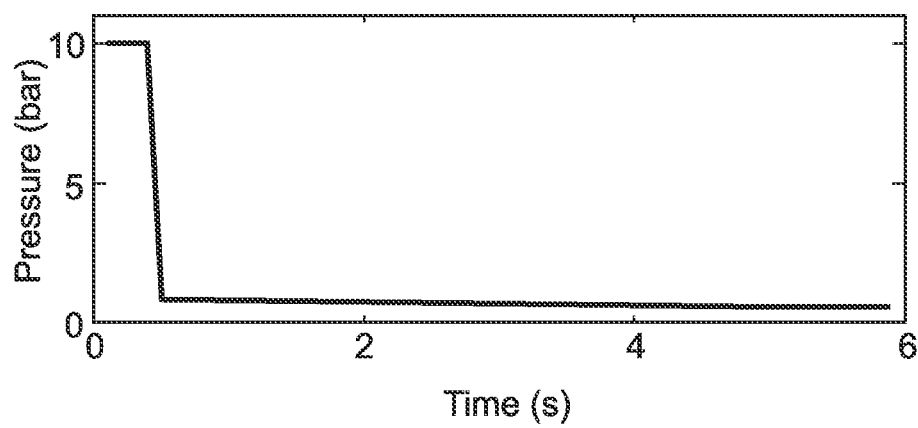
FIG. 7B shows the corresponding time-dependent pressure profile.

FIGS. 7A and 7B relate to a syringe where the reservoir of compressed gas is small (0.3 cc) relative to the internal volume of the system. FIG. 7A shows the time-dependent volume profile of the compressed gas, and FIG. 7B shows the corresponding time-dependent pressure profile of the compressed gas. Again, FIG. 7A shows a rapid increase in volume at 500 when the compressed gas reservoir is initially opened and the compressed gas fills the dead volume. This is followed by a more gradual increase in volume at 502 as the stopper begins to move and the volume behind the stopper increases. Finally, when the stopper is in its forwardmost position in the barrel, the volume of the compressed gas ceases to increase as shown at 504 of FIG. 7A. The corresponding pressure profile shown in FIG. 7B shows that there is a large and initially rapid reduction in pressure as the gas expands, and then a more gradual decrease in pressure as the stopper begins to move.

Figure 8A:
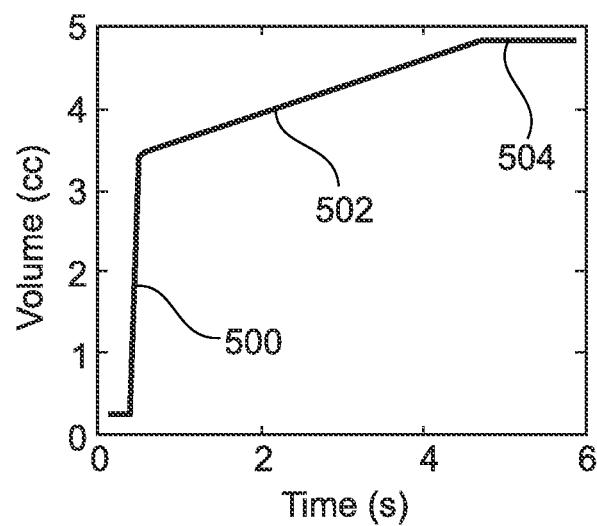
FIG. 8A shows a time-dependent gas volume profile of a propellant powered syringe in accordance with an embodiment of the present invention.
Figure 8B:
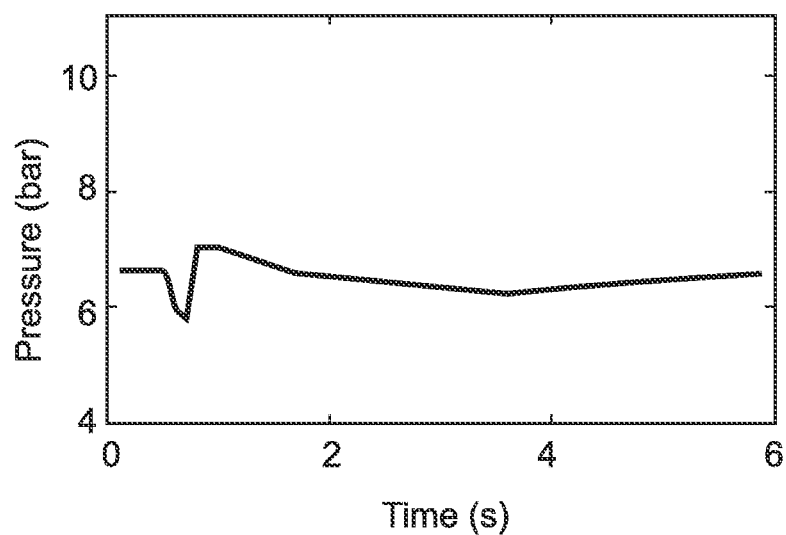
FIG. 8B shows the corresponding time-dependent pressure profile.

In contrast, if the gas is initially a liquefied gas in accordance with the present invention, the mass of the gas increases as the gas expands as the liquid boils. It is this increasing mass aligned with the increasing volume that provides a more consistent pressure profile. FIG. 8A shows a time-dependent volume profile of a syringe powered by 0.3 cc of a liquefied propellant in accordance with an embodiment of the present invention. In the reservoir (e.g. the third chamber) the propellant will be a liquid in equilibrium with a saturated vapor. Once the reservoir is opened and put into fluid communication with the volume behind the stopper, the liquid propellant boils and volume of the gas increases as shown at 500 of FIG. 8A. As with the compressed gas, once the stopper begins to move, the volume behind the stopper increases and permits the volume of the gas to increase further as shown at 502. Once the stopper reaches its forwardmost position, the volume of gas plateaus, as shown at 504. At this point there will still be some liquid propellant remaining in fluid communication with the second chamber. However, since the mass of gas increases as the liquid boils, the propellant generates more gas at the vapor pressure and therefore maintains a more constant pressure as shown in FIG. 8B. Whilst there is an initial variation in gas pressure as the reservoir is first put into fluid communication with the volume behind the stopper, there is no significant overall drop in gas pressure as there is with compressed gases, as evidenced by FIGS. 6B and 7B. Consequently, the present invention offers a much more consistent pressure profile with a very small initial volume of propellant. This makes the syringe of the present invention particularly suited to providing ancillary functions that are triggered as a result of the predictable and reliable pressure in the second chamber.

In the syringes associated with each of FIGS. 6A to 8B, the dead internal volume into which the compressed gas or vaporized propellant initially expands into is ~3 cc.

Figure 9:
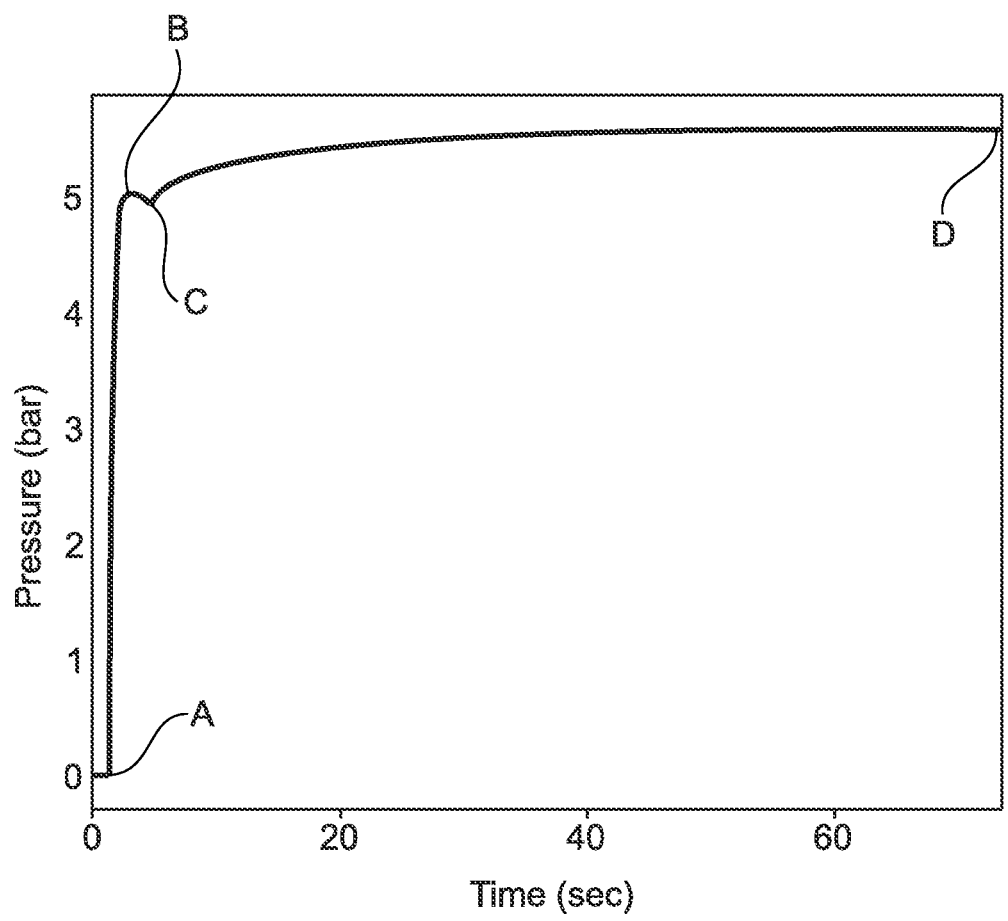
FIG. 9 shows a pressure profile of vapor pressure vs. time for propellant in the second chamber of a syringe in accordance with the present invention where liquid propellant is introduced into the second chamber.

FIG. 9 shows an example of a pressure profile (i.e. vapor pressure vs. time within the second chamber 20) exhibited by a syringe such as the one described above in relation to FIG. 1A during use. Point A indicates the start of propellant release into the second chamber 20 and the subsequent boiling of the propellant which results in a very fast increase in vapor pressure over a first time period (typically of the order of 10-100 ms) up to point B. At point B, the vapor pressure in the second chamber 20 is great enough to cause the stopper 16 to move axially forwardly and begin expulsion of medicament from the first chamber 18. In practice, the stopper 16 may start to move just before point B is reached as the pressure in the second chamber 20 is sufficient to overcome the frictional resistance of the stopper 16 in the syringe 10. As described above, the thermodynamics of the syringe 10 dictate that the vapor pressure drops during delivery. This is shown in the pressure profile of FIG. 9 as the negative gradient between points B and C over a second time period, where point C is indicative of the instant where axial movement of the stopper 16 ceases to continue (i.e. the end of delivery). Consequently, the vapor pressure at C is lower than the vapor pressure at B. A third time period between point C and point D represents the vapor increase in the second chamber 20 as the propellant therein absorbs heat from the environment. This increase tends towards the vapor pressure of the propellant at the temperature of its immediate environment (e.g. ambient temperature). Indeed, point D represents substantially this vapor pressure. For the pressure profile of FIG. 9, the vapor pressure at D is greater than both the vapor pressures at B and C (and of course A). This may be because the stopper 16 began moving axially forwardly before the propellant could reach its vapor pressure at the temperature of its immediate environment. At point D there will still be some liquid propellant remaining in fluid communication with the second chamber.

The pressure profile of FIG. 9 reveals that there is not necessarily a simple constant pressure acting on the stopper 16 (i.e. the vapor pressure in the second chamber 20) during delivery. In accordance with the present invention, this pressure profile may be manipulated so as to provide a more reliable and/or useful device, and/or be more suitable for a particular medicament or application. Indeed, as noted above, the form of the pressure profile is dependent on any one or more of i) the thermal properties of the syringe 10, ii) the rate of delivery of propellant into the second chamber 20, and iii) the phase of the propellant entering the second chamber.

Further embodiments of syringes 10 in accordance with the present invention are described below with reference to FIGS. 1B to 1F. Given the differences in configuration, the various embodiments of syringes 10 will each exhibit a different pressure profile of vapor pressure in the second chamber 20 during use.

Figure 1B:
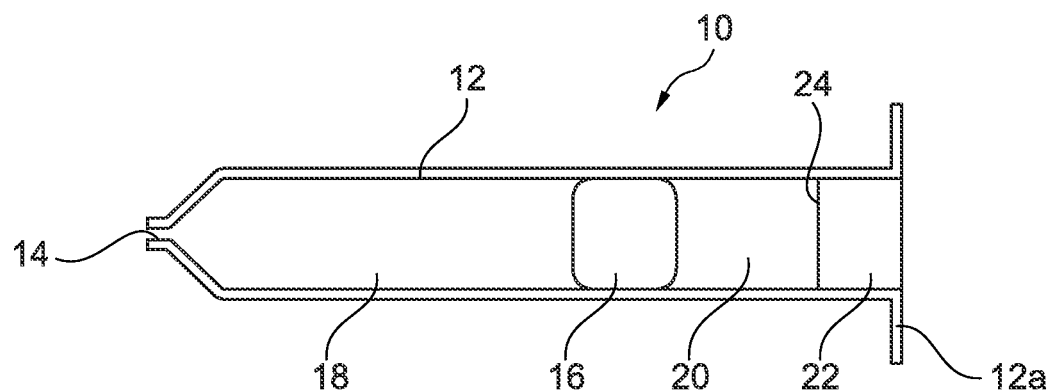
FIG. 1B is a schematic cross sectional view of a syringe according to an alternative embodiment of the present invention comprising a rupturable propellant chamber.

In FIG. 1B, a syringe 10 is shown that is largely the same as that shown in FIG. 1A, except that the third chamber 22 is no longer defined by a rupturable wall 24 forming a self-contained container 21. Instead, for the syringe 10 of FIG. 1B, the rupturable wall 24 extends across the barrel 12 in a direction substantially perpendicular to the longitudinal direction of the syringe 10 (which is parallel the axial directions referred to above). Therefore, for the syringe 10 of FIG. 1B, the third chamber 22 is defined by the rupturable wall 24 and the walls of the barrel 12. In alternative embodiments, the third chamber may be defined by the rupturable wall 24 and possibly the walls of an additional component (which may not be enveloped by or contained within the barrel 12), but where the rupturable wall provides a boundary between the third chamber 22 and the second chamber 20. The rupturable wall may, for example, be a septum separating the third chamber 22 and second chamber 20. Additionally, the rupturable wall 24 need not necessarily be perpendicular to the longitudinal axis of the syringe 10, nor need it be disposed in a single plane. As with the syringe 10 of FIG. 1A, the syringe 10 of FIG. 1B is actuated when a rupturing portion (not shown) causes the rupturable wall 24 to rupture so as to form a fluid connection between the third chamber 22 and the second chamber 20 thereby permitting the flow of propellant from the third chamber 22 into the second chamber 20. As with the syringe of FIG. 1A, the stopper 16 of the syringe 10 of FIG. 1B will then move axially forwardly under the force of the vapor pressure in the second chamber 20 to expel medicament from the first chamber 28 through the outlet 14.

Figure 1C:
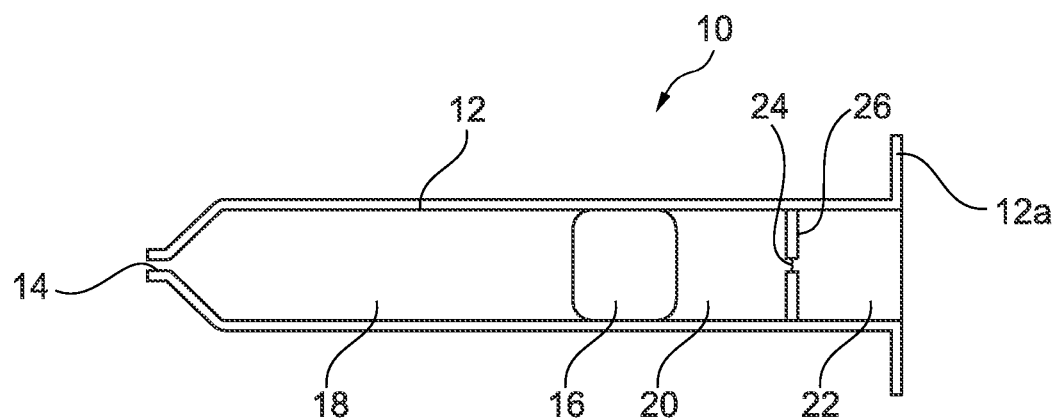
FIG. 1C is a schematic cross sectional view of a syringe according to an alternative embodiment of the present invention comprising a propellant chamber with a partially rupturable separating wall.

A further embodiment of a syringe in accordance with the present invention is shown in FIG. 1C. The syringe 10 of FIG. 1C differs from the syringe of FIG. 1B in that the third chamber 22 is not only defined by a rupturable wall 24, but also by a non-rupturable wall (or walls) 26 extending between the walls of the barrel 12 along an internal circumference of the barrel 12. In the embodiment shown, the non-rupturable wall 26 extends from the barrel 12 and has a central aperture across which the rupturable wall 24 extends. In alternative embodiments, there may be a plurality of rupturable walls 24 and non rupturable walls 26 extending across the barrel 12 in any configuration so as to define the third chamber 22. Indeed, in some embodiments, any configuration of rupturable walls 24, or rupturable walls 24 and non-rupturable walls 26, may form a third chamber 22 that does not bisect the longitudinal axis of the syringe 10.

In the embodiment of FIG. 1C, the extent of the rupturable wall 24 (which is largely determined by the size of the aperture in the non-rupturable wall 26) will largely determine the flow rate of propellant from the third chamber 22 to the second chamber 20 upon rupturing of the rupturable wall 24.

Figure 1D:
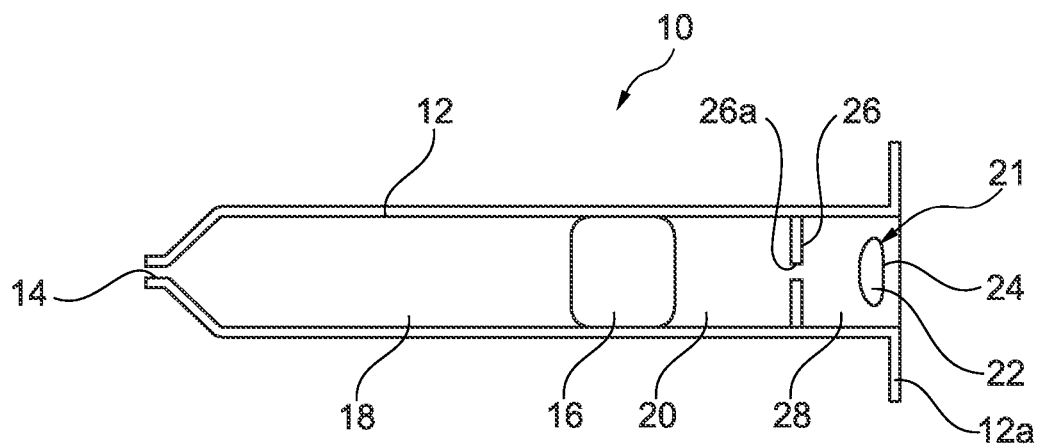
FIG. 1D is a schematic cross sectional view of a syringe according to an alternative embodiment of the present invention comprising a propellant chamber containing a self-contained rupturable container of propellant.

A further embodiment of a syringe in accordance with the present invention is shown in FIG. 1D. The syringe 10 of FIG. 1D comprises a non-rupturable wall 26 extending across the barrel 12 along an inner circumference of the barrel 12. The non-rupturable wall 26 does not form a continuous disc and has an axial aperture 26a therethrough. The non-rupturable wall 26 defines a fourth chamber 28 which is fluidly connected to the second chamber 20 via aperture 26a which defines a propellant channel. The fourth chamber 28 contains a container 21 as described above in relation to FIG. 1A. In use, the rupturable wall 24 of the container ruptures to fluidly connect the third chamber 22 to the fourth chamber 28, and therefore also to the second chamber 20 via the aperture 26a. The extent of the aperture 26a largely determines the flow rate of propellant from the fourth chamber 28 to the second chamber 20 upon rupturing of the rupturable wall 24. The aperture 26a may be a simple hole, or may be any other fluid passageway that connects the fourth chamber 28 to the second chamber 20. For example, in one embodiment, the aperture 26a may be a labyrinth arrangement or a valve arrangement that opens when the fluid pressure acting on it exceeds a predetermined threshold. A baffle arrangement may prevent or minimize the flow of droplets (e.g. a mist) of propellant passing from the fourth chamber 28 to the second chamber 20.

Figure 1E:
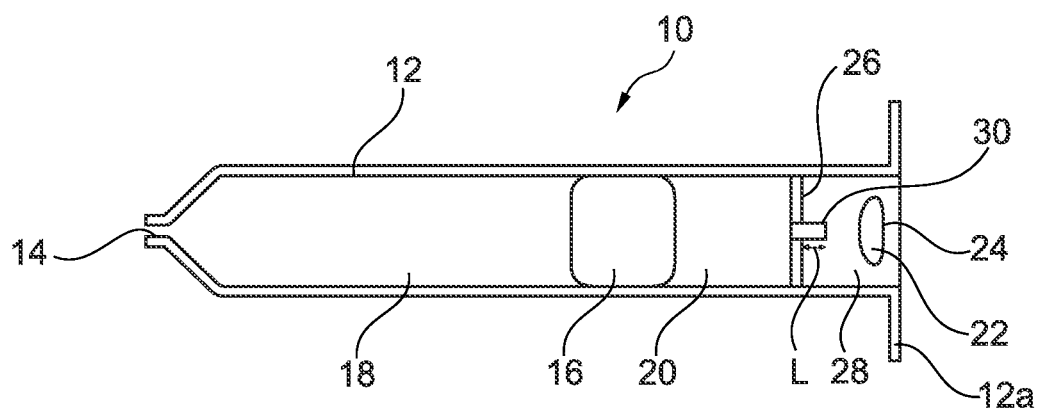
FIG. 1E is a schematic cross sectional view of the syringe of FIG. 1D additionally comprising a fluid conduit extending into the propellant chamber.

Yet another embodiment of a syringe 10 in accordance with the present invention is shown in FIG. 1E. The syringe 10 of FIG. 1E is largely the same as the syringe of FIG. 1D but the propellant channel fluidly connecting the third chamber 22 and the fourth chamber 28 is defined by a propellant conduit 30. The propellant conduit 30 has a bore therethrough fluidly connecting the third chamber 22 and the fourth chamber 28, and the bore largely determines the flow rate of propellant from the third chamber 22 to the fourth chamber 28. The propellant conduit 30 extends axially rearwardly into the fourth chamber by distance L. The axially rearwardly extending propellant conduit 30 acts to limit the quantity of liquid propellant passing from the fourth chamber 28 to the second chamber 20 during use of the syringe 10. In particular, during use of the syringe 10, the syringe 10 will be orientated so that the outlet 14 is proximate to an injection site. Usually, the syringe 10 will be orientated so that the longitudinal axis of the syringe is held vertically above the injection site (or at least be inclined with respect to the horizontal). In this orientation, liquid propellant exiting the third chamber 22 (i.e. after rupture of rupturable wall 24) will move under the influence of gravity towards the non-rupturable wall 26. The propellant conduit 30 will then extend above some, if not all, of the liquid propellant, depending on the magnitude of L and the quantity of propellant present. The propellant conduit 30 acts to limit or prevent entirely the flow of liquid propellant from the fourth chamber 28 to the second chamber 20. The syringe 10 may be used at orientations other than vertical (e.g. horizontal, or indeed any orientation between vertical and horizontal) and so it is preferable for L to be sufficient so that the flow of liquid propellant from the fourth chamber 28 to the second chamber 20 is limited, or further preferably, substantially prevented.

Modeling the second chamber 20 as a cylinder having radius r and height H, $\pi r^2 H$ should be greater than the maximum volume of liquid propellant in the second chamber 20 for the rear (open) end of the propellant conduit 30 to rise above the propellant liquid level when the syringe 10 is in a vertical orientation. Additionally, $(\pi r^2 H/2)$ should be greater than the maximum volume of liquid propellant in the second chamber 20 for the propellant conduit to remain above the propellant liquid level when the syringe 10 is in a horizontal orientation. In one example, for a 100 μl volume of propellant in a second chamber 30 of diameter 6.35 mm, the magnitude of L should be 3.158 mm or greater to be above the propellant liquid level. In another example, for a 10 μl volume of propellant in a second chamber 30 of diameter 6.35 mm, the magnitude of L should be 0.316 mm or greater to be above the propellant liquid level.

Figure 1F:
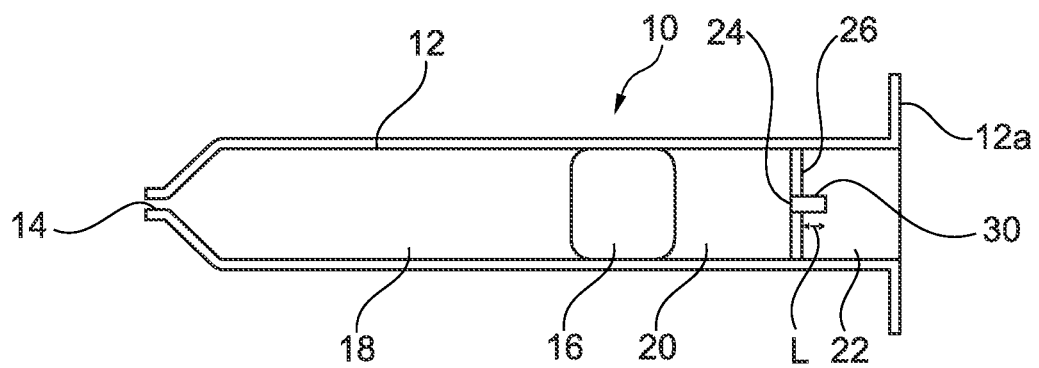
FIG. 1F is a schematic cross sectional view of a syringe according to an alternative embodiment of the present invention comprising a propellant chamber with a partially rupturable separating wall and a fluid conduit extending into the propellant chamber.

A similar syringe 10 to that described above in relation to FIG. 1E is shown in FIG. 1F. In the syringe 10 of FIG. 1F, the third chamber 22 is not defined by a self-contained container 21, but by a combination of a rupturable wall 24, non-rupturable wall 26 and the barrel 12 (similar to the embodiment shown in FIG. 1C). Additionally, the syringe 10 of FIG. 1F comprises a propellant conduit 30 that extends axially rearwardly into the third chamber 22 by a distance L and has a bore fluidly connecting the third chamber 22 to the second chamber 20 (albeit for the presence of the rupturable wall 24). The rupturable wall 24 may be located at any position along the bore of the propellant conduit 30 to temporarily fluidly isolate the third chamber 22 from the second chamber 20. As with the embodiment of FIG. 1E, the propellant conduit 30 acts to limit or prevent entirely the flow of liquid propellant into the second chamber 20, this time from the third chamber 22. As described above, a labyrinth or valved arrangement may be present to prevent droplets of liquid propellant (e.g. a mist) passing through into the second chamber 20.

The pressure profile of vapor pressure of propellant in the second chamber 20 during use will be influenced by the phase of propellant entering the second chamber. For example, if a constant or near constant flow of gas-phase (or predominantly gas-phase) propellant is being supplied to the second chamber 20 through the propellant conduit 30, then the stopper 16 will experience a more constant vapor pressure and move axially forwardly at a more constant rate within the barrel 12 and expel medicament from the first chamber 18 at a constant rate. This may be particularly suitable for applications where it is important to deliver medicament at a constant or near constant rate.

The passage of propellant through the propellant conduit 30 or aperture 26a does not constitute "regulated delivery". Indeed, passage through the propellant conduit 30 or aperture 26a constitutes bolus delivery of the propellant into the second chamber 20.

Unless otherwise stated, all described features of the syringe of FIG. 1A (excluding the form of the third chamber 22) may be applicable to any one or more of the syringes of FIGS. 1B to 1F. Indeed, any non-mutually exclusive features of any one or more of the syringes of FIGS. 1A to 1F may be applicable to any other of the syringes of FIGS. 1A to 1F.

Figure 10:
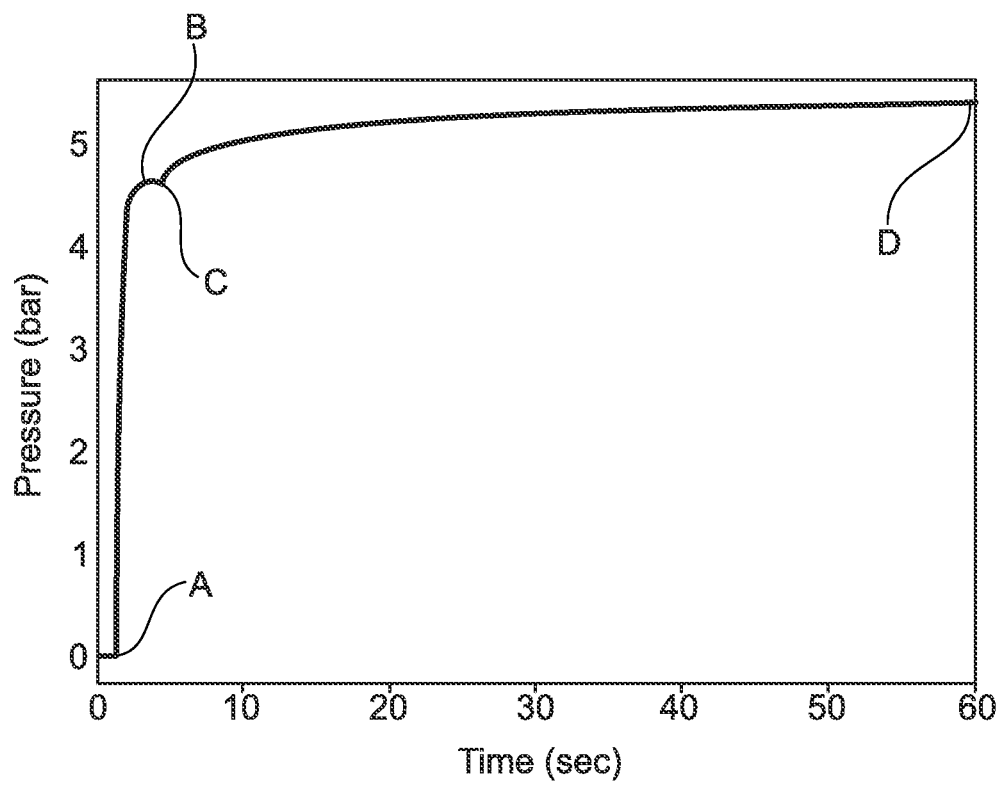
FIG. 10 shows a pressure profile of vapor pressure vs. time for propellant in the second chamber of a syringe in accordance with the present invention where gaseous and liquid propellant is introduced into the second chamber.

FIG. 10 shows an example pressure profile of vapor pressure in the second chamber 20 of a syringe 10 where mostly gas propellant is supplied to the second chamber 20. The pressure profile of FIG. 10 shows that propellant enters the second chamber 20 at point A and immediately results in an increase of vapor pressure in the second chamber 20 to an initial maximum vapor pressure and point B. The rate of increase of vapor pressure decreases slightly immediately prior to reaching point B. The change from point A to point B occurs over a first time period. The vapor pressure then decreases slightly over a second time period as the stopper 16 begins to move axially forwardly to deliver medicament until point C is reached. During the second time period, the little liquid that is present reduces in temperature as it gives up heat of vaporization by the mechanism described above in relation to the pressure profile of FIG. 9. However, the decrease and the rate of decrease between points B and C in FIG. 10 are less than the respective decrease and the rate of decrease in the pressure profile of FIG. 9. In FIG. 10, point C represents the end of delivery when the stopper 16 has reached the front of the barrel 12 and is no longer moving axially forwardly. Subsequent to point C being reached, the propellant in the second chamber 20 absorbs heat from the environment which increases the vapor pressure within the second chamber 20. This increase tends towards the vapor pressure of the propellant at the temperature of its immediate environment (e.g. ambient temperature) which is indicated at point D, where the time period between points C and D is a third time period. At point D there will still be some liquid propellant remaining in fluid communication with the second chamber.

Figure 11:
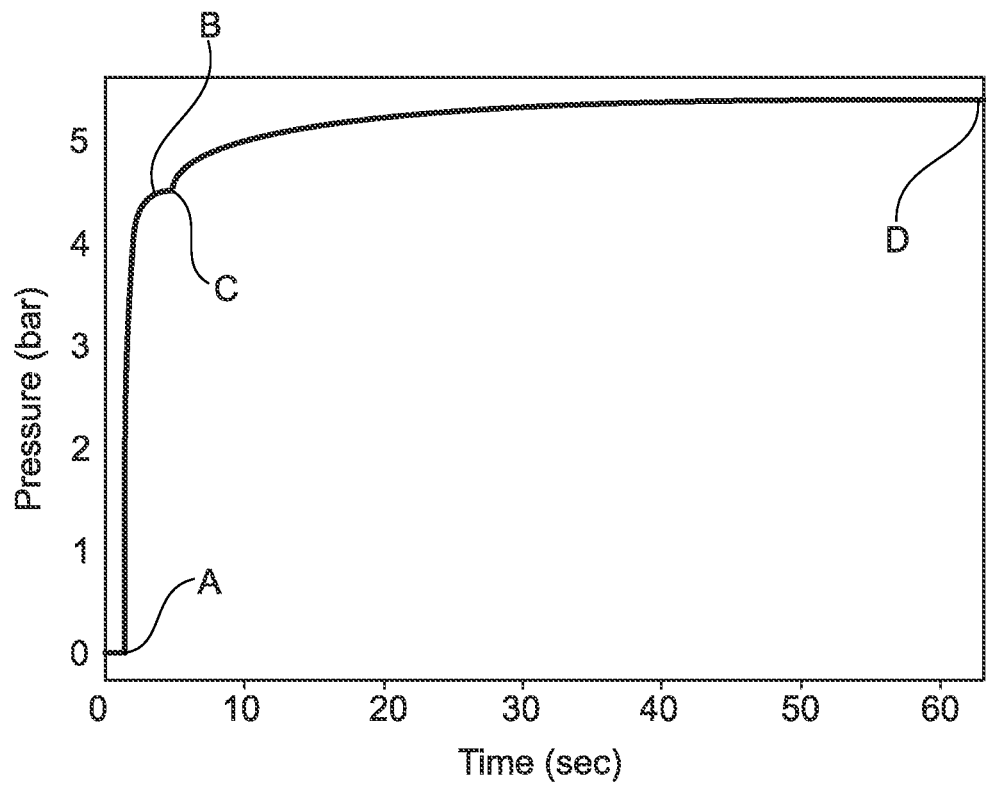
FIG. 11 shows a pressure profile of vapor pressure vs. time for propellant in the second chamber of a syringe in accordance with the present invention where only gaseous propellant is introduced into the second chamber.

FIG. 11 shows an example of a pressure profile of a syringe 10 in accordance with the present invention where substantially only gas propellant is introduced into the second chamber 20. The pressure profile of FIG. 11 is largely similar to that of FIG. 10, however, in the pressure profile of FIG. 11, there is substantially no change in the vapor pressure between points B and C. That is, during delivery, there is a substantially constant vapor pressure in the second chamber 20. As with the pressure profile of FIG. 10, subsequent to the end of delivery (i.e. after point C), the vapor pressure increases as the propellant in the second chamber absorbs heat from the environment. At point D there will still be some liquid propellant remaining in fluid communication with the second chamber.

Comparing the pressure profiles of FIGS. 9, 10 and 11, it can be seen that the drop in vapor pressure between points B and C is reduced as the proportion of gas propellant relative to liquid propellant introduced into the second chamber 20 is increased. It is understood that this is predominantly due to the initial maximum of vapor pressure (i.e. the vapor pressure at point B) being reduced for more proportionally gaseous propellant introduced into the second chamber 20. That is, the vapor pressure in the second chamber 20 does not reach its vapor pressure at the temperature of its immediate environment (e.g. ambient temperature) during delivery when only gaseous or partially gaseous propellant is introduced into the second chamber 20.

Indeed, it is anticipated that for some syringes in accordance with the present invention, where only gaseous propellant is introduced into the second chamber 20 that there will be no initial maximum prior to the end of delivery. That is, the initial increase in vapor pressure subsequent to point A will result in the movement of the stopper 16 and the expulsion of medicament, but at the end of delivery the vapor pressure will be at a level not previously exceeded in the delivery process. To put that another way, point C will represent the highest vapor pressure of the first and second time periods. In this scenario, following point C, the vapor pressure will increase as the propellant absorbs heat energy from its environment and tends towards the vapor pressure of the propellant at the temperature of its immediate environment (e.g. ambient temperature).

As described above, the form of the pressure profile produced by a propellant powered syringe 10 is determined by one of three parameters, namely i) the thermal properties of the syringe 10, ii) the rate of delivery of propellant into the second chamber 20, and iii) the phase of the propellant entering the second chamber 20. The embodiments described above demonstrate the effects of parameters ii) and iii) on the form of the pressure profile.

Figure 12:
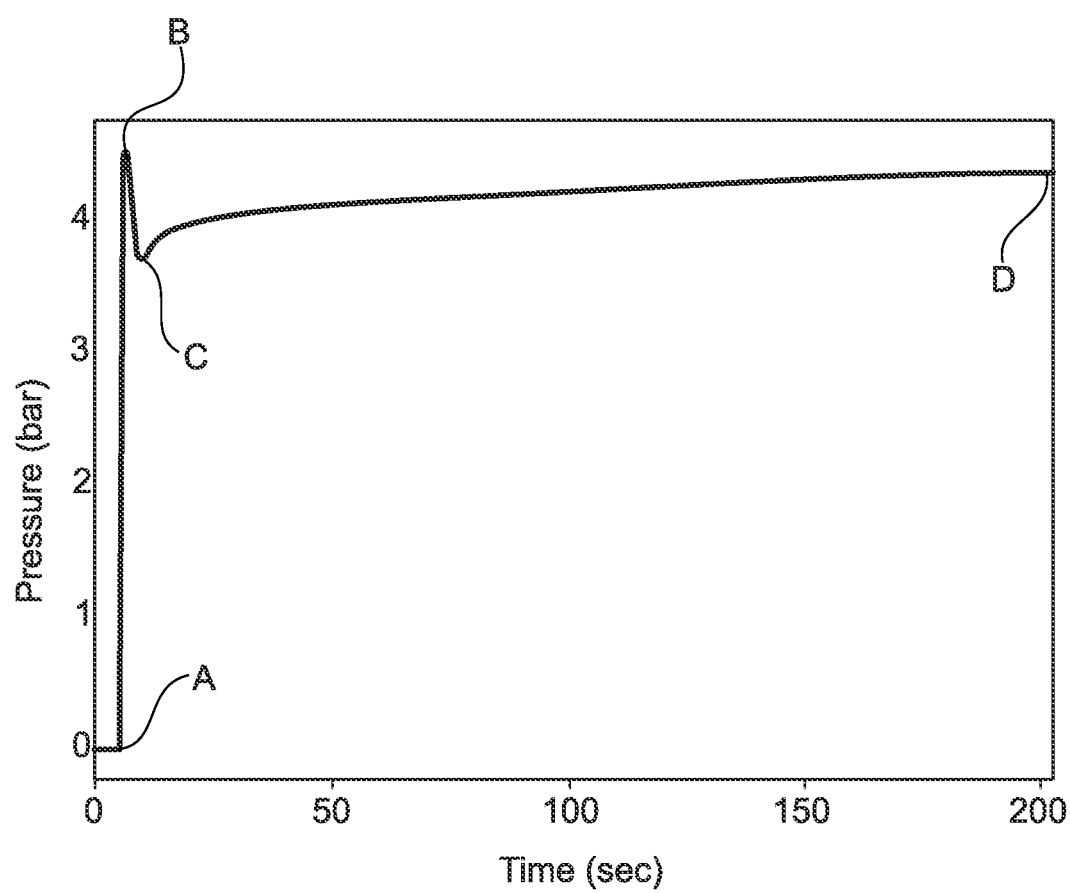
FIG. 12 shows a pressure profile of vapor pressure vs. time for propellant in the second chamber of a syringe in accordance with the present invention where the propellant in the second chamber has been actively cooled during delivery.

FIG. 12, however, demonstrates the effects of parameter i) on the form of the pressure profile. In particular, FIG. 12 represents the pressure profile of a syringe 10 in accordance with the present invention, similar to the syringe that produced the pressure profile of FIG. 9. However the syringe 10 associated with the pressure profile of FIG. 12 additionally includes apparatus to further cool the propellant in the second chamber 20 during use. By "further cool" is meant reducing the temperature of the propellant in the second chamber 20 by an amount that is more than if the apparatus to further cool were not present, i.e. where the only reduction in temperature in liquid propellant is due to loss of latent heat of vaporization. The skilled person will appreciate that the propellant in the second chamber 20 can be further cooled by several methods within the scope of the present invention. For example, a coolant or refrigerant (which may be an additional supply of the propellant) may be applied to the outside of the barrel 12 proximate the second chamber 20 so that the portion of the barrel 12 proximate the second chamber 12 is cooled thereby removing some of its thermal energy such that it has less thermal energy to supply to the propellant in the second chamber 20. If the part of the barrel 12 proximate the second chamber 20 has less thermal energy to provide to the propellant in the second chamber 20, when the temperature of the liquid propellant falls as it loses heat of vaporization as it boils, the liquid propellant has less thermal energy available to it from the barrel 12 proximate the second chamber 20 as it otherwise would. Therefore, there is less thermal energy available to the liquid propellant in its immediate environment that may be absorbed by the liquid propellant to offset the reduction in temperature due to boiling. For this reason, during operation of the syringe 10, the drop in vapor pressure in the second chamber 20 is greater than it would otherwise be if no means to cool the propellant therein were in place. Indeed, any means or method that reduces the thermal energy available to the liquid propellant in the second chamber 20 as it is boiling and causing the stopper 16 to move axially forwardly in the barrel 12 will result in a greater drop in vapor pressure in the second chamber 20 than would otherwise occur if no such means or method were in place.

In the case where a coolant or refrigerant is applied to the outside of the barrel 12 proximate the second chamber 20, the coolant or refrigerant may be channeled or otherwise caused to travel towards the injection site after cooling the barrel 12 (and the liquid propellant in the second chamber 20) to additionally provide cooling to the injection site. The cooling provided to the injection site may provide the effect of reducing the level of pain caused by the injection as perceived by the patient.

In other embodiments, thermally insulating material may be present on or around the barrel 12 proximate the second chamber 12 so that the thermal transfer of heat from the environment to the barrel 12 is reduced. In this embodiment, heat lost from the barrel 12 and absorbed by the liquid propellant in the second chamber 20 may not be replaced (or such replacement will at least be restricted) by absorption of heat by the barrel 12 from the external environment. Again, such measures will limit the heat transfer to the second chamber 20 which contains the propellant so that a greater vapor pressure drop will be exhibited.

Conversely, if more thermal energy is supplied to the second chamber 20 such that the liquid propellant contained therein is able to absorb more thermal energy during delivery than it otherwise would be able to, the drop in vapor pressure exhibited in the second chamber 20 during delivery may be reduced and even reduced to substantially zero. Thermal energy may be supplied to the second chamber 20 by active heating means, which for example may be achieved by providing a heat source that has a temperature above the ambient temperature so that thermal energy may be transferred from the heat source to the second chamber 20, and in particular to the propellant contained therein. Alternatively, the thermal properties of the syringe 10, e.g. the barrel 12, may be configured so as to increase the rate of heat transfer from the environment to the second chamber 20. For example, the materials of the syringe 10 may be chosen such that they have a high thermal conductivity to maximize heat transfer into the second chamber 20 so that the liquid propellant is able to absorb sufficient heat to offset (i.e. reduce or eliminate) the reduction in temperature due to vaporization. Of course, if using materials having high thermal conductivity to construct the syringe 10, the materials must also provide other desired physical properties (e.g. strength and durability) to a sufficient degree.

Thus, in accordance with the present invention a syringe 10 may be provided that has suitable properties such that upon actuation of the syringe 10, a desired pressure profile of vapor pressure in the second chamber is exhibited. The desired pressure profile may be dictated by the desire to produce a delivery having a particular pressure profile, to suit a particular medicament or injection type, for example. Alternatively, the desired pressure profile may be dictated by the requirement to have a pressure feature of a particular type (e.g. magnitude, duration, gradient or rate etc.). The pressure feature may be used to trigger a subsequent action so that more complex modes of operation of the syringe can be utilized (as is described in more detail below).

As described above, the "first time period" is the time period between the initial release of propellant into the second chamber 20 and the initial maximum vapor pressure. Typically (although not always, as described above) the initial movement of the stopper 16 will be coincident with an initial maximum vapor pressure from which the vapor pressure decreases from over the second time period. The "second time period" is the time period between the initial forwardly axial movement of the stopper 16 and the point where forward axial movement of the stopper 16 is arrested (i.e. the end of the delivery phase when the stopper 16 reaches the front end of the barrel 12). The "third time period" is defined as the time period between the end of the second time period and the point where vapor pressure in the second chamber 20 reaches a predetermined level. In a preferable embodiment, the predetermined level determining the third time period is the vapor pressure of the propellant at the temperature of its immediate environment (e.g. ambient temperature).

In preferable embodiments, the syringe 10 in accordance with the present invention exhibits a pressure profile of vapor pressure in the second chamber 20 wherein the first time period is less than 1.0 seconds. In further preferable embodiments, it is preferable for the first time period to be shorter, such as less than 0.5 seconds, less than 0.2 seconds, or less than 0.1 seconds. In preferable embodiments, it is preferable for the second time period to be less than 15 seconds. However a second time period of around 15 seconds represents a relatively long delivery period, so in practice it may be more preferable if the second time period is less than 10 seconds and further preferably less than 5 seconds. In particularly preferable embodiments, the second time period is less than 3 seconds, less than 2 seconds, or less than 1 second. Where an initial maximum vapor pressure (a "first pressure") is reached that is substantially coincident with the initial movement of the stopper 16 (i.e. coincident with the end of the first time period and the beginning of the second time period) it is preferable that this be less than 15 bar, or further preferably less than 10 bar, less than 8 bar or less than 6 bar. In a preferable embodiment, the first pressure is substantially equal to the vapor pressure of the propellant at the temperature of its immediate environment (e.g. ambient temperature). Defining the vapor pressure in the second chamber 20 at the end of the second time period (i.e. the start of the third time period) as a "second pressure", in preferable embodiments the second pressure is preferably less than 99% of the first pressure, or further preferably less than 95% or less than 90% of the first pressure. Similarly, in preferable embodiments the second pressure is preferably greater than 50% of the first pressure, or further preferably greater than 75% or greater than 85% of the first pressure. In preferable embodiments, the difference between the first pressure and the second pressure is more than 0.1 bar, and further preferably more than 0.5 bar or more than 1.0 bar.

In accordance with the present invention, there is provided a syringe propellable by a propellant that boils at a predetermined temperature where the syringe comprises a barrel having an outlet at a front end, and a stopper axially moveable in the barrel, wherein the stopper defines and separates a first chamber and a second chamber. The first chamber is axially forwards of the stopper and is configured for containing a substance such as a medicament, and the second chamber is axially rearwards of the stopper and is configured to receive propellant for acting on the stopper to move the stopper axially forwardly in the barrel to expel medicament through the outlet upon actuation of the syringe. Indeed, this syringe is much like the syringes described above in accordance with other embodiments of the invention, and, indeed, the syringe of this further aspect may be identical to one of those earlier described syringes. However, the syringe of this further aspect is not necessarily limited to receiving propellant from a third chamber that includes a rupturable container. Indeed, propellant may be supplied via a valved container or otherwise to the syringe of this further aspect of the invention.

The syringe is configured such that, in use, upon actuation of the syringe, propellant is released into the second chamber (by any suitable means) and the pressure in the second chamber increases causing the stopper to move axially forwardly in the barrel and begin to expel the substance contained in first chamber therefrom through the outlet. The syringe additionally comprises a trigger that is activated (or "triggered") in response to the pressure in the second chamber satisfying a predetermined condition. Upon activation of the trigger, an "action" is triggered. The action may be the movement of a protecting needle shield between a retracted exposing position and a forward protecting position. Alternatively, the syringe may be part of a larger autoinjector device where the syringe is axially moveable between a first position where the needle is wholly within a housing of the device and a second position where the needle protrudes from the housing so as to be able to penetrate an injection site. In this embodiment, the action triggered may be the movement of the syringe in the device between the first and second positions. Additionally or alternatively, the action triggered may be the activation of one or more indicators to produce one or more signals. The indicators may include a visual indicator, such as an LED. Alternatively, the indicators may include an audible indicator, such as a loud speaker. In any case, the one or more indicators may signal the end of delivery of medicament or signal that a predetermined time period has elapsed since the end of delivery.

The predetermined condition that causes the activation of the trigger may be a predetermined pressure being exceeded in the second chamber. The trigger may be activated when the predetermined pressure is exceeded in the second chamber after a predetermined time period has elapsed or subsequent to a prior predetermined condition being satisfied. The predetermined condition may be the pressure falling below a predetermined pressure, and may be the pressure falling below a predetermined pressure after a predetermined time period has elapsed or subsequent to a prior predetermined condition being satisfied. In further or alternative embodiments, the predetermined pressure may be in respect of the absolute pressure in the second chamber, a ratio of pressures in the second chamber (with respect to time), or a difference in pressures in the second chamber (with respect to time). Alternatively, the predetermined condition could be a ratio or difference between the pressure in the second chamber and the pressure in a reference chamber, such as the third chamber.

The trigger may include a pressure sensor that is connected to an actuator for causing the further action. Additionally or alternatively, the trigger may include a mechanism whereby the pressure in the second chamber directly causes the further action. For example, the vapor pressure in the second chamber may be used (once a predetermined condition is satisfied) to directly bias a needle shield to its forward protecting position, or cause some other physical mechanism to move. In the case of a moving needle shield, the needle shield could be released so that under the influence of a biasing member, the needle shield is biased against the injection site (e.g. the patient's skin) so that when the syringe is removed from the injection site there is no resistance to the bias provided by the biasing member and the needle shield moves fully to its protecting position.

If the syringe is configured to exhibit a pressure profile in accordance with the present invention, the pressure profile can be tailored (as part of the specification of the syringe) to have pressure features that can be used as or for the predetermined condition that activates the trigger.

As noted above, in certain embodiments, propellant may be provided to the second chamber by means that do not have rupturable walls (in accordance with certain aspects of the present invention). For example, the syringe may comprise a dispenser for providing propellant to the second chamber, wherein the dispenser is moveable from a closed position in which propellant cannot exit the dispenser to an open position in which a predetermined volume of propellant can exit the dispenser. The dispenser may have a capacity for containing propellant, where the predetermined volume is less than the capacity. the capacity may be defined by a first internal volume of the dispenser, and the predetermined volume is defined by a second internal volume of the dispenser, and wherein in the closed position, the first internal volume is fluidly connected to the second internal volume so as to allow propellant to fill the second internal volume, and in the open position, the first internal volume is not fluidly connected to the second internal volume and the second internal volume is fluidly connected to the second chamber so as to allow the predetermined volume of propellant to be provided to the second chamber.

Figure 13B:
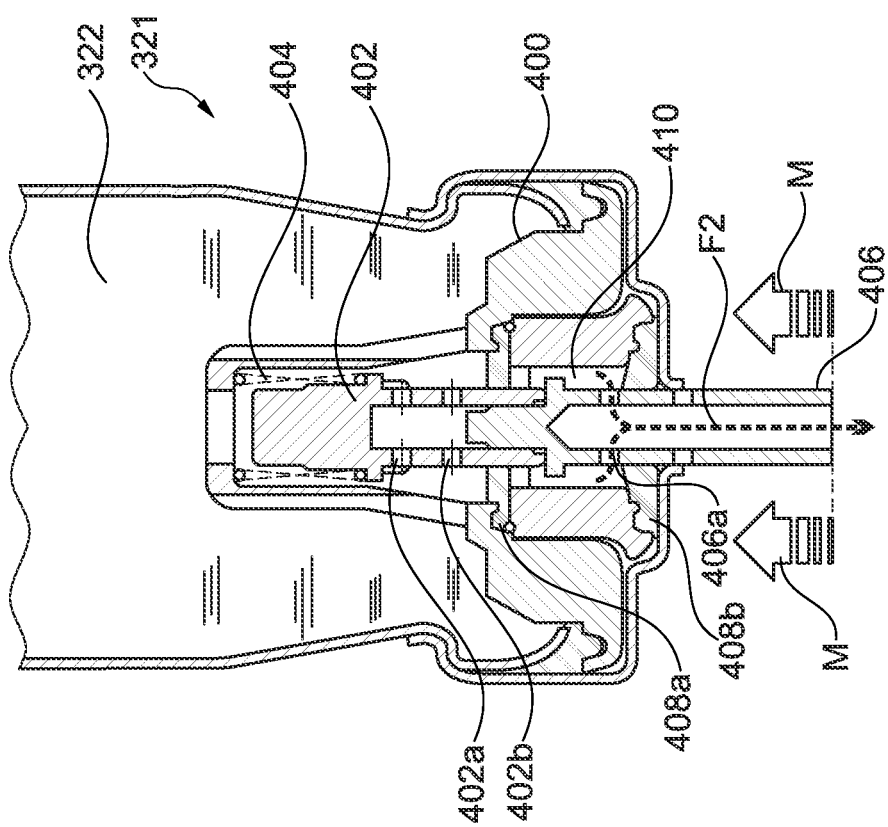
FIGS. 13A and 13B show cross-sectional views of a dispenser for providing a predetermined volume of propellant to the second chamber of the syringe in accordance with certain embodiments of the present invention, where
Figure 13A:
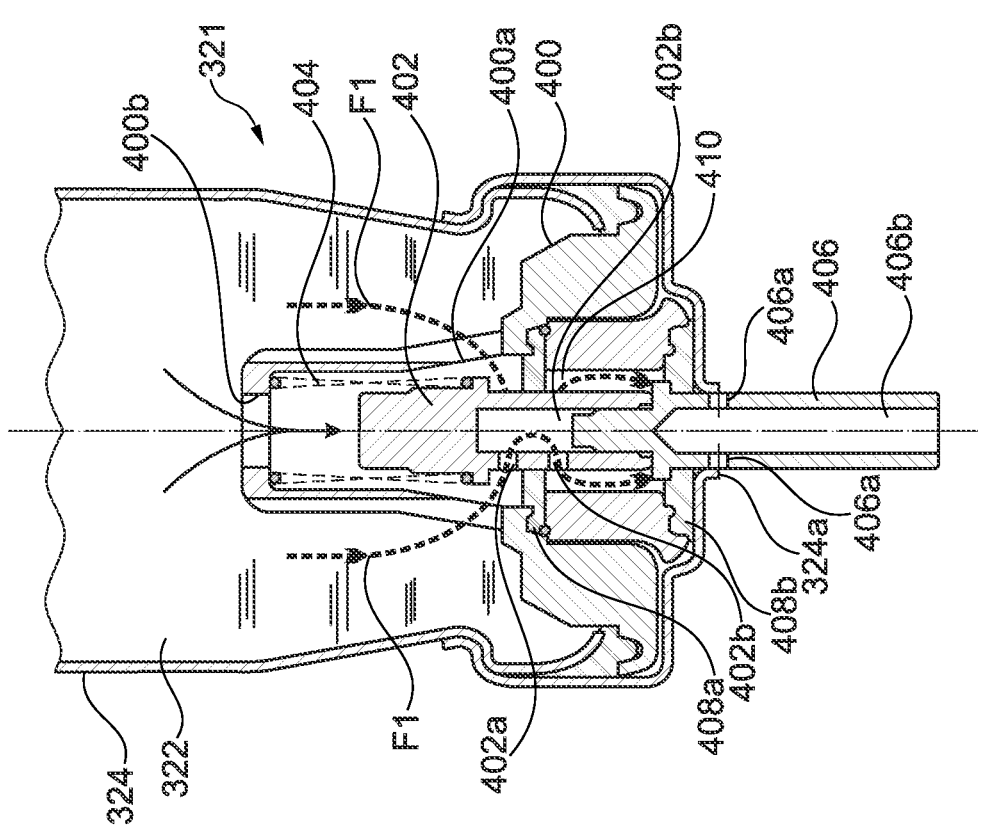

FIGS. 13A and 13B show one specific embodiment of an embodiment of a propellant dispenser 321 for supplying propellant to the second chamber, where the propellant dispenser 321 does not include a rupturable wall. The dispenser 321 comprises a reservoir 324 that defines a central volume 322 containing propellant. Inside the central volume 322 is an internal frame 400 that has a series of channels 400a,400b for allowing propellant to pass therethrough. Within the internal frame 400 are a carriage 402 and a nozzle 406 that are connected to one another. The carriage 402 and nozzle 406 are connected to one another and are axially moveable within the dispenser 321 between a closed position in which propellant cannot exit the dispenser 321 (as shown in FIG. 13A) and an open position in which propellant can exit the dispenser 321 (as shown in FIG. 13B). The carriage 402, and hence nozzle 406, are biased axially forwardly from the frame 400 to the closed position by a biasing member 404 in the form of a spring in the embodiment shown.

The carriage 402 and nozzle 406 are moveable through a rear seal 408a and a forward seal 408b. The rear seal 408a and the forward seal 408b together with the frame 400 define an annulus 410 around the carriage 402 and the nozzle 406. The nozzle 406 is moveable so as to protrude through the forward seal 408b and an opening 321a of the dispenser 321 in at least the open position.

The carriage 402 has a pair of passageways 402a,402b that, together with a hollow region 402b of the carriage 402, form a fluidic bypass pathway (indicated as F1 in FIG. 13A) around the rear seal 408a when the carriage 402 is in the closed position. Therefore, in the closed position, propellant is able to flow from the central volume 322 to the annulus 410 via the passageways 402a,402b.

Given that the carriage 402 and the nozzle 406 are biased by the spring 404 towards the closed position, the central volume 322 will be fluidly connected to the annulus 410 in the natural state of the dispenser 321 in the absence of external forces acting on the carriage 402 and nozzle 406. In the closed position, there is no fluid pathway from the annulus 410 to outside of the dispenser.

If the nozzle 406 and carriage 402 are moved axially rearwardly (as indicated by arrows M in FIG. 13B), they act against the spring 404 and move towards their open position. In the open position, the pair of passageways 402a,402b both move axially rearwardly of the rear seal 408a so that they no longer form a bypass pathway around the rear seal 408. Thus, in the open position, the central volume 322 is no longer fluidly connected to the annulus 410. However, in the open position the annulus 410 is fluidly connected to the outside of the dispenser 321 via one or more radial passageways 406a in the nozzle 406 that fluidly connect the annulus 410 to a hollow channel 406b of the nozzle 406 that is open to the external environment of the dispenser 321, bypassing the forward seal 408b (indicated by F2 in FIG. 13B). Thus, in the open position, the entire volume of propellant present in the annulus 410 is dispensed from the dispenser 321. For completeness, it is noted that in the closed position, the one or more radial passageways 406a do not fluidly connect the annulus 410 to the hollow channel 406b thus preventing fluid communication between the annulus 410 and the external environment.

Therefore, unlike some prior art valve dispensers, the dispenser 321 described above with reference to FIGS. 13A and 13B only dispenses a predetermined volume of fluid (propellant) when in the open position, where the predetermined volume is defined by the volume of the annulus 410. This is contrast to some prior art dispensers, where once in the open position, the dispenser will continue to dispense fluid until moved to a closed position. The presently described dispenser 321 is therefore advantageous for use with the present invention in that a predetermined volume of propellant can be provided to the second chamber, where the predetermined volume can be tailored for a particular application, such as for delivering a specified dose of medicament contained in the first chamber.

Whilst the above described embodiment represents a preferable arrangement of such as dispenser 321, alternative embodiments may comprise any arrangement that is capable of providing a predetermined volume of propellant to the second chamber when moved to an open position, such that it is reusable to then provide a further predetermined volume of propellant at a later time. Crucially for these embodiments, once the dispenser is in an open position, propellant is not delivered continuously such that only the position of the dispenser determines when delivery of propellant will cease.

In another example of a propellant dispenser (as illustrated in FIGS. 36A and 36B), a container 700 of propellant has a valved outlet 702 that is moveable between a closed position (illustrated in FIG. 36A) where propellant cannot exit the container 700 and an open position (illustrated in FIG. 36B) where propellant can exit the container 700. The dispenser additionally has a latching mechanism 708 or other similar arrangement that prevents the valved outlet 702 moving back to the closed position once moved to the open position. Therefore, once the valve has been moved to the open position, the entire volume of propellant in the container 700 is discharged through the valved outlet 702. Preferably, the container 700 is configured to contain a predetermined volume of propellant sufficient for the delivery of a dose of medicament. In this example, the rupturing portion comprises the valved outlet 702 and the third chamber 22 is ruptured when the valved outlet 702 is in the open position and prevented from moving back to the closed position. That is, the third chamber 22 is ruptured in the sense that it is irreversibly opened and the entire contents of the third chamber 22 discharge therefrom. In the specific example illustrated in FIGS. 36A and 36B, the valved outlet 702 is a valve having a valve body 704, valve stem 706, and a locking member 708, where the valve stem 706 is slidably moveable relative to the valve body 704 between a non-dispensing ("closed") position (FIG. 36A) in which an outlet port of the valve stem 706 is out of fluid communication with the third chamber 22, and a dispensing ("open") position in which the outlet port is in fluid communication with the third chamber 22 (via channel 712) so as to permit transfer of propellant from the third chamber 22 through the valve stem 706.

The locking member 708 is configured to prevent return of the valve stem 706 into the non-dispensing position once the valve stem 706 slides beyond a locking position.

In the embodiment illustrated in FIGS. 36A and 36B, the locking member 708 and the valve stem 706 comprise inter-engaging members, where the inter-engaging members contact one another during movement of the valve stem 706 towards the dispensing position and permit movement of the valve stem 706 into the dispensing position, and contact one another during attempted movement of the valve stem 706 from beyond the locking position back towards the dispensing position and prevent movement of the valve stem 706 back into the non-dispensing position.

The inter-engaging members, may contact one another during movement of the valve stem 706 towards the dispensing position and permit movement of the valve stem 706 into the dispensing position by flexing or other distortion of at least one of the inter-engaging members.

In a preferable embodiment (such as the one illustrated in FIGS. 36A and 36B), the inter-engaging member of the valve stem 706 comprises a flange 714. Wherein, further preferably, a distal edge 714a of the flange 714 is angled to promote flexing of the locking member 708 during movement of the valve stem into the dispensing position.

In a further or alternative preferable embodiment, the inter-engaging member of the locking member 708 comprises at least one flexible latch, wherein the at least one flexible latch preferably exhibits elastic behaviour.

The locking position of the valve stem 706 may be defined as a point where the inter-engaging member of the valve stem 706 slides beyond, and disengages from, the inter-engaging member of the locking member 708.

In some embodiments (such as the one illustrated in FIGS. 36A and 36B), the valve may further comprise a biasing member (a compression spring 710, for example) for biasing the valve stem 706 into the non-dispensing position.

FIG. 14A shows an embodiment of the present invention where a further action, additional to the movement of the stopper 16, is caused by the pressure in the second chamber 20 satisfying a certain condition.

In FIG. 14A, the syringe barrel 12 is held in a housing 600 that has an opening 600a. Within the housing 600, a moveable piston 606 is in contact with the syringe barrel 12 and is also in fluid communication with the second chamber 20. The moveable piston 606 is arranged such that vapour pressure from boiling propellant can act both on the moveable piston 606 and on the stopper 16. The second chamber 20 encompasses the entire volume between the propellant source and the stopper 16.

Returning to the specific embodiment shown in FIG. 14A, the vapour pressure in the second chamber 20 first acts on the moveable piston 606. The moveable piston 606 has a resistance to axial movement that is at least partly due to friction, stiction and the properties and configuration of other components (e.g. the syringe barrel 12) that the moveable piston 606 is in contact with. The moveable piston 606 therefore acts as a trigger that moves and causes the axial movement of the syringe barrel 12 relative to the housing 600 when the pressure in the second chamber 20 that is acting on the moveable piston 606 reaches a sufficiently high level so as to be capable of moving the moveable piston 606 axially forwardly. In moving axially forwardly, the moveable piston 606 causes the syringe barrel 12 to move towards a front end of the housing 600 such that the outlet of the barrel 12 is brought closer to the opening 600a at the front end of the housing 600. If the syringe barrel 12 has a needle attached to the outlet 14, then the movement of the syringe barrel 12 relative to the housing 600 may be between a first position where the needle does not protrude from the opening 600a of the housing 600, to a second position where the needle does protrude from the opening 600a of the housing 600. When the syringe barrel 12 reaches (or is approaching) its forwardmost position, it is preferable for the vapour pressure in the second chamber 20 to cause the stopper 16 to move axially forwardly to expel medicament from the first chamber 18. The sequencing between movement of the moveable piston 606 relative to the housing 600 and the movement of the stopper 16 relative to the syringe barrel 12 may be achieved by tailoring the resistance to movement of the moveable piston 606 and the stopper 16 such that the form of the pressure profile in the second chamber 20 determines the chronology of the respective movements. As with other embodiments of the invention, movement of the stopper does not require the activation of the trigger.

FIG. 14B shows a similar but alternative embodiment to that shown in FIG. 14A. In FIG. 14B, a moveable piston 606 is arranged as an annulus that is affixed to the outer circumference of the syringe barrel 12. Axially rearward of the moveable piston 606, there is a rigid annulus 604 that extends radially inwardly from the housing and seals against the outer circumference of the syringe barrel 12. In this embodiment, the volume between the moveable piston 606 and the rigid annulus 604 is in fluid communication with the second chamber 20 (fluid connection not shown) such that when the pressure in the second chamber 20 reaches a sufficiently high level, it may cause the moveable piston 606 to move axially forwardly relative to the housing 600 (and the rigid annulus 604) so as to move the syringe barrel 12 axially forwardly relative to the housing 600. As a possible variation of the embodiment of FIG. 14B, the rigid annulus 604 may be omitted such that the pressure in the second chamber 20 acts between a rear wall of the second chamber 20 and the moveable piston 606 to cause the syringe barrel 12 to move.

Figure 14C:
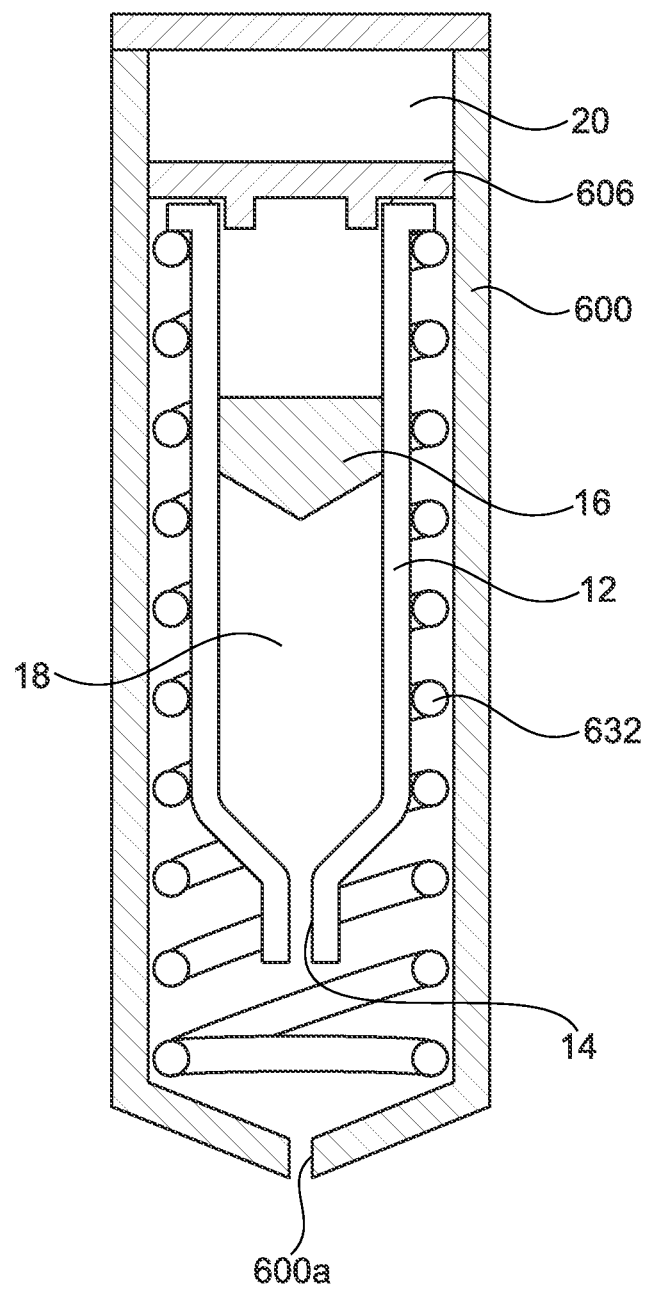
FIG. 14C shows an alternative embodiment in accordance with the present invention includes a first trigger in the form of a moveable piston and a second trigger in the form of a retraction spring.

FIG. 14C shows a further alternative embodiment according to the present invention. The embodiment of FIG. 14C is identical to that of FIG. 14A but additionally includes a retraction spring 632. As the moveable piston 606 is caused to move axially forwardly due to vapor pressure in the second chamber 20, the retraction spring 632 is compressed and provides an axially rearward biasing force against the syringe barrel 12. If and when the vapor pressure in the second chamber 20 drops below a predetermined threshold such that the axially forward force applied on the syringe barrel 12 by the moveable piston 606 is less than the axially rearward force applied on the syringe barrel 12 by the retraction spring 632, the syringe barrel 12 (and any needle attached thereto) will be caused to move axially rearwardly. This may occur, for example, at the end of delivery so as retract a needle from an injection site. The reduction in pressure in the second chamber 20 may occur, for example, as a result of venting of propellant from the second chamber 20.

In any embodiment, there may be several triggers and several resulting actions that occur at different times, where each trigger causes a particular action. This may include, as described above in relation to FIG. 14C, the action of first moving a needle (by movement of the syringe barrel) from a non-exposed position within a housing to an exposed position out of the housing, and then, secondly, moving the needle from the exposed position to a non-exposed position.

In accordance with certain embodiments of the present invention, any resistive moveable component (including but not limited to a moveable piston) may be used as a trigger for causing an action, where the trigger is activated (and the action is triggered) when the second chamber 20 is in fluid communication with the resistive moveable component so that the pressure in the second chamber 20 is acting on the resistive moveable component, and when the pressure in the second chamber 20 is sufficiently high so as to be capable of moving the resistive moveable component. Movement of the resistive moveable component may, amongst other actions, cause (either forward or rearward) movement of the syringe barrel 12 relative to a housing, or the movement of a needle shield to a protecting position where the needle is not exposed and the risk of needle stick injury is reduced.

The resistive moveable component may be any suitable component that moves when subjected to a sufficient pressure. In alternative embodiments, the resistive moveable component may comprise an expandable component that expands in response to an increase in pressure above a threshold pressure. In one example, the expandable component may be expandable bellows. In another example, the expandable component may be an inflatable component. In another example, the resistive movable component may comprise a bi-stable diaphragm that is movable between a first configuration and a second configuration in response to a pressure above a threshold pressure.

FIGS. 15A and 15B show another example in accordance with embodiment of the present invention. In FIGS. 15A and 15B, the resistive movable component comprises expandable bellows 608. FIG. 15A shows the expandable bellows 608 in a non-expanded configuration, and FIG. 15B shows the expandable bellows 608 in an expanded configuration. The expendable bellows 608 expand when the pressure in the second chamber 20 reaches a threshold pressure. By expanding, the expandable bellows 608 cause the syringe barrel 12 to move axially forwardly within the housing 600. The expandable bellows 608 are preferably affixed to the housing 600 at a rear end of the expandable bellows 608 and are preferably affixed to the syringe barrel 12 at a forward end of the expandable bellows 608. In a preferable embodiment, the expandable bellows 608 are pre-formed bellows that permit a space-efficient arrangement within the housing 600. Preferably, the pre-formed bellows have a very small (preferably zero) dead volume when in the non-expanded configuration. In the embodiment shown in FIGS. 15A and 15B, the forwardmost position of the syringe barrel 12 in the housing 600 is determined by the axial length of the expandable bellows 608 in the expanded configuration.

FIGS. 16A and 16B show an alternative embodiment, where expandable bellows 610 are also used to cause axial movement of the syringe barrel 12 within the housing 600. In contrast with the embodiment of FIGS. 15A to 15B, in the embodiment of FIGS. 16A and 16B, the forwardmost position of the syringe barrel 12 within the housing 600 is determined by a shoulder 600b of the housing which abuts the finger flange 12a of the syringe barrel 12 so as to prevent further axially forward movement of the syringe barrel 12 relative to the housing 600. FIG. 16A shows the expandable bellows 610 in a non-expanded configuration, and FIG. 16B shows the expandable bellows 610 in an expanded configuration and the finger flange 12a in abutment with the shoulder 600b of the housing 600.

FIGS. 17A and 17B show a further alternative embodiment of the present invention. In the embodiment of FIGS. 17A and 17B, the resistive moveable component comprises a bi-stable diaphragm 612 that is moveable between a first configuration as shown in FIG. 17A and a second configuration as shown in FIG. 17B. In the second configuration, the syringe barrel 12 is more axially forwards relative to the housing 600 in comparison with the first configuration. The a bi-stable diaphragm 612 are attached to the housing 600 and are also attached, via an attachment collar 614, to the syringe barrel 12. In alternative embodiments, the a bi-stable diaphragm 612 may be connected directly to the syringe barrel 12. In the specific embodiment shown in FIGS. 17A and 17B, the attachment collar 614 has a central bore 618 running therethrough and the housing 600 has a plug element 616 protruding therefrom, where the plug element 616 is disposed within the bore 618 when the a bi-stable diaphragm 612 is in the first configuration so that propellant is substantially prevented from passing from the propellant source to act on the stopper 16. In contrast, when the a bi-stable diaphragm 612 is in the second configuration, the plug element 616 is no longer disposed in the bore 618 such that vapor pressure in the second chamber 20 may act on the stopper 16 in order to move the stopper axially forwardly and expel medicament.

One advantage of the bi-stable diaphragm 612 is that there is no frictional effect. Instead the resistance to movement is determined by the stiffness of the bi-stable diaphragm 612. Therefore, the bi-stable diaphragm 612 moves from the first configuration to the second configuration when the pressure in the second chamber is sufficient to overcome the stiffness of the bi-stable diaphragm and cause the movement. In doing so, the syringe barrel 12 is moved relative to the housing 600.

In alternative embodiments, the plug element 616 and bore 618 may not be present. Such features are examples of how events may be sequenced using pressure in the second chamber 20. As described above, any valve or other hole that opens may be used to sequence events from the pressure of the second chamber 20.

The embodiments described above in relation to FIGS. 14A to 17B all relate to a resistive moveable component that moves in an axial direction to cause an action. In accordance with certain embodiments of the present invention, movement of the resistive moveable component in other (i.e. non-axial directions) may be used to cause the further actions. For example, a radial movement of a resistive moveable component may be used to cause a further action. In particular, a radial movement may be used to de-latch a component such that a biasing element may act to cause an axial movement. As examples, the axial movement may be in respect of the syringe barrel 12 or may be an additional component such as a needle shield.

FIG. 18 shows an example of a resistive moveable component that moves in a radial direction to cause a further action. In FIG. 18, a hollow rod 620 (having a central bore) has an inflatable sleeve 622 surrounding a part of the outer circumference of the rod 620. The hollow rod has one or more radial apertures (not shown) passing through the rod 620 establishing a fluid connection with the central bore). The hollow rod 620 is in fluid communication with the second chamber 20 (not shown) such that the pressure of the second chamber 20 may act on the inflatable sleeve 622 via the radial apertures. When the pressure in the second chamber 20 reaches a threshold pressure that is sufficient to cause the inflatable sleeve 622 to inflate, the inflatable sleeve 622 does so and expands in one or more radial directions. The inflatable sleeve 622 may include pockets 622a that are preformed cavities or simply made of a material that is less resistive to inflation such that the pockets 622a are preferentially inflated over the remainder of the inflatable sleeve 622. The radially expanding inflatable sleeve 622 may be used to cause a further action. In one embodiment, for example, the radially expanding inflatable sleeve may cause a mechanical latch to disengage (i.e. de-latch) and permit a further action such as allowing a biasing member (e.g. a springe held in compression) to cause an axial movement.

In alternative embodiments in accordance with the present invention, other resistive moveable components may be caused to move radially in response to the pressure in the second chamber 20 satisfying a predetermined condition, and in turn causing a further action. For example, amongst other possibilities, the radially moveable resistive moveable component may be a piston, expanding bellows or a bi-stable diaphragm. The radially moveable resistive moveable component may, by a camming action, cause a direct axial movement of another component.

Similarly, in other embodiments within the scope of the present invention, a resistive moveable component may move axially and, by a camming action, cause a radial movement of another component. Such radial movement may then cause a de-latch, for example, to permit a further action.

An example of an embodiment of the present invention where the pressure in the second chamber 20 causes a series of axial and radial movements in described below in relation to FIGS. 19A to 19C. FIG. 19A shows a device 623 that includes a syringe barrel 12 having a stopper 16 (in accordance with the present invention) disposed within a housing 600. The device 623 has a propellant source 628 in accordance with the present invention, a release collar 626 disposed within the housing 600, a piston 630 disposed in the syringe barrel 12 axially rearwardly of the stopper 16, and a retraction spring 632 held in compression.

In the specific embodiment shown in FIGS. 19A to 19C, the propellant source 628 is a latching can that is capable of dispensing liquid propellant for boiling outside of the propellant source 628 so as to provide a vapor pressure to the second chamber 20. Once opened, the latching can 628 is latched open so that the entire contents of propellant is dispensed therefrom. In other embodiments, other propellant sources may be used provided that they are capable of dispensing liquid propellant for boiling outside of the propellant source and providing a vapor pressure to the second chamber 20.

In the initial position shown in FIG. 19A, the compressed retraction spring 632 is biased against the release collar 626 and the housing 600. However, feet 626a of the release collar 626 are latched against a part of the housing 600 preventing relative axial movement between the release collar 626 and the housing 600.

The device 623 is actuated when the latching can 628 is caused to move axially forward begins to dispense liquid propellant via a bore 630a in the piston 630 disposed in the syringe barrel 12. The piston 630 is sealed against the syringe barrel 12 by a seal 631 so that the only fluid path across the piston 630 is via the bore 630a.

As liquid propellant is dispensed from the latching can 628, it boils in the second chamber to produce a vapor pressure that acts on the stopper and causes it to move axially forwardly in the syringe barrel 12 and expel medicament. In FIG. 19B, the stopper 16 has already moved axially forwardly and has begun to expel medicament.

The increasing pressure of the second chamber 20 acts axially rearwardly against the piston 630 and the latching can 628 (as well as axially forwardly against the stopper 16). The axially rearwardly acting force on the latching can 628 initially moves the latching can 628 to a latching position where the can 628 remains in a permanent dispensing position. Additionally, the piston 630 moves axially rearwardly under the pressure of the second chamber 20.

FIG. 19B shows the device 623 after the piston 630 and latching can 628 have moved axially rearwardly due to the pressure in the second chamber 20. The seal 631 maintains a seal between the piston 630 and the syringe barrel 12 but permits axial sliding of the piston 630 relative to the syringe barrel 12 provided that the frictional forces therebetween are overcome.

As a result of this axially rearward movement, an outer tapered surface acts against a radially inwardly projecting tag 626b of the release collar 626 and causes the feet 626a of the release collar to delatch (i.e. move in a radial direction) from the housing 600. The retraction spring 632 is then free to expand and cause the release collar 626 to move axially rearwardly with respect to the housing 600.

The syringe barrel 12 is fixed relative to the release collar 626 and is caused to move axially rearwardly relative to the housing 600 as a consequence of the axially rearwardly moving release collar 626.

FIG. 19C shows the device 623 where a syringe barrel 12 has been caused to move axially rearwardly under the influence of the retraction spring 632. As a result, any needle attached to the barrel 12 will have been fully withdrawn within the housing 600 such that the risk of needle stick injury is reduced.

An alternative specific embodiment of the invention is described with reference to FIGS. 20 and 21. FIG. 20 shows a syringe 10' in accordance with an embodiment of the present invention. The syringe 10' has a barrel 12 that has an outlet 14 through which a needle 15 extends. A stopper 16 is disposed in the barrel 12 and is axially moveable therein subject to experiencing a sufficient axial force. The stopper 16 defines and separates a first chamber 18 and a second chamber 20 where the first chamber 18 is axially forwards of the stopper 16 and is configured for containing a substance such as medicament, and in particular, a liquid medicament. The second chamber 20 is axially rearwards of the stopper and is configured to receive propellant from a propellant source, which in the embodiment of FIGS. 20 and 21 is a container 21 which comprises a rupturable wall 24 defining a third chamber containing propellant.

The syringe 10' has a rupturing portion 100 which comprises a blade 102 pivotally mounted on a pivot 104 so that the rupturing portion 100 is pivotable between a non-rupturing position where the rupturing portion 100 does not rupture the container 21 (as shown in FIG. 20) and a rupturing position where the rupturing portion 100 ruptures the container 21 (as shown in FIG. 21). The rupturing portion 100 is moveable between the rupturing position and the non-rupturing position by axial movement of a beam 106 that applies a torque to the rupturing portion 100 so as to cause it to rotate about the pivot 104. The beam 106 has a cut-out 106a that receives the rupturing portion 100 and applies torque to the rupturing portion 100 as the beam 106 moves axially, where the cut-out 106a permits rotation of the rupturing portion 100. The beam 106 is connected at a rear end to a push button 108 at the rear of the syringe 10' that may be depressed to axially move the beam 106 and cause rotation of the rupturing portion 100 so as to move it to the rupturing position. The button 108 and/or beam 106 and/or rupturing portion 100 may be biased so that the rupturing portion 100 is biased towards the non-rupturing position and resides in the non-rupturing position when no force (or insufficient force) is applied to the push button 108.

The syringe 10' additionally includes a moveable needle shield 112 that is moveable between a first retracted position (as shown in FIG. 20) in which the needle 15 is exposed, and a second extended position (as shown in FIG. 21) in which the needle 15 is surrounded and is not exposed. Forward movement of the needle shield 112 is limited by a flanged rear end 112a of the needle shield 112 that abuts an inward flange 110b on the front end of a housing 110 of the syringe 10' when the needle shield 112 is in its second extended position.

The needle shield 112 has axially rearwardly extending legs 114 that are frictionally engageable in a friction coupling 115. The friction coupling 115 prevents movement of the needle shield 112 between the first and second position unless a force is applied that is sufficient to overcome the friction of the friction coupling 115. In the specific embodiment shown in FIGS. 20 and 21, the friction is provided by o-ring seals 116 in the friction coupling 115.

The rear end of the barrel 12 is open so that the second chamber 20 extends out of the barrel 12 and is limited and defined by the housing 110 surrounding the barrel 12. The o-ring seals 116 seal against the legs 114 so that they too contribute to the seal between the second chamber 20 and the atmosphere external to the syringe 10'. In alternative embodiments, the sealing and frictional features of the o-ring seals 116 may be provided by two or more components.

In use, the user places the forward end of the syringe 10' against the injection site (so that the needle 15 pierces the injection site) and actuates the syringe 10' by depressing the button 108. This action causes the beam 106 to move axially forwards, which in turn causes the rupturing portion 100 to rotate about pivot 104 to move from the non-rupturing position to the rupturing position. In the rupturing position, the rupturing portion 100 ruptures the rupturable wall 24 to release propellant into the second chamber 20. As described above, the release of propellant into the second chamber causes the stopper 16 to move axially forwardly to expel medicament (or other substance present) out of the outlet 14 (which in the embodiment shown in FIGS. 20 and 21 is via the needle 15).

The legs 114 extend rearwardly through the friction coupling 115 into the second chamber 20. Consequently, the legs 114 experience the pressure caused by the boiling propellant. Once the pressure in the second chamber 20 acting on the legs 114 is sufficient to overcome the friction of the friction coupling 115, the legs 114 and the remainder of the needle shield 112 begin to move axially forwardly.

Initially, the pressure acting on the legs 114 causes the needle shield 112 to be biased axially forwardly against the injection site (e.g. the patient's skin) so that the injection site prohibits movement of the needle shield 112 to the second position. With the legs 114 engaged in the friction coupling 115, the second chamber 20 is entirely sealed and the pressure therein will remain. At the end of the delivery sequence, when all of the medicament in the first chamber 18 has exited the outlet 14, the user may remove the syringe 10' from the injection site. Since the needle shield 112 will still be biased axially forwardly by the pressure in the second chamber 20, as the syringe 10' is moved away from the injection site, the needle shield 112 will move further axially forwardly towards the second position. Eventually, the needle shield 112 will reach its second extended position and the needle 15 will be surrounded and protected by the needle shield 112. In this second position, further axially forward movement of the needle shield 112 is prevented by the abutment between the flanged rear end 112a of the needle shield 112 and the inward flange 110b on the front end of a housing 110 of the syringe 10'.

At or before this position, the legs 114 have travelled axially through the friction coupling 115 and are no longer engaged by the friction coupling 115 (as shown in FIG. 21). When engaged in the friction coupling 115, the legs 114 are flexed in an inwardly radial direction by the friction coupling 115 in a first radial position. Therefore, when the legs 114 move axially forwardly by a sufficient amount that they are no longer engaged in the friction coupling 115, the legs 114 flex radially outwardly (by elastic relaxation) to a second radial position. In the second radial position, the legs 114 (and hence the remainder of the needle shield 112) are prevented from moving axially rearwardly due to abutment between the legs 114 and a step 110c of the housing 110. In the embodiment shown in FIGS. 20 and 21 (but not necessarily all embodiments within the scope of the present invention), the step 110c of the housing 110 forms part of an aperture 110a that fluidly connects the friction coupling 115 to the atmosphere external to the syringe 10'. In alternative embodiments, the step 110c and the aperture 110a may be entirely independent features. The abutment between the legs 114 and the step 110c forms a "lock-out" mechanism that prevents or limits subsequent rearward axial movement of the needle shield 112. Other suitable lock-out mechanisms may be used in place of the specific arrangement described to achieve this result, within the scope of the present invention.

When the legs 114 are not engaged in the friction coupling 115, the seals 116 no longer seal against the legs 114 such that the friction coupling 115 no longer seals the second chamber 20. Thus, when the legs 114 are not engaged in the friction coupling 115, the second chamber 20 is fluidly connected to the atmosphere external to the syringe 10' via the friction coupling 115 and the aperture 110a such that gas in the second chamber 20 can vent out (as shown by arrow 1000 in FIG. 21). As the gas vents out, the pressure in the second chamber 20 equalises with the pressure of the atmosphere external the syringe 10'. This is particularly advantageous since if the syringe is pulled away from an injection site before the entire dose of medicament has been delivered, the pressure in the second chamber 20 would cause the needle shield 112 to move to its second position which in turn initiates the venting of the propellant gas in the second chamber 20 which consequently ceases movement of the stopper 16 and ends the delivery of medicament. Thus, the syringe 10' may be removed during an injection and automatically stop delivering medicament through the needle 15.

The legs 114 are resistive moveable components that form the trigger of the above-described embodiment insomuch as the legs 114 cause movement of the needle shield 112. The trigger is activated when the pressure in the second chamber 20 is sufficient so as to overcome the frictional forces of the friction coupling 115 so as to permit movement of the legs, and, therefore, the needle shield 112.

The cross sectional area of the legs 114 that are exposed to gas pressure in the second chamber 20 may be varied in alternative embodiments to tailor the force required to activate the trigger.

In embodiments alternative to that described above in relation to FIGS. 20 and 21, other propellant sources may be used that dispense a liquid propellant that boils so as to provide a vapor pressure to the second chamber 20.

In alternative embodiments to that described in relation to FIGS. 20 and 21, the frictional coupling may be provided by a lip seal that seals directly against the legs. In further alternative embodiments, the legs may include seals and form pistons that seal against a surrounding surface, where pressure acting on the pistons may cause the pistons to move provided that the pressure is sufficient to overcome the friction and stiction of the pistons. The overall size of the device will be influenced by the size of the seal which will be optimized for the length of travel of the rod, the friction, stiction and pressure in the system.

There may be any number of rods (and associated seals) present and they may be arranged anywhere relative to the syringe barrel 12 provided that the rods are moveable by the vapor pressure acting on the stopper 16. The rods may cause the movement of a needle shield or any other suitable component as part of a useful action. For example, the movement of the rods may merely cause the movement of another component which leads to a useful action being performed. Any number of intermediate but consequent interactions may occur between the movement of the rods and the resulting useful action.

The seals chosen should preferably have as low friction and stiction as possible but also provide an effective seal against the propellant pressure. Lips seals are particularly preferable and are particularly suitable for use with moulded components where manufacturing tolerances need to be considered. In a given device, the seals are preferably optimized for the length of axial travel required (e.g. by the legs 114), the friction and stiction of the resistive moveable component in relation to the seals. The size of the seals chosen will influence the size of the overall device.

An alternative embodiment in accordance with the present invention is shown in FIGS. 22A to 22E. In this embodiment, a propellant housing 634 is sealed by seals 636 to a rear end of the syringe barrel 12. The propellant housing 634 has a vent hole 642 that may be any shape, size or configuration provided that it permits vaporized propellant to pass therethrough. In certain embodiments, the vent hole is preferably small so as to limit the venting rate. Disposed in the syringe barrel 12 is a stopper 16 which includes a rod extending axially rearwardly through the propellant housing 634. The propellant housing 634 has a narrowed forward portion 638, however the narrowed forward portion has a diameter that is larger than the diameter of the rod 644 such that vaporized propellant may pass through the annulus between the rod 644 and the narrowed forward portion 638. Disposed around the rod 644 is an axially moveable seal 640. The axially moveable seal 640 is axially moveable relative to the rod 644 and seals against an inside surface of the propellant housing 634. The axially moveable seal 640 does not seal to the rod 644 entirely (or not at all) and permits the passage of vaporized propellant across the axially moveable seal (i.e. from axially rearward of the axially moveable seal 640 to axially forward of the axially moveable seal 640).

In use, liquid propellant is provided from a propellant source to provide a vapor pressure in the second chamber 20 that extends between the propellant source and the stopper 16. In the configuration shown in FIG. 22A, the axially moveable seal 640 is sealing the vent hole 640 from the second chamber 20 such that propellant cannot escape from the second chamber 20 via the vent hole. In accordance with the present invention, the vapor pressure in the second chamber 20 rises as the liquid propellant boils and the stopper 16 begins to move axially forwardly to begin to expel medicament from the first chamber 18. As the stopper 16 moves axially forwardly, the rod 644 slides axially through the axially moveable seal 640 that remains stationary, sealing the vent hole 640.

As shown in FIG. 22B, a flange 646 projects from a rear end of the rod 644. When the stopper 16 reaches an axial position in the syringe barrel 12 where the flange 646 contacts the axially moveable stopper 640, further axially forwardly movement of the stopper 16 causes the flange 646 to move the axially moveable seal 640 axially forwardly and begin to open the vent hole 642. FIG. 22B shows the vent hole 642 partially opened by the axially forwardly advancing axially moveable seal 640. As the vent hole 642 opens, propellant in the second chamber 20 begins to escape and the vapor pressure in the second chamber 20 begins to decrease. The rate of the decrease in vapor pressure in the second chamber 20 will depend on the size of the vent hole 642, the thermodynamics of the system (the temperature and pressure of the propellant in particular, and the speed at which the vent hole is opened (i.e. change from fully closed to fully open).

FIG. 22C shows the axial position of the stopper 16 corresponding to the configuration shown in FIG. 22B. As can be seen in FIG. 22C, the stopper 16 is not at its axially forwardmost position within the barrel 12, and the first volume 18 still contains medicament.

In the embodiment shown in FIGS. 22A to 22E, the vent hole 642 is sized so that when the vent hole 642 is first opened, a sufficient amount of propellant remains for a long enough time in the second chamber 20 to move the stopper 16 to its forwardmost position in the syringe barrel 12.

FIG. 22D shows the axially moveable seal 640 in an axial position that is entirely forward of the vent hole 642 such that the vent hole is fully open. FIG. 22E shows the axial position of the stopper 16 corresponding to the configuration shown in FIG. 22D.

Figure 23:
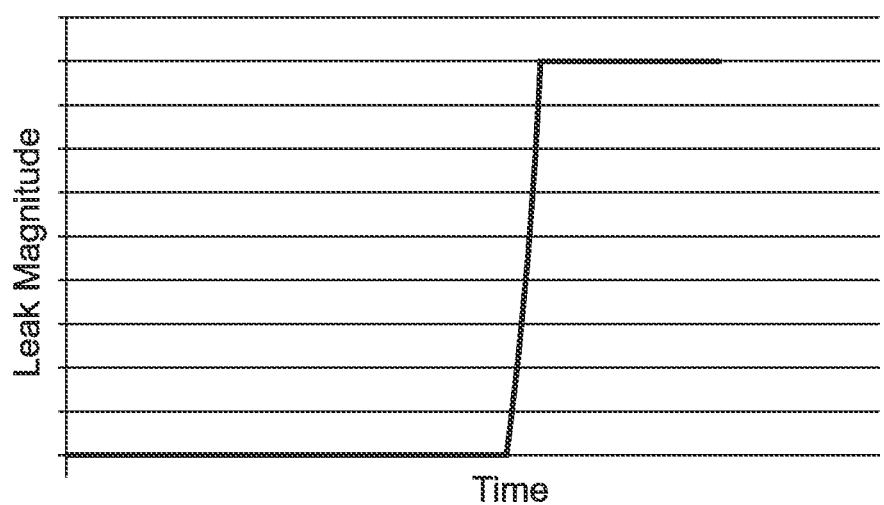
FIG. 23 shows a plot of leak magnitude versus time for the syringe shown in FIGS. 22A to 22E.

FIG. 23 shows the leak magnitude of the embodiment of FIGS. 22A to 22E as the axially moveable seal 640 moves axially and opens the vent hole 642.

Once the vapor pressure in the second chamber 20 drops below a predetermined threshold due to the venting, a trigger (for example, a biasing member acting against the second chamber 20) may cause an action (e.g. initiate retraction of the syringe and needle from an exposed position to a non-exposed position). By restricting the rate of venting through the vent hole 642 (e.g. by choice of size of vent hole 642), it can be ensured that the entire dose of medicament is delivered before the reduction in vapor pressure in the second chamber 20 causes the trigger to trigger an action. This is particularly beneficial due to manufacturing tolerances and the resulting uncertainty regarding the precise axial position of the stopper 16 in the syringe barrel 12.

FIGS. 24A and 24B show examples corresponding to the embodiment of FIGS. 22A to 22E. In FIG. 24A, the propellant housing has an inlet 634a at a rear end, where the inlet 634a is fluidly connected to a propellant source 628. In use the propellant source 628 provides liquid propellant to the second chamber 20, which, in the embodiment of FIG. 24A, is the volume between the propellant source 628 and the stopper 16. In FIG. 24B, the rear end of the propellant housing 634 is sealed and, instead, the propellant housing 634 has a side inlet 634a. In any embodiment, there must be a fluidic flow path from the propellant source 628 that permits the vapor pressure in the second chamber 20 to act on and cause the stopper 16 to move.

Figure 25A:
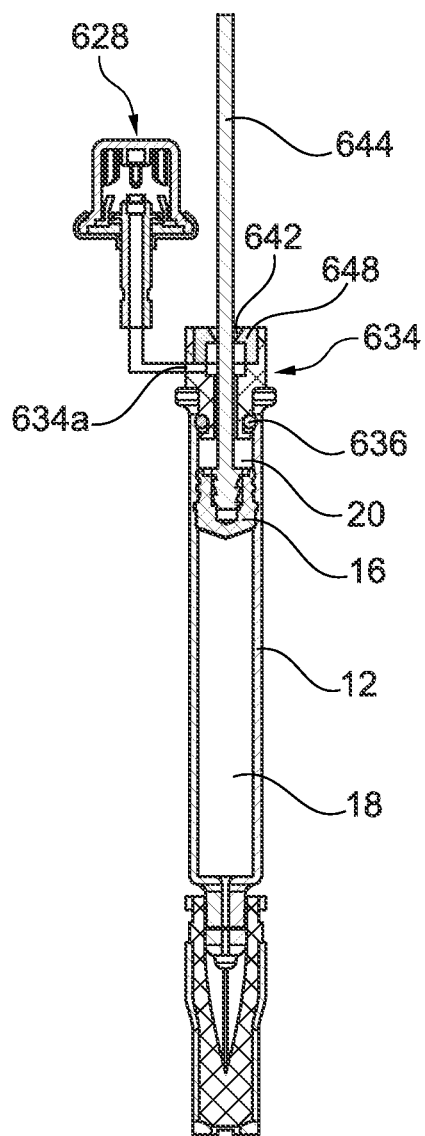
FIGS. 25A and 25B show a syringe in accordance with an alternative embodiment of the present invention that includes a vent hole, where in FIG. 25A the vent hole is closed, and in FIG. 25B the vent hole is open.
Figure 25B:
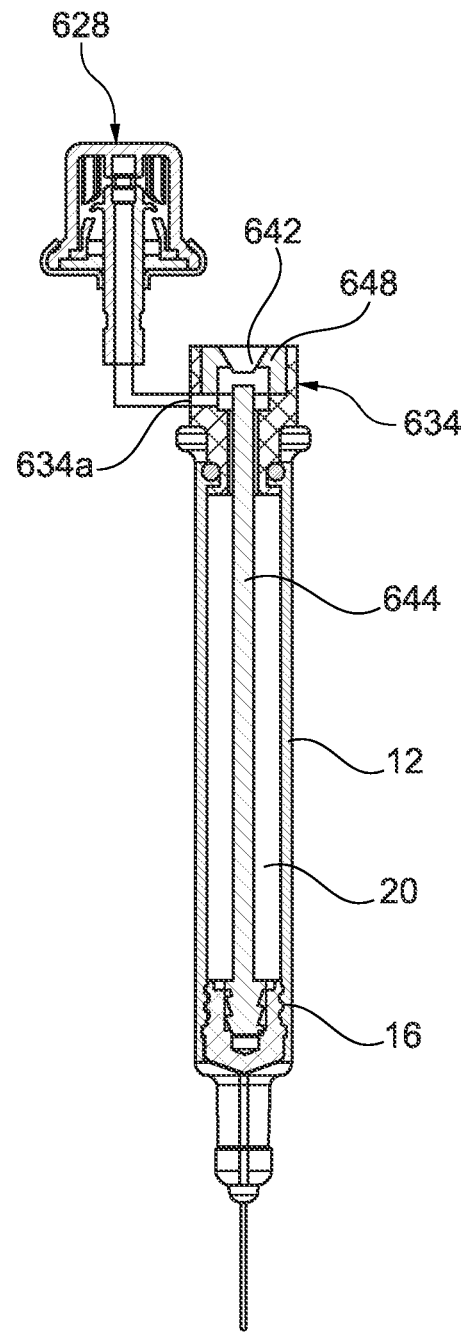

In the alternative embodiment shown in FIGS. 25A and 25B, the propellant housing 634 has a vent hole 642 located at a rear end such that the rod 644 initially protrudes therethrough. FIG. 25A shows the device in an initial configuration prior to delivery of medicament. In this initial configuration, a rod seal 648 seals the propellant housing 634 to the rod 644 so as to block the vent hole 642.

In use, a propellant source 628 dispenses liquid propellant through an inlet 634a of the propellant housing 634 into the second chamber 20 where it may boil and cause the stopper 16 to move axially forwardly. The advancing stopper 16 causes the rod 644 to slide axially forwardly through the rod seal 648. Throughout this movement, the combination of the rod seal 648 and the rod 644 continues to seal the vent hole.

When the stopper 16 reaches its axially forwardmost position in the syringe barrel 12, as shown in FIG. 25B, the rear end of the rod 644 will have moved to an axial position where the vent hole 642 is no longer sealed by the combination of the rod seal 648 and the rod 644, and venting of propellant from the second chamber 20 begins. The movement of the rod 644 may cause the vent hole 642 to be opened entirely, or it may create a restricted flow path.

Figure 26:
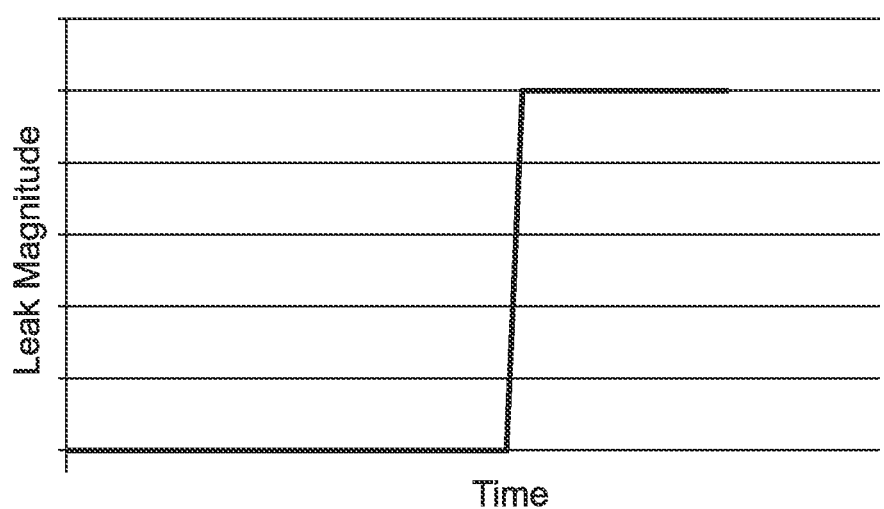
FIG. 26 shows a plot of leak magnitude versus time for the syringe shown in FIGS. 25A and 25B.

FIG. 26 shows the leak magnitude of the embodiment of FIGS. 25A and 25B as the rod 644 moves axially to open the vent hole 642. In the embodiment of FIGS. 25A and 25B, the size of the vent hole 642 is determined by the diameter of the rod 644 and is therefore larger than the smaller vent hole 642 of the embodiment of FIGS. 22A to 22E, 24A and 24B. Consequently, the leak magnitude shown in FIG. 26 increases more rapidly than the leak magnitude shown in FIG. 23.

Figure 27A:
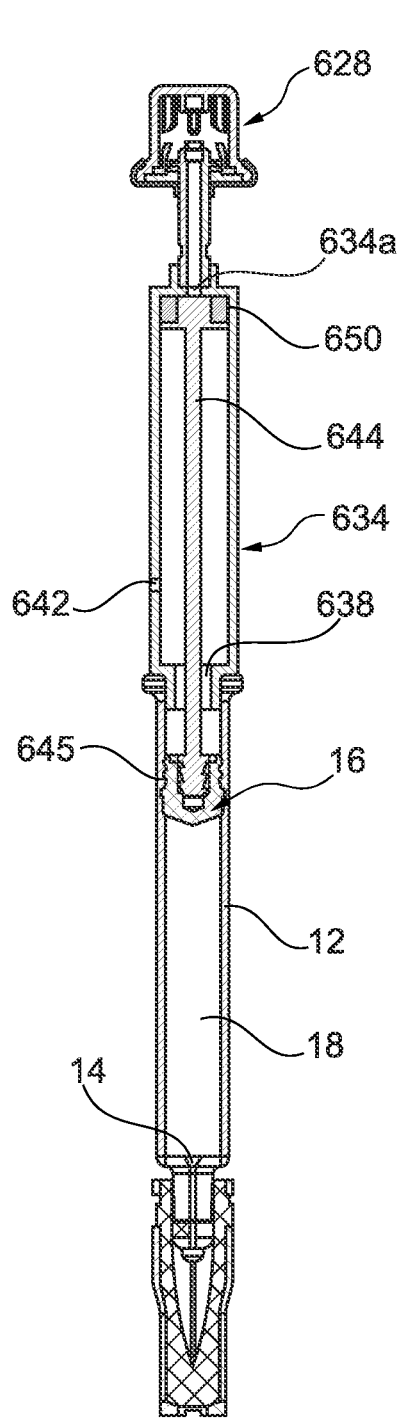
FIGS. 27A and 27B show a syringe in accordance with an alternative embodiment of the present invention that includes a vent hole, where in FIG. 27A the vent hole is closed, and in FIG. 27B the vent hole is open.
Figure 27B:
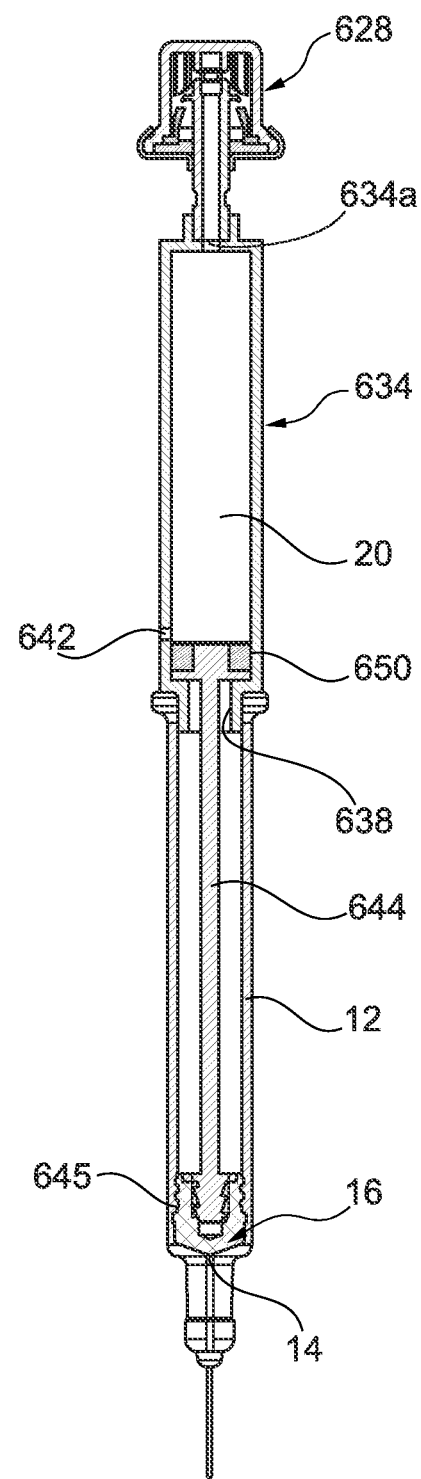

A further alternative embodiment is shown in FIGS. 27A and 27B in which the stopper 16 includes a bung 645 at a forward end and a rod 644 extending axially rearwardly from the bung 645 parallel to the length of the syringe barrel 12. The rod 644 extends out of the syringe barrel 12 and into a propellant housing 634 that is disposed at a rear end of the syringe barrel 12 and is sealed thereto. Since the rod 644 and the piston seal 650 are part of the stopper 16 and the piston seal 650 seals against the propellant housing, vapor pressure acting on the rod 644 (and piston seal 650) causes axial movement of the stopper 16 so as to expel medicament from the first chamber 18. In this sense, the second chamber 20 is defined as the volume extending between a propellant source 628 and the rear end of the rod 644 (which forms part of the stopper 16) that is sealed against the syringe barrel 12. The propellant housing 634 has an inlet 634a in fluid communication with the propellant housing 628 and further includes a vent hole 642 that is positioned so as to be in fluid communication with the second chamber 20 when the stopper 16 is in its forwardmost axial position in the syringe barrel 12 (i.e. at the end of delivery) as shown in FIG. 27B, or, in alternative embodiments, when the stopper 16 is approaching its forwardmost axial position.

In the configuration shown in FIG. 27A prior to medicament delivery, the vent hole 642 is not in fluid communication with the second chamber 20 and so propellant is not able to vent and, instead, causes axial movement of the stopper 16 (including rod 644). At the end of delivery, as shown in FIG. 27B, the rod 644 and piston seal 650 have moved axially forwardly sufficiently for the vent hole 642 to open and permit venting of propellant from the second chamber 20.

Figure 28:
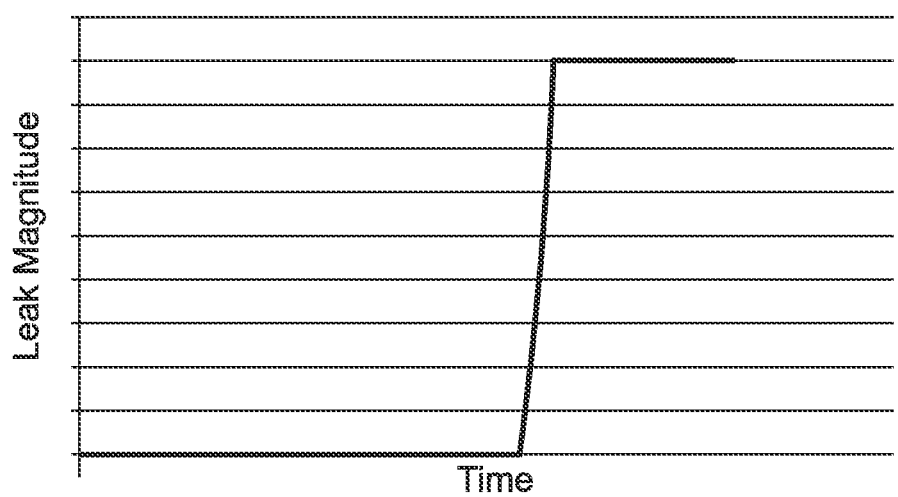
FIG. 28 shows a plot of leak magnitude versus time for the syringe shown in FIGS. 27A and 27B.

FIG. 28 shows the leak magnitude of the embodiment of FIGS. 27A and 27B as the rod 644 moves axially to open the vent hole 642. As with the embodiment of FIGS. 22A to 22E, the vent hole 642 may be sufficiently small so as to restrict venting and permit medicament delivery to continue for a time period following initial venting.

Contrasting the embodiment of FIGS. 27A and 27B to that of FIGS. 22A to 22E, the embodiment of FIGS. 27A and 27B will encounter higher frictional forces during medicament delivery due to the presence of the piston seal 650. However, since the vapor pressure acts on the rod 644 and the piston seal 650 which are not limited by the diameter of the syringe barrel 12, a larger surface area is permissible which allow greater delivery forces to be employed.

Figure 29:
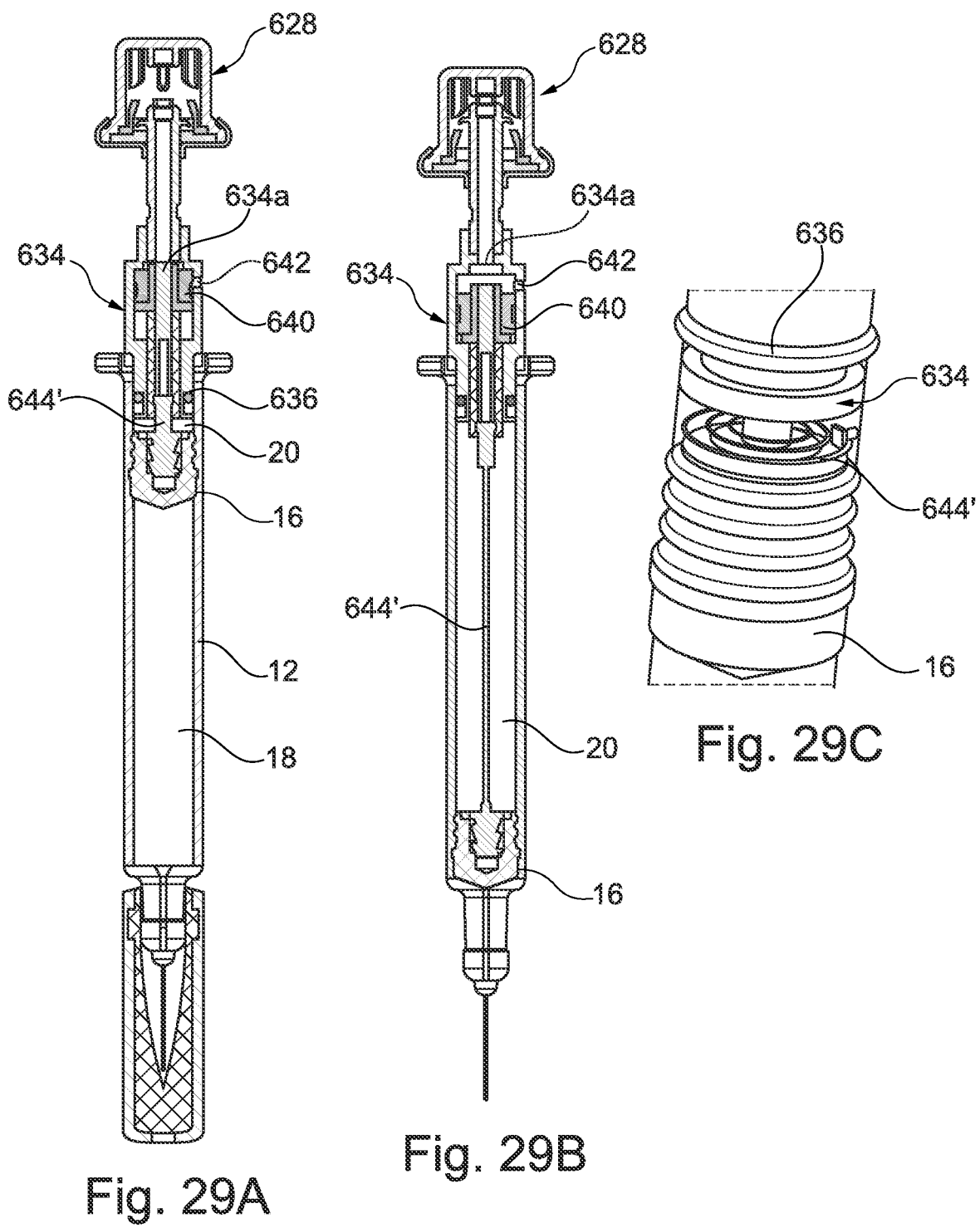
FIGS. 29A and 29B show a syringe in accordance with an alternative embodiment of the present invention that includes a vent hole, where in FIG. 29A the vent hole is closed, and in FIG. 29B the vent hole is open.
FIG. 29C shows a detailed view of part of the syringe of FIGS. 29A and 29B.

The alternative embodiment shown in FIGS. 29A to 29C is very similar to that shown in FIGS. 22A to 22E but for the fact that the stopper 16 is connected to the axially moveable seal 640 by an extendible member 644' rather than a rigid rod. As the stopper 16 moves axially forwardly in the syringe barrel 12, the extendible member 644' extends. As the stopper 16 approaches its axially forwardmost position in the syringe barrel 12, the extendible member 644' extends to its fullest extent and, due to tension, begins to cause axially forward movement of the axially moveable seal 640. Consequently, the axially moveable seal 640 moves to an axial position where the vent hole 642 is opened and permits venting of propellant from the second chamber 20.

FIG. 29C shows a detailed view of an example of a suitable extendible member 644' that is in a coiled configuration. Axial movement of the stopper 16 causes the coil to unwind. Once the coil has fully unwound, the extendible member 644' may apply a downward axial force on the axially moveable seal 640 to open the vent hole 642. The extendible member 644' may be any suitable member that is flexible so as to only apply a force to the axially moveable seal 640 sufficient to move the axially moveable seal 640 when the distance between the stopper 16 and the axially moveable seal 640 substantially equals the maximum length of extendible member 644'. A length of string or similar member may be a suitable extendible member 644'. The string may, for example, be moulded string.

Figure 30:
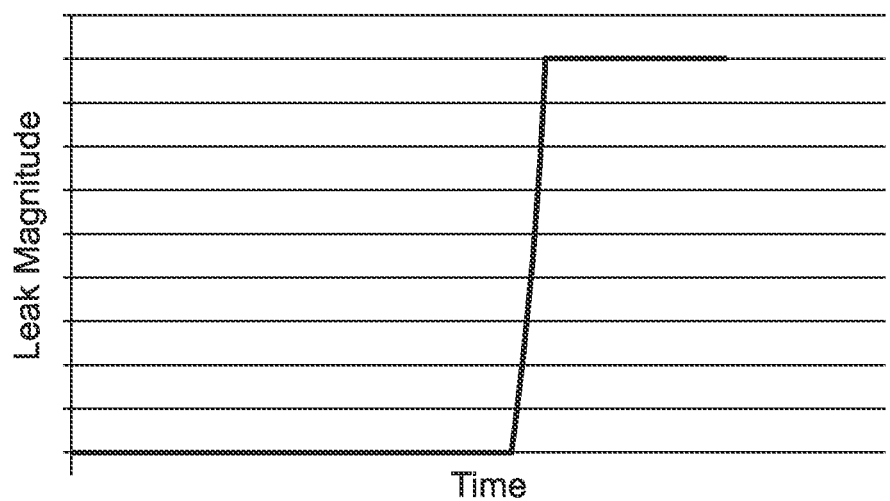
FIG. 30 shows a plot of leak magnitude versus time for the syringe shown in FIGS. 29A and 29B.

FIG. 30 shows the leak magnitude of the embodiment of FIGS. 29A to 29C as the axially moveable seal 640 moves axially and opens the vent hole 642. The leak magnitude shown in FIG. 30 closely resembles that shown in FIG. 23 due to the similarities in the embodiments of FIGS. 22A to 22E and FIGS. 29A to 29C.

Figures 31A, 31B:
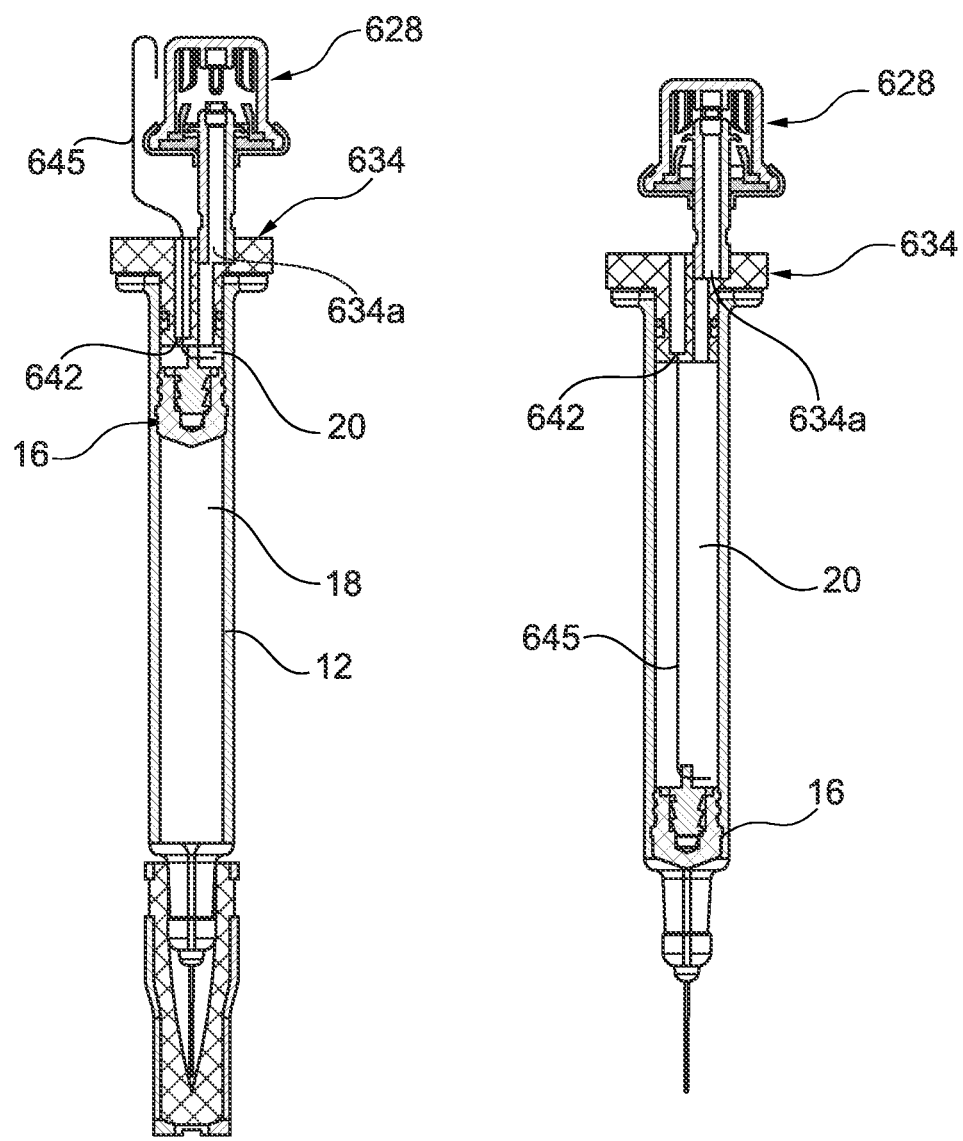
FIGS. 31A and 31B show a syringe in accordance with an alternative embodiment of the present invention that includes a vent hole, where in FIG. 31A the vent hole is occluded, and in FIG. 31B the vent hole is not occluded and is open.

A further alternative embodiment is shown in FIGS. 31A and 31B. In this embodiment, the propellant housing 634 has a vent hole 642 that is open, to a certain extent, prior to propellant being released into the second chamber 20. A flexible member 645 extends axially rearwardly from the stopper 16 and extends through the vent hole 642. The presence of the flexible member 645 in the vent hole 642 does not prohibit propellant venting from the second chamber 20 therethough, however it does limit the rate at which propellant may vent. The absolute size of the vent hole 642 and the relative size of the vent hole 642 relative to the dimensions of the flexible member 645 will determine the rate at which propellant may vent from the second chamber 20. Clearly, it is preferable for the leak rate to be low enough for the propellant remaining to deliver a full dose of medicament.

At the end of medicament delivery when the stopper 16 is at its axially forwardmost position in the syringe barrel 12 as shown in FIG. 31B, the flexible member 645 no longer occludes the vent hole 642 and so permits more rapid venting of any propellant remaining in the second chamber 20. In alternative embodiments, the flexible member 645 may remain in an occluding position when the stopper 16 is in its axially forwardmost position.

Figure 32:
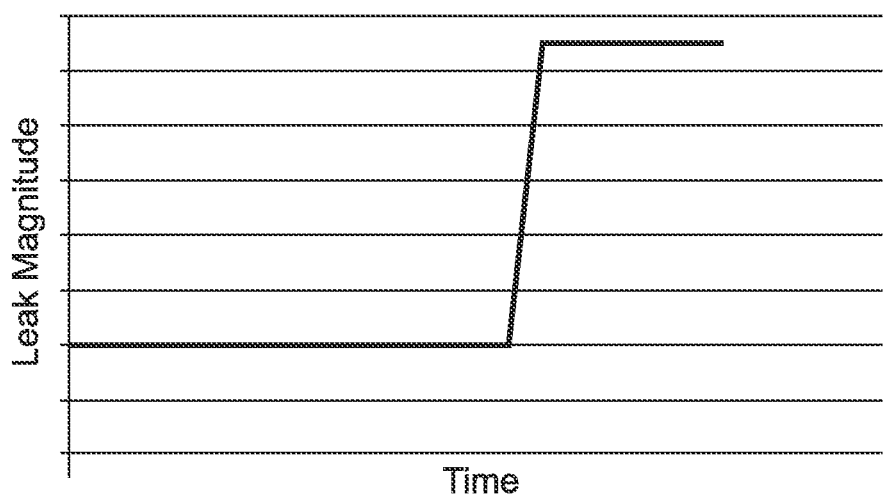
FIG. 32 shows a plot of leak magnitude versus time for the syringe shown in FIGS. 31A and 31B.

FIG. 32 shows the leak magnitude of the embodiment of FIGS. 31A and 31B as propellant vents from the second chamber 20 via the occluded vent hole 642.

Figure 33A:
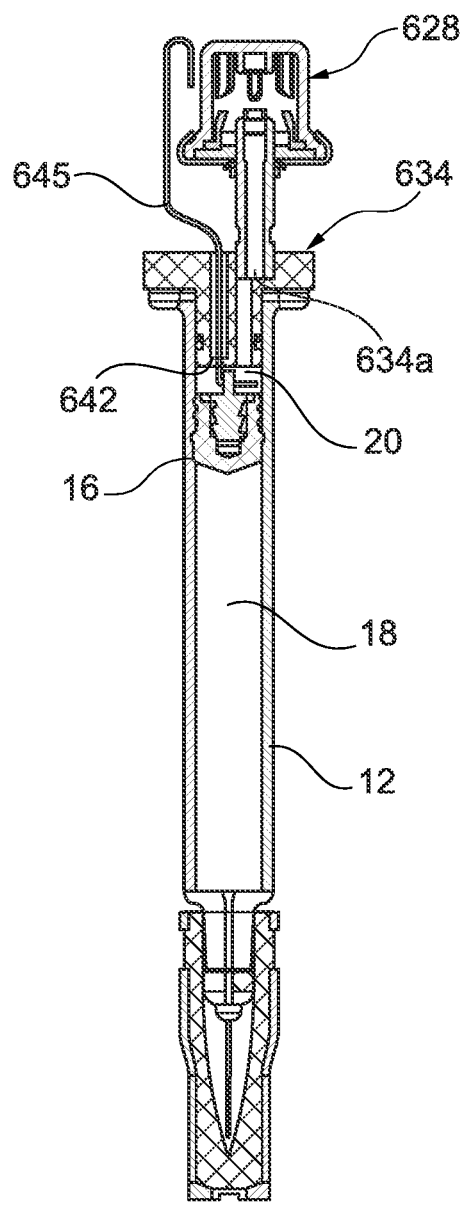
FIGS. 33A and 33B show a syringe in accordance with an alternative embodiment of the present invention that includes a vent hole, where in FIG. 33A the vent hole is occluded, and in FIG. 33B the vent hole is still occluded and the stopper is at its forwardmost axial position in the syringe barrel.
Figure 33B:
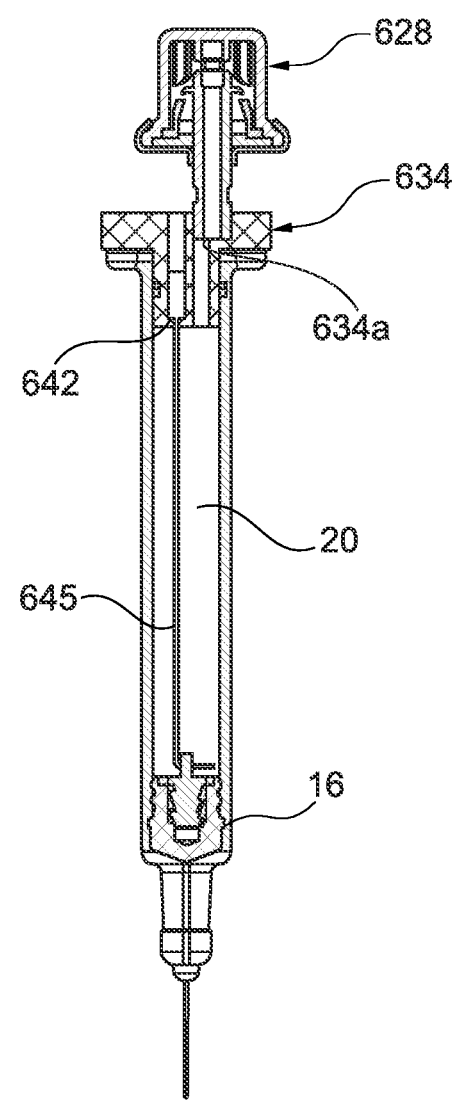

FIGS. 33A and 33B show an embodiment related to that shown in FIGS. 31A and 31B. The embodiment of FIGS. 33A and 33B differs from that shown in FIGS. 31A and 31B in that the vent hole 642 extends axially to a greater extent in the embodiment of FIGS. 33A and 33B. The presence of flexible member 645 in the vent hole 642 therefore provides an occlusion over a greater length and consequently limits venting therethrough to a greater extent compared to the embodiment of FIGS. 31A and 31B.

Figure 34:
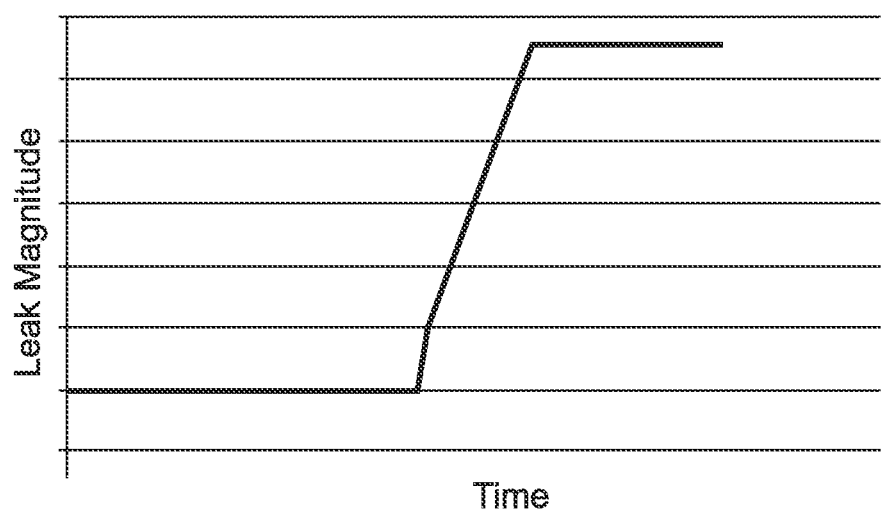
FIG. 34 shows a plot of leak magnitude versus time for the syringe shown in FIGS. 33A and 33B.

This slower leak rate is evident in FIG. 34 where it can be seen that the leak magnitude increases more slowly compared with FIG. 32.

A further alternative embodiment is shown in FIGS. 35A and 35B which is similar to that described above in relation to FIGS. 25A and 25B. The embodiment of FIGS. 35A and 35B differs from that of FIGS. 25A and 25B in that the rod 644 of FIGS. 35A and 35B is flexible so as to permit a reduction in the overall axial length of the device prior to actuation. As shown in FIG. 35A, the part of the flexible rod 644 that is initially disposed outside of the syringe barrel 12 may bend so as remain compact and permit a more compact device. As the stopper 16 moves axially forwardly, the flexible rod 644 is drawn through the rod seal 648 and eventually moves to a position where it no longer prevents venting of propellant through the vent hole 642 as shown in FIG. 35B. The rod 644 may be hollow to permit flexing.

In accordance with alternative embodiments of the present invention, the predetermined condition may be satisfied when the pressure in the second chamber relative to the pressure in a reference chamber substantially equals a predetermined ratio. This predetermined ratio may be 1:1 such that the pressure in the second chamber is substantially equal to the pressure in the reference chamber. Alternatively, any other ratio may define the predetermined condition relative to a reference chamber. When the predetermined condition is satisfied, a trigger may trigger an action.

In one embodiment, the second chamber is fluidly connected to a reference chamber via a restricted fluid pathway. The reference chamber may be a further chamber or a sub-chamber of the second chamber. The second chamber and the reference chamber may share a wall in the form of a deformable diaphragm where the diaphragm is connected to a moveable component. The second chamber, reference chamber and diaphragm may be configured such that when the predetermined condition is satisfied (e.g. when the pressure in the second chamber equals the pressure in the reference chamber), the diaphragm is caused to deform and move the moveable component. In one embodiment, the moveable component may be part of a valve or move part of a valve to cause venting from one of the second chamber and reference chamber. Given that the second chamber is fluidly connected to the reference chamber via the restricted fluid pathway, venting in one of the second chamber and reference chamber will result in venting from the other.

Figure 2:
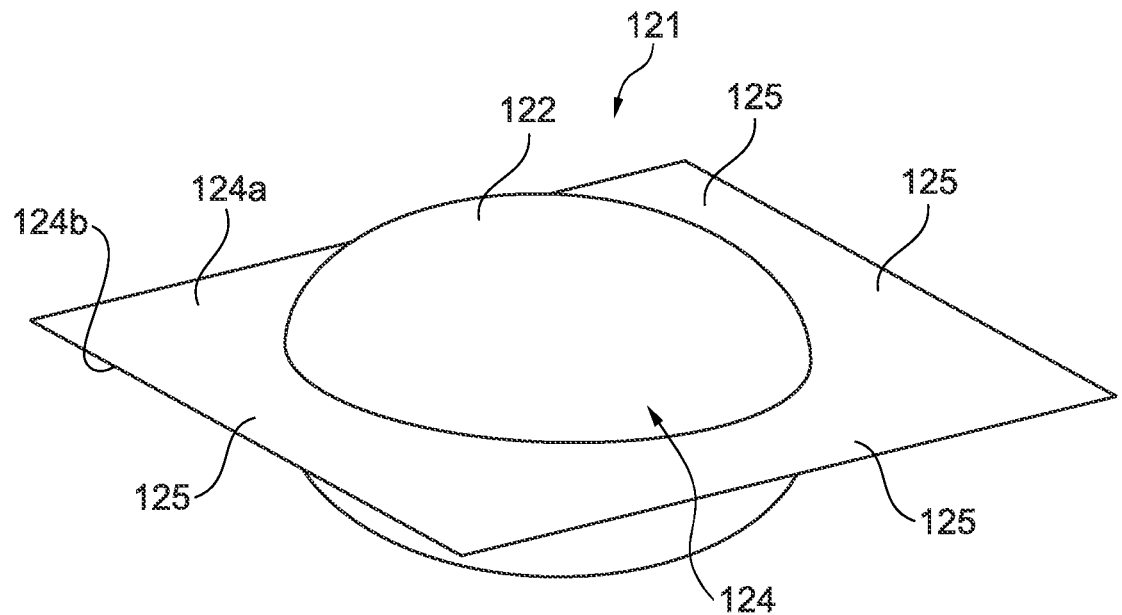
FIG. 2 shows an embodiment of a container for containing propellant in accordance with the present invention.
Figure 3:
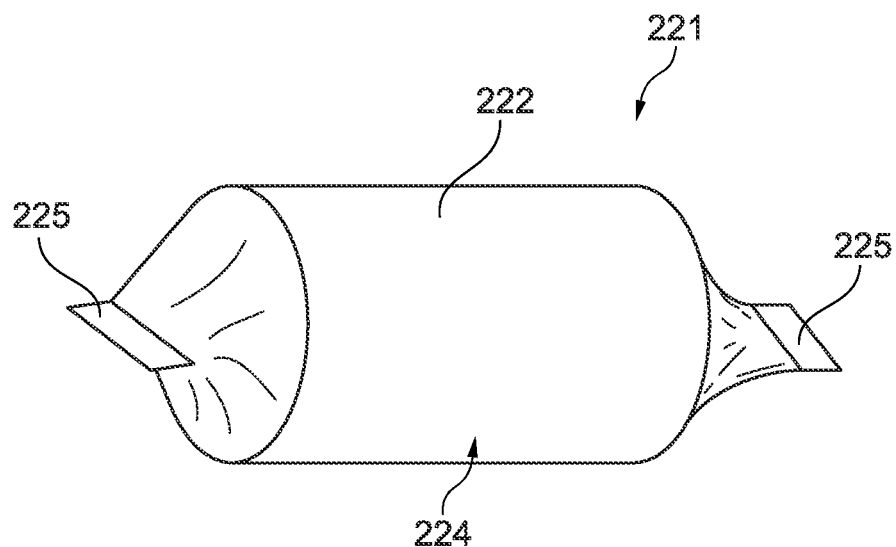
FIG. 3 shows an alternative embodiment of a container for containing propellant in accordance with the present invention.

In any of the described embodiments of syringes in accordance with the present invention, the propellant containers shown in FIGS. 2 and 3 may be used. The skilled person will appreciate that other propellant containers may be used and that syringes made in accordance with the present invention are not necessarily limited to using the containers of FIG. 2 or 3. In FIG. 2, a container 121 is shown to be made of an upper sheet 124a and a lower sheet 124b which together form a rupturable wall 124 of the container 121. The sheets 124a,124b are generally square or rectangular in shape in the embodiment shown in FIG. 2 and are sealed to one another about their periphery forming seals 125. The seals 125 circumvent a central volume 122 formed between the sheets 124a, 124b. This volume 122 is equivalent to the third chamber described above in relation to container 22 and contains a volume of propellant which is predominantly in its liquid phase at the operating temperature of the syringe (e.g. ambient temperature) due to being in the sealed volume 122. However, given that some of the propellant will be in gaseous form due to vaporization, the propellant will exert an outward pressure from within the volume 122. Therefore, the seals 125 must be sufficient to prevent substantial loss of propellant from the volume 125. Indeed, an ideal seal 125 will entirely prevent propellant escaping therethrough from the volume 122, however in practice, the seals 125 may be such that a finite, albeit acceptable and not substantial, amount of propellant may escape from the volume 122. The magnitude of "acceptable" amount will depend upon the perceived shelf life of the container (i.e. the length of time that the container 125 may remain in storage following manufacture prior to use), and the volume of propellant required to perform the desired action.

The material that forms the sheets 124a,124b is flexible and rupturable such that once ruptured (i.e. broken, torn or otherwise penetrated) a fluid pathway is provided therethrough into the volume 122 that is not resealable. The rupturable wall 124 is preferably substantially impermeable to the propellant contained in the volume 122. The actual gas permeability of the rupturable wall 124 may depend upon the chosen propellant contained in the volume 122. For example, for HFA 134a, it is preferable for the rupturable wall to have a gas permeability such that the volume of propellant remaining in the container 121 is sufficient to reliably deliver a dose of medicament. Therefore, the limitations on the gas permeability of the rupturable wall 124 are determined by the intended volume of medicament to be delivered and the initial volume of propellant contained in the container 121. To deliver a 1 ml dose of medicament, it is particularly preferable to ensure that there is at least 20 µl of propellant in the container 121. Therefore, over a two year storage period, a container 121 initially containing 100 µl of HFA propellant may lose up to 80 µl as gas through the rupturable wall 124 for there to be at least 20 µl remaining to deliver the 1 ml dose of medicament. In this example, the maximum gas permeability of the container 121 would be 0.365 g/(m$^2$. day). Whilst it would be preferable to have at least 20 µl of HFA propellant remaining after two years for delivering a 1 ml dose of medicament, a container 121 having a gas permeability that ensures that there is 5 µl or more of HFA propellant may be sufficient to ensure that enough propellant will remain after two years to deliver a 1 ml dose of medicament.

The rupturable wall 124 may include polyethylene and/or may include a polyamide and/or may include nylon and/or may include a cyclic olefin copolymer (COC) and/or may include a cyclic olefin polymer (COP). In some preferable embodiments, the rupturable wall may be composed substantially of nylon. In alternative embodiments, one or each sheet 124a,124b may be formed of a laminate of two or more different materials selected from polyethylene, polyamide, and metals (e.g. a metallic foil). The selection of the two or more materials may be based upon one of the layers providing a substantially impermeable gas barrier to prevent the propellant from escaping from the volume 122, and another of the layers providing mechanical strength to resist the outward pressure exerted by gaseous propellant in the volume 122. The rupturable wall 124 may be formed by co-extruding two or more materials.

Regardless of the type of material selected to form the rupturable wall 124, the seals 125 are formed between two like materials. So, in the case where one or both of the sheets 124a,124b comprise laminates of two or more materials, the sheets 124a,124b are arranged such that the interface between them comprises two adjacent like materials which may form the seals 125. The seals 125 may be formed by any of heat sealing, sonic welding or by use of an adhesive.

The shape of the container 121 may differ from that shown in FIG. 2. Indeed, any suitable shape that is able to contain the propellant in the volume 122 sealed by the seals 125 may be used in accordance with the present invention. However, the shape of the container should be such that the outward pressure exerted by the propellant is resisted to ensure that such pressure does not inadvertently rupture the container 121.

FIG. 3 shows a container 221 in accordance with an alternative embodiment of the present invention. The container 221 has a generally cylindrical rupturable wall 224 that is pinched at either end to form seals 225 that are sealed by one of the above described sealing methods. The rupturable wall 224 defines a central volume 222 for containing fluid propellant that, again, is equivalent to the third chamber 22 of embodiments described above. The rupturable wall may be formed from the materials described above in connection with rupturable wall 124 of the embodiment of FIG. 2. The container 221 has the advantage that fewer seals 125 are required since a single cylindrical piece of material is used to form the rupturable wall 224. Therefore, there are fewer potential leak paths that the propellant may escape the volume 222 through.

Either of the containers 121 and 221 may be used in any of the syringes described above in accordance with the present invention.

The containers 121,221 provide a small, convenient, portable, cost effective power source that may be used in a plethora of devices. For a re-usable syringe, for example, the containers 121,221 offer a simple and effective means to power the syringe over multiple uses, where the user removes a ruptured container 121,221 following an injection and replaces it with a new unruptured container 121,221 prior to the next use.

The propellant used in the containers 121,221 and indeed in any of the syringes described above may be any propellant that boils at a predetermined temperature. In preferable embodiments, the propellant is or contains HFA and further preferable is or contains HFA 134a. Indeed, mixtures of several propellant substances or propellant substances and additives may provide a propellant for use in accordance with the present invention. As described above, the propellant may be chosen to be one that boils at ambient temperature or one that boils at a temperature higher than ambient temperature, in which case a further heat source is required to cause the propellant to boil and move the stopper 16.

Throughout the description, claims and figures of this specification, 0 bar is considered to be defined as atmospheric pressure, so that all values of pressure given in bar are relative to atmospheric pressure (0 bar).

Throughout the present specification, the term "syringe" relates to and includes any medicament delivery device having a medicament container with an outlet and a moveable stopper for expelling medicament therefrom. As examples, the syringe may include a needle, a nozzle or a conduit attached to the outlet. In other embodiments, the syringe may not include any further components downstream of the outlet. The syringe of the present invention may be or form part of a subcutaneous delivery device, a nasal delivery device, an optic delivery device, an oral delivery device, an ocular delivery device, an infusion device or any other suitable medicament delivery device.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A syringe propellable by propellant that boils at a predetermined temperature, the syringe comprising:
   a barrel having an outlet at a front end;
   a stopper axially moveable in the barrel;
   needle in fluid communication with the outlet of the barrel;
   wherein the stopper separates a first chamber and a second chamber, the first chamber being axially forwards of the stopper and being configured for containing a medicament, and the second chamber being axially rearwards of the stopper and being configured to receive propellant for acting on the stopper to move the stopper axially forwardly in the barrel to expel medicament through the outlet upon actuation of the syringe; and
   a third chamber containing liquefied gas propellant;
   wherein the syringe is configured such that, in use, upon actuation of the syringe, liquid propellant is released from the third chamber and boils outside of the third chamber at or above the predetermined temperature to provide an increasing vapor pressure in the second chamber that causes the stopper to move axially forwardly and begin to expel medicament from the first chamber through the outlet;
   wherein a first pressure less than 15 bar is reached in the second chamber substantially coincident with an initial movement of the stopper, the mass of the propellant in gas phase increases as it boils while the volume in the second chamber increases with axial forward movement of the stopper, resulting in expulsion of medicament through the needle at a pressure that is maintained within 1 bar of the first pressure as a function of time from a point of initiation of the forward axial movement of the stopper until the stopper reaches a forwardmost position at the front end of the barrel;
   the syringe further comprising at least one trigger for triggering an action upon activation of said trigger, wherein the trigger is directly activated by the pressure in the second chamber when the pressure in the second chamber satisfies a predetermined condition; and one of a group including
   (a) wherein the syringe forms part of an autoinjector device in which the syringe is moveable relative to a housing of the autoinjector device between a first position in which the needle is within the housing and is not exposed and a second position in which the needle extends out of said housing and said action includes movement of said syringe between said first position and said second position; and (b) wherein the syringe has one or more indicators for producing a signal to indicate to the user one of the end of delivery of medicament, or that a predetermined time period has elapsed since the end of delivery of medicament, and wherein said action includes activating said one or more indicators to produce said signal.

2. The syringe according to claim 1, wherein the trigger is a resistive moveable component and the predetermined condition is satisfied when the second chamber is in fluid communication with the resistive moveable component so that the pressure in the second chamber is acting on the resistive moveable component, and when the pressure in the second chamber is sufficiently high so as to be capable of moving the resistive moveable component.

3. The syringe according to claim 2, wherein said resistive moveable component comprises a moveable piston that moves in response to an increase in pressure above a threshold pressure.

4. The syringe according to claim 2, wherein said resistive moveable component is put in fluid communication with the second chamber when a fluid passageway is opened.

5. The syringe according to claim 4, further comprising a sealing component that is moveable from a sealing position in which the fluid passageway is closed and an open position in which the fluid passageway is open.

6. The syringe according to claim 5, wherein the sealing component is moveable from the sealing position to the open position due to pressure in the second chamber.

7. The syringe according to claim 2, wherein the moveable component is moveable so as to move a further component.

8. The syringe according to claim 1, wherein the third chamber comprises a dispenser for providing propellant to the second chamber, wherein the dispenser is moveable from a closed position in which propellant cannot exit the dispenser to an open position in which a predetermined volume of propellant can exit the dispenser.

9. The syringe according to claim 8, wherein the dispenser has a capacity for containing propellant, and said predetermined volume is less than said capacity.

10. The syringe according to claim 1, wherein the third chamber is rupturable, and the syringe further comprises a rupturing portion, wherein the rupturing portion is configured to rupture the third chamber upon actuation of the syringe to fluidly connect the third chamber to the second chamber.

11. The syringe according to claim 10, wherein the third chamber comprises a flexible rupturable container for containing propellant.

12. The syringe according to claim 10, wherein the rupturing portion comprises a valve having a valve body, a valve stem, and a locking member, where the valve stem is slidably moveable relative to the valve body between:

i) a non-dispensing position in which an outlet port of the valve stem is out of fluid communication with the third chamber; and ii) a dispensing position in which the outlet port is in fluid communication with the third chamber so as to permit transfer of propellant from the third chamber through the valve stem;

wherein the locking member is configured to prevent return of the valve stem into the non-dispensing position once the valve stem slides beyond a locking position; and wherein the third chamber is ruptured when the valve stem is in the dispensing position and beyond the locking position.

13. The syringe according to claim 1, wherein the third chamber contains a volume of liquid propellant such that liquid propellant remains present in the syringe when the stopper reaches its forward most axial position in the syringe barrel.

14. A syringe propellable by propellant that boils at a predetermined temperature, the syringe comprising:

a barrel having an outlet at a front end;

a stopper axially moveable in the barrel;

needle in fluid communication with the outlet of the barrel;

wherein the stopper separates a first chamber and a second chamber, the first chamber being axially forwards of the stopper and being configured for containing a medicament, and the second chamber being axially rearwards of the stopper and being configured to receive propellant for acting on the stopper to move the stopper axially forwardly in the barrel to expel medicament through the outlet upon actuation of the syringe; and a third chamber containing liquefied gas propellant;

wherein the syringe is configured such that, in use, upon actuation of the syringe, liquid propellant is released from the third chamber and boils outside of the third chamber at or above the predetermined temperature to provide an increasing vapor pressure in the second chamber that causes the stopper to move axially forwardly and begin to expel medicament from the first chamber through the outlet;

wherein a first pressure less than 15 bar is reached in the second chamber substantially coincident with an initial movement of the stopper, the mass of the propellant in gas phase increases as it boils while the volume in the second chamber increases with axial forward movement of the stopper, maintained a pressure axially rearward of the stopper within 1 bar of the first pressure as a function of time from a point of initiation of the forward axial movement of the stopper until the stopper reaches a forwardmost position at the front end of the barrel.

15. The syringe of claim 14, further comprising at least one trigger for triggering an action upon activation of said trigger, wherein the trigger is directly activated by the pressure in the second chamber when the pressure in the second chamber satisfies a predetermined condition, the action selected from a group including (1) movement of a protecting needle shield between a retracted exposing position and a forward protecting position; (2) movement of the syringe between a first position where the needle is wholly within the housing and a second position where the needle protrudes from the housing; and (3) producing at least one signal indicative of a status of the delivery of medicament.

16. The syringe of claim 15, wherein the action triggered upon activation of the trigger is producing at least one signal indicative of the an end of delivery of medicament.

17. The syringe of claim 15, wherein the action triggered upon activation of the trigger is producing at least one signal indicative of a predetermined time period having elapsed since an end of delivery of medicament.

* * * * *